(12) United States Patent
Medrano et al.

(10) Patent No.: US 7,972,790 B2
(45) Date of Patent: Jul. 5, 2011

(54) STAT6 EFFECTS ON LIVESTOCK ANIMAL GROWTH

(75) Inventors: Juan F. Medrano, Davis, CA (US);
Gonzalo Rincon, Davis, CA (US);
Charles Farber, Los Angeles, CA (US);
Donald Joshua Nkrumah, Duluth, GA (US)

(73) Assignees: The Regents of the University of California, Oakland, CA (US); Merial, Duluth, GA (US)

( * ) Notice: Subject to any disclaimer, the term of this patent is extended or adjusted under 35 U.S.C. 154(b) by 106 days.

(21) Appl. No.: 12/112,752

(22) Filed: Apr. 30, 2008

(65) Prior Publication Data

US 2009/0275022 A1 Nov. 5, 2009

(51) Int. Cl.
*C12Q 1/68* (2006.01)
*C07Q 21/04* (2006.01)
*C12P 19/34* (2006.01)

(52) U.S. Cl. ............ 435/6; 536/24.3; 435/91.2

(58) Field of Classification Search .......... None
See application file for complete search history.

(56) References Cited

U.S. PATENT DOCUMENTS

| | | | |
|---|---|---|---|
| 6,383,751 B1 | 5/2002 | Barendse | |
| 2003/0092019 A1* | 5/2003 | Meyer et al. | 435/6 |

OTHER PUBLICATIONS

Ghilardi et al., "Defective STAT signaling by the leptin receptor in diabetic mice," 1996, *Proc. Natl. Acad. Sci. USA* vol. 93, pp. 6231-6235.
Smith et al., "Carcass traits and micosatellite distributions in offspring of sires from three geographical regions of Japan," 2001, *J. Anim. Sci.* 2001. 79:3041-3051.
Womack et al., "A whole-genome radiation hybrid panel for ovine gene mapping", 1997, *Mammalian Genome*, 8, 854-856.
Farber and Medrano, "Putative *in silico* mapping of DNA sequences to livestock genome maps using SSLP flanking sequences," 2003, *Animal Genetics* 34:11-18.
Takeda et al., "STAT6: its role in interleukin 4-mediated biological functions," 1997, *J Mol Med* 75:317-326.
Tamura et al., "Novel dinucleotide repeat polymorphism in the first exon of the STAT-6 gene is associated with allergic diseases," 2001, *Clinical and Experimental Allergy* 31:1509-1514.
Maffei et al., "Leptin levels in human and rodent: measurement of plasma leptin and ob RNA in obese and weight-reduced subjects,"1995, *Nature Med* 1:1155-61.
G. Rincon et al., "Polymorphisms in the STAT6 gene and their association with carcass traits in feedlot cattle", Stichting International Foundation for Animal Genetics, 2009 *Animal Genetics*, 40, 878-882.

* cited by examiner

*Primary Examiner* — Steven Pohnert
(74) *Attorney, Agent, or Firm* — Weaver Austin Villeneuve & Sampson LLP

(57) ABSTRACT

The present invention provides for selection of livestock animals, including bovines, whose genotypes based in the STAT6 gene are correlated with phenotypes reflecting desirable carcass and feedlot traits. These phenotypes include back fat (BFAT), calculated yield grade (CALCYG), cutability (CUT), hot carcass weight (HCW), dry matter intake (DMI), days on feed (DOF), back fat rate (BFAT RATE) and average daily gain (ADG), based on the knowledge of the STAT6 genotypes. The predictive value is based in part on the discovery that certain single nucleotide polymorphisms (SNPs) within the STAT6 gene are linked to phenotypes of economically these important carcass and feedlot traits. Also provided are SNPs within the STAT6 gene useful in reliably distinguishing between a *Bos taurus* and a *Bos indicus* bovine. The invention provides methods and compositions for determining STAT6 genotypes and for screening livestock animals to predict which animals will have desirable carcass traits and feedlot traits, allowing producers to selectively breed and manage animals based on desired characteristics, thereby maximizing productivity and profitability in commercial meat production operations.

27 Claims, 12 Drawing Sheets

FIG. 1A

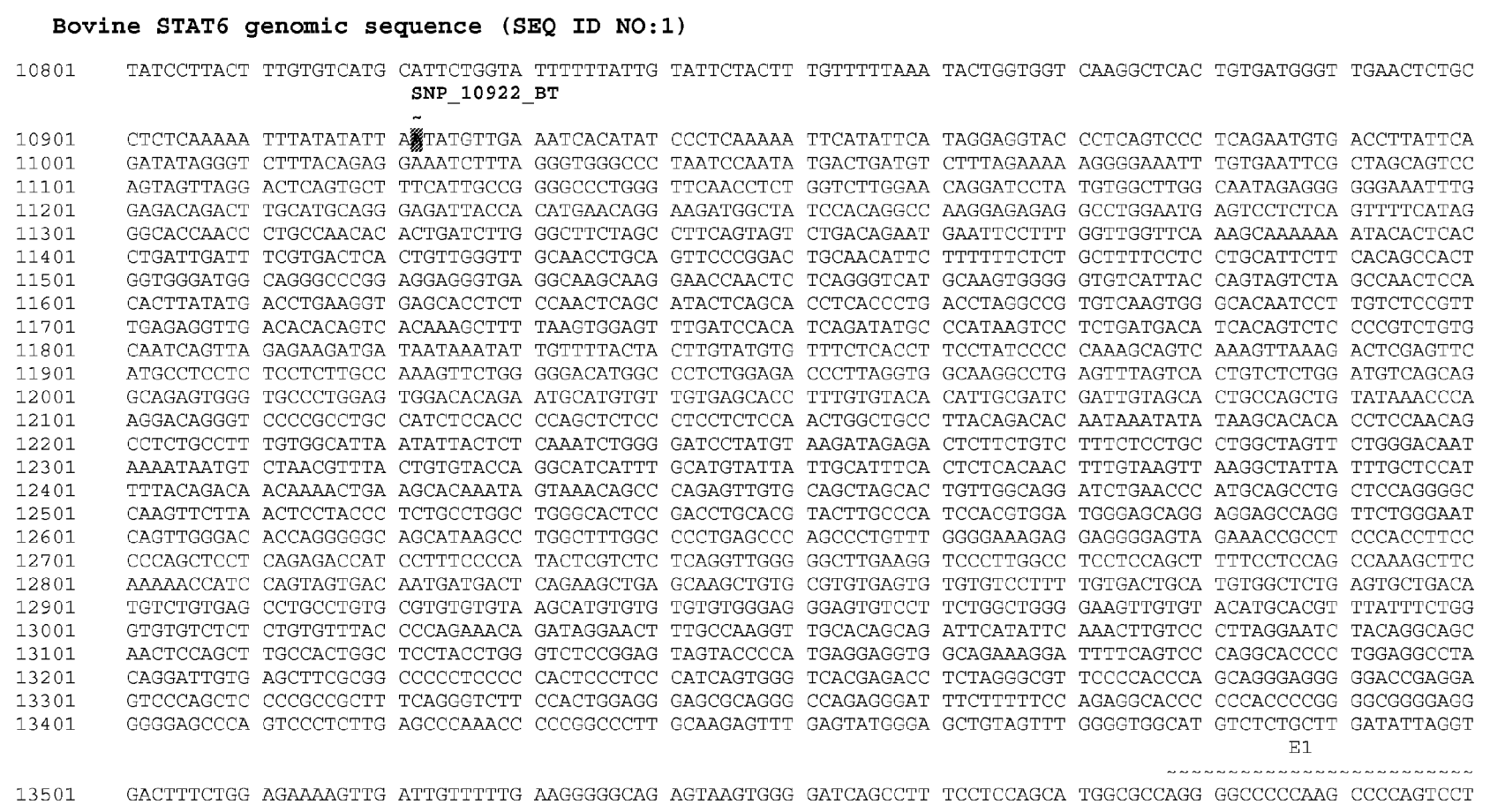

Bovine STAT6 genomic sequence (SEQ ID NO:1)

```
                                          SNP_10922_BT
                                                ~
10801  TATCCTTACT TTGTGTCATG CATTCTGGTA TTTTTTATTG AATATGTTGA TATTCTCACTT CCCTCAAAAA TTCATATATTCA TTCATATATTCA TAGGAGGTAC CAAGGCTCAC CCTCAGTCCC TCAGAATGTG TGAACTCTGC
```

(Figure content: bovine STAT6 genomic sequence rows from 10801 to 13501, with SNP_10922_BT marker highlighted near position 10901, and E1 label near position 13401.)

FIG. 1B

```
                                                                                                                   E1
       13601 GGCTCCCCCT CCCAGCCCAT GCTCCCCCTAC TCCATACCAG AGGCACACAT GCTCACCCCA CTTTCTTCCT CTTCCTCCTC CAGCCCCACTT TCTCTTCTCT
                                                                   E1
       13701 GTGTCGTCAG AGCTCCAGGG AGGGACCTGG GTAGTCGGAG AAGCCGGAAA CAGAGGGCTG GGGCAGCCAC TGCTTACACT GAAGAGGGAG GCTGGGAGAG
                                                                   E1
       13801 GATTGTGTGT GTGTGTGTGT GTGTGTGTGT GTGTTTTATT TTTGGTGGTG GTGGTGGAGG AGGGGTGTTA GCAGGGCCAG TCCTGAACCC
                                                                   E1
       13901 GCTGGACAGA GCTACAGACC CATGGGGCCT GGCAGAGCCG GCTGAGAGAG GGAGACGACA ACAGAGGGGT TGCCAAGGTG AGGGGATGCC TCCAAGGAGG
                                                                   E1
       14001 GAGGGTGGGG GGCCCTCTGAC TACCAATGTG GGGGGGAGGA GGGGAGTGCT TTTCAGGATC CTGCCTGGGC AGAATGGATG GTCCCTAAGA AATTGTTTCA
                                                                   E1
       14101 GCTGGGGGCTG GTGGCTGGTG TTACTCAGTT TCGGCAGTTT CGAAATATCA GAGGAATCTG GAGTGGGTAC AGGCCCAGCA CTTGCCCCGC TCCTCCCCAA
                                                                   E1
                                                                       SNP_14257_BT
       14201 CATGGGTCAC TTTTCCACA CACCCCATCC CCCGCAATCC AGGGACGTGT TAAGCC░GGG GAAGGAGGGC AAGGAGGTGC CCCTCTGCCC TCTGGGTTGG
       14301 GGGGAAGTGG CCGCCCCTCC CTATAGAAAA CTGATGCCAG GGGGCAGTGG ATCCTCCACA GACCCCTATC CGGGCCCCCC ACAAAGGTTC CTCTTCAAGG
       14401 GTGTGGCCAG GGGGTGAGCG TGTCCCAGAA GTAGAACCTC ATGGTGCCCC AGAGGAGGGG GAATTTCCCC CTCAAAACTG CTCCACGCTT GGCCCGGCGG
       14501 CGTCATGGAG TTAACCCTCC TGGTGCCTAA CTGGCTCCGC CTGGCTCCGC AGGAATCTCG CCCCGCGCGC CCCCGCCCCC GCACACACAC TGGGCAACTC CGAGCAGCTC
       14601 TTCTGACTTC TGATCCTGTG GTCCCACGAT CAGAGGACTC AGGAATCTCG GGGGTTGAGG TGAAGTTTAG GCCACGAAGC GGGGCTGAGG AAGATCTGG
       14701 ACTTCCCTTC CCCATGGGGA AGGGAACGCG GGCCCCCGCC CCCAGGCCA TGGCTTCCTC CTCCCTGTCG GTGTTCAAGG GGCTTACAG CAGAAGATGC
       14801 CCCTGGCCTG GCAGGCCGAT TGAGCCAGCC TGGTTATTGG GTGGGAGTGG GGGAAAGTCT GGCCCCTCGC TGTCGGAGGA TGGAGTAGGG GAGATTTGAA
                                                                                                                    SNP_14636_BT_Tag
       14901 GGCAGGGCCA TGCCAGGAAG CTGGTCACTC TTCCTAATCT AGGGGATATG AGGGAAAGGG GAGCTGCCTC TGACTTAGGG ATCACCTC░G TCCCCGTAGG
       15001 GTAGAGATAG AGGTCAAAGG TCTGAGCACC CTGAGAAAACA GGAGAGAAAG AGGGAAGAGA GGAATGGAGT CCTCCCTTGA GTTTGAAACA CAAACCAAAA
```

*FIG. 1C*

```
15101 GGTGCCCCAC CCCAAGGTGG GTGTAGAGAA AGGTCTATGA GAGGACCCTG AGCAGGAGGG GGAGGATTCT GCCTTTGGGA GAAAAGAGGT TAGGGGGATA
15201 TAGGAACTGG GGAGGAGCAC GGATCTCCAG AAAAGGGGCC TCTCTGTTCT CTATTCCTTT GGGAGTCCTG CATCTCTGGG GGAGAGGGGA GAAGCTAACG TGCTGCAGGA
15301 GAACTTGGGG CTAACTGGGT CTAGGGAGTT CTCCACCCCA TCCTTTCTGT AGATGGGGAC TTTTGAGAAA CATGAACTGA
15401 GAGACCCCTG GGGAACCACT GGTTTACCCA CTCCGCCCTG CAGAACCACT AGATGGGGAG GCAACCACCC CCTCCTATT GCAACCTCTC CTTCCTCAG
15501 GCCCCTTTC CTTCCTTCC TTGAGTCCT CTAGCCTCC TGCCCCTCC TTTTGCTTT CTCTGAAGGC TAATTAACCT CACTTTTCT CCTTCCTGAG
15601 TTCTCTCTAC TCTTCCTCTT GCTCCATCTC CTCTTCCTCA GTTCCTCCTCC CATGCCCCCC CCCTCTTGGG ATTATGAGAT CTGGATCCAG AAGGGATCCT
15701 AAGGTACAG AGTGGTGGTT TATCCCCACT TGGGTTCAGA TCGCTTGCAG AGTGGCCTTG GCAAGTTGGA GAACCTCCTT GAGCTCAGTT TCTCTACCTG
15801 TAACAGGATG ATTTTATATT TTAAAAATTG TTGCAAGATG CTAGTGAGGT AAGGCGCTCA GTGTAATGCC CCATACATAG TAAGTGCTTA ATGAATAATA
15901 GCTATTATTA CTCTACCATC TTCTTCTTCC TCATCTAGCC AGGCAGTTTT CAGATTGTTT CATGGAACCC TGGAATTTG AGGGATTTCT CTAGGGATAC
16001 CTTTGGGTC CAGAGGTGA GAGAGGAAAG CAAGAAGTGG TAGAATTCCA GGTCTACCAC ACTTGATTTC AACAGAGAAA TTCCAATTTT ACATAACTGG
16101 CTAAAACGGT CTACTTCTTT AAAAATTTC GAAAGTTCAT ACTTTACCCA AGCCTCATAT TTTATAGATG AGAAGATTGA GGTCCACGGA GGGGAGTTT
16201 CTTTTGTTT ATTTGTTTT AAAATCTTT GACCATGCCA CAGGATCTTAG GGGATCTAG TTCCCTGATC AGGGATTTGT TCCCTTCATT GGCAGCATGG
16301 AGTCTTAGCC ACTGGATCAC CAGAGAAGTT CCGAGGGGAG GTTTCTGCC AACAGAATCA GAGCTACAAC CCACATTCTC TGCCTTCTCT CAGAGAGCTT
                                              SNP_16084_BT_Tag
16401 TCCCTACTGC CCCATTGCCC CTGTCTCTTA CCCTCTTCCC TCCCCCAACT GGCTGCAGCT CAGCTCTTCC CACTCCATTA TACTCTTGAA
16501 GAAATACCT TGTTTCAGGC TTTGGCCAAA GAGGTTCCTG GTTTGATATA GTCTGGCTGA GAGTTGTGGT TCTGAAAGGG CTGTCTATGG
16601 GAGTCCTTG CTGCTGTGC CTGCTGCTT GCGTCGCTTT AGTCGTGTGT GACCCATAG GTGGCAGCCA ACCAGCTTC CCGTCCTGG
16701 GATTCCCAG GAAAGAACAT TGGAGTGGGT TGCCATTTCC TTCTCCAATG CATGTAAATG GTGAAGTCGC TCAGTCGTGT CCAACTCTAG
16801 CGACCCCATG GACTGCAGCC TACCAGGCTC GGGGGTTTCT AGGCAAAAGT ACTGAGTGG GGTGCCATTG CTTCCTCCTG GGAGGTCCTT
16901 GGCTGCCCGA AAAGGTCAAC TTCCAAATAA CCTTGTTCTT TTTCTTCAGT GTTAATGTCA GTCCTCAGT CATGTCCAGT CTTCACAACC GCACGCACTG
17001 TAGTCCACCA AGCTCCCTG TGTGTGGAAT TCTTCAGGCA AGAATACTAG GGTGGCTTTG CCATTCCTTT CTCTAGGAGA TCTTCCTGAC CCAGGAATCA
                                                                                                  E2
17101 AACCCAGGTC TCCTGCATTG CAGGCAGATT CTTTTACTTTC TGAACTACCA GGGAAGCCCT CTTTTCTTC AGGCACCCTC CAAACCCCAG ATCATGTCTC
17201 TGTGGGGTCT GGTCTCCAAA ATGCCCCCAG AAAAACTGCA GCGGCTCTAT GTCGACTTTC CTCAACACCT GCGGCATCTC CTGGGTGACT GGCTGGAGAA
       E2
17301 CCAGCCCTGG TGAGTCCTGG CTGCCCCCCA TCAGTCCCCC AGGGGCCTCCC GAGTCTGTAC CCACCTACCT GCCTTCTCAT TAGGTTTTAT TCATCCCATT TTGAGACTTG
17401 GGACTCATTA TTGTACATGC AGTGGTCAG ATTTAGCCAG GAGTCTGTAC CGCATCAAACC AGACTACGGC GTGTTGACAT ATGGAGTTCC TCACCCCTT
17501 AGGAACCTGA GCCAAAGAGG AGGGAGGTCA GAGCTGGGCC AAGGGACACA CCCACAACAG CTGGAAAAATT GGGAACAAAG GGCACAGCT GAGGACTACG
17601 GAGGGCCTGG ATGGAGGATA AGAGGAGGAA GGAGCTGCTG AGCTGTTTGC TGTGGGGTGA AGGGGCAGTA GAGTCGAGGA AGCCCTGACC TGAGGTGGCC
```

FIG. 1D

```
                                                                                              E3
17701         TCATCCTGAT CTTCCTGCAG GGAATTCCTT GTCGGCTCAG ACACCTTCTG CTGCAACATG GCCAGCGCCC TACTTTCTGC CACTGTCCAG CGCCTTCAGG
                                                  E3

17801         CCTCAGCCGG AGAGCAGGGG GAGGGGAACA CCATCTTGCA ACACATCAGC ACTCTGGAGG TGGGCGCAGG AGGGAGGGGA CAGGGCCAGG GTGGGGCCTG
17901         GAGCTGGGGT GAGCATTGGA TGCTGGAAGG GAATTGGTAT TCCTCTGTTT AGCTGTTAGC TAGCAGGCAA ATTAGATTCT AAAAGCATGC AAATGCATGC
18001         AAACTTCTGG AGTCTATGAT TGTGCGGCCT TTTAGTTCAT GTGTGAATGG GGAGGGGGAT TGGTGAGGGA GAATGACATG GGTAAGAGCA AGGCTAACCC

18101         CATCTACCAC TCTTCATTTC TAGACCATTT ATCAGAGGGA CCCCCTGAAG CTGGTGGCCA CTTGCAGACA CATACTTCAA GGTGAAAAAA AAGCTGTTAT
                 E4

18201         GGAGCAGGTA TTGTGATACC CCACCCTCCA ACCCCTGGGA ACTTTAGCCT GAGCCATTAG AAACTAGAAG GGATTTGAAC TTCAGAAAAA
18301         GCTCAGTGTT CTAGGTCCAA GATGATCAAA GGGGTCAGAG GTTCCT TGAGCCCCAA TGAAGCTTC GAGAAGCTTC CAATGAGGAA CTGAGGGTAG
18401         TGAGAGGTCT GGGGCAAGTG ATACAGAGCT GTTATCTCCA GAAGATTCCA AAATGTCAAG AAGAAGAGA AAGGAAGAG ACAAGGAAG
18501         TGGTCTATTT TCTGCAGAGC ATGGCAGTGG GCACCCCTTT AGGGAGTGGA GGCTGAGGGA AAAGGGATGG ACAGAGTGTT TCACTGTTG CCTGTCCTTC
                                                     E5

18601         CTTGCAGTTC CACCACCTGC CAATGTCCTT CCACTGGAAG CAGGAGGAAC TCAAGTTTAA CACAGTCCTA CGGAGGCTGC AGCACCGGGC CGGGGAGACC
                                       E5

18701         CGCCTTCTCC GGGAGGCCCT GCAGCCTGGA GCTGAGGCTG GCCAAGGTGG GATTCTGGGG AGTGTGTGGG AGTGACCCCC TCTTGGATCT CAACCCTGAT
                                                                                                     E6

18801         TGAACCTCTT AAATATATCT GCACCCCGAT TTTTGCCCCT ACCCTCAGTG TCTTTGCACA GCTTGATAGA AACGCCTACC AACGGGACTG GGCCAAGTGA

18901         GGTGAGTAAT GGACTGAGAT GTGGAGACTG AGCTCAAAGT GCAGACTTTG AGGGTCTCAG ATCTGTGGAG GGATGGTGAG TAGACCTCTG AGAGGTGAGA
                 E6                                                                                         E7

19001         AAGGGAGGCT TACCCTCCAG AGCTGGGCAA AGAGGAAGCG TGTGGCTCCG GCTCAGGCCC CACCTGCCCA CAGGCCCTGG TCACGCTGCT GCAGGAGACT
```

FIG. 1E

```
                        E7
19101  GTTGGTGAGC TGGAAGCTGC TCAGGCTCTG GTGCTGAAGA GGATCCAGAT ATGGAAGCGG CAACAGCAGC TGGCAGGAAA TGGTGCACCC TTTGAGGAGA
              E7
19201  GCCTGGCTCC ACTACAAGAG AGGTGGGGAA GGGCTGACAG GGAAGCGGGA TGCGCTGGGG GTGGACATCT GCTCTCCCTG CTGGAGGTGT GAGAGAGAGA
19301  AACCAGGCCA GAGGGTCTCG GGGTGGGCCA AGACTTGGAG AAGCCAGTTC CAGAGAGCC  ACCCATACTG TTGTTCAGGT CATGTCTTGC ACACACGCAC
19401  CAGGCTGACC CGGCATGAGC AGGCATTCCT CCAATCTATA CTTTTCTCTT CGAGCTCCAT GCCCAGAGGG CTGGGAAGTC CTGGGAAGTG CTTTTTCGTTT ATTGGCAGGG
19501  TATCTTTCAA TATGCGCAAA AGCATCGTGC CTGCTGGCCT CAGAACCTGG TATCAGACCC GGCAGCTCGT TTCAACACAG CTTCCAGGCA
19601  CTAAGCGGGA ACCTTGCCCC AGAGCCAAGG CGCGTCCCAC CACCCCTTCA GCCCAGTGC  CTTGCTGTCA CACCCACTGC TCATCCCTAA CCCTCCACAC
19701  ACACTATCCT GCTTTCTTCC TGGGTTGAGG GGTGAGGGGC GGTGAGGACC TGGAAGACTG  CGCCCCCTGA CCACGGTCCT GCCCCCAGGT
                                                   E8
19801  GTGAGAGCCT GGTGGACATT TATTCCCAGC TGCAGCAGGA GGTGGGGGCA GCTGGTGGG  AGCTTGATCC CAAGACCCGG GCAGCCGCTGA TTAGCCGACT
                E8                                            SNP_19597_BT_Tag
19901  GGATGAAGTC CTGCGCACAC TCGTCACCAG GTATGAGCCC CCCTGCCTG  TGGAGAGCAG ACCCCCAAGGA AACAGGAGGG TCAGAGTTGT GGTGGGGGGA
                                                                                                        E9
20001  GGGGCAGTGG CGCCCAGAGG GACCCAGCTG TTCACTTCCC TGTGTCTTCC CAGCTCTTTC CTGGTGGAAAA AGCAGCCCCC CCAGGTTCTG
              E9
20101  AAGACTCAGA CCAAGTTCCA GGCCGGAGTT CGATTCCTGC TGGGCCTGAG GTTCCTGGGG GCCCCAGCCA AGCCTCCCGCT GGTCACGGCC GACATGGTCA
20201  CGGAGAAGCA GGCGAGGGAG CTGAGCATGC CCCAGGGGCC CGGAGCTGGA GCGTAAGCTG GGGCTGAGT  GGGAGATGGA GGCCAGAGGG
20301  GCCTGGGAGA CCGGCACAGT GAAGGGGGCT GGTGATGAT  GGGAGGCAG GGCCATGGGG CTGTATAACA GTCAAGCCAG AGGAAGGGGA
20401  GGGACCCACC AGTGCTGGAA TGGGCTGGAA GCCTCCTGAT TTGGCTAAGA TGGGGGTTTC TCCCTCAAGA ACCCAAGTAG GGAGATAGAG ATTAGGGACC
                                                                                                                E10
20501  AATAGTCTAG GCCATTCACC TGTGCACTCA AGCTCCTGCC ACTCCTGGGC CAATCGGGAT GAGCCCCTCT CTGACTTGCC CTGGCAGAGA AAGCACCGGA
20601  GAAATCATCA ACAACACCGT GCCCCTGGAG AACAGCATTC CTGGGAACTG CTGCTCTGCG CTGTTCAAGA ACCTGGTGAG AGGCCTTTGG GGAGCAGTGG
```

FIG. 1F

```
20701  GTGGGCGTCC TCAGGCCAGG CAAGTGTCCT TGGGGAGCCC AGGAGAAGCA GTTTCTGCCT TCATCCTCCT CGCTCTCACC CCTTCCCCCA
                                                            E11
20801  GCTTCTGAAG AAAATCAAGC GGTGTGAGCG GAAGGCACCC GAGTCTGTCA CCGAGGAGAA GTGCGCTGTG CTCTTCCTCCA CCAGCCTCAC GCTTGGCCCT
              E11
20901  AACAAACTCC CCATCCAGCT CCAGGTGAGC TTGAGTCCCA GGTGCCCTGG CCACACACGG AGGCCTGGAT CCTCATTCCT CATGAATGCC CTGTACCCTG
21001  TGGGTCTGGG GTTCACGCAT GTGGGGCTC CAGCGGGAGT CAGCGGGACG AGAACTCAAG TGCACACTCC AGGAATGAC GTGTGTGTT ATTGCATATG
21101  GCCCTGTGGG ACTGTGTCCC AGTTTTTGCA ATAAGAACTA TTTTCCTTAG CCATGCCAAT GGCTAAGGCA TTGAAGCACT TTTCCTTAGAC CAGGCACTG
21201  TTTTAAGTCA TACGCATGCA CACACACACA GGGTTTGCAC AGTTAACATT ATGAGGGAGT TATTCTTACT AGCCTCATTT TACAGATGAG AACACTGAAA
21301  CACAGAGATT GAGTACTTAG CCTGGGTCAC ACAGTCCTG CTGGTATTG AAACCTGGAG GTCTGACTCC ATAGCACTGA CTCCTCACCA
21401  CATCTCAGCA GGGAGGCCAT AATTCAGCTT CAGAAAGCAC TCGTTCACAC ACCACAAATT TTTAACTGTG TGGTGGGAGT TCAGGAGCTT CCGGGTATCC
                                                                                                              E12
21501  TCAGAGCCAG CCCTCTGCAG AGGCCCCTTG TCCCCCAGTA CCAAGAGCTC CCTTTCCTCA CCCGCTTCAG GCCCTGTCTC TGCCCCTGGT GGTCATCGTC
21601  CATGGCAACC AAGACAATAA TGCCAAAGCC ACCATCCTGT GGGACAATGC CTTCTCTGAG ATGGTGAGAC AAGACCCGGA GTTGGGGGGA GGAGGGCTA
21701  TAACCTGGCG GGTGGGTGCA GGCTGGTGGG CCGATTCTG GTGCTCACATG AGAGTGACCA TAACTCCTTC TCATGGACTT TGTTTCTGTC CTTCTGACCT
21801  CCTTTCGTGC TAATCTTAAC ACCGATTCTG TGGTAGCACC TTAAGCACCT GTTGGAAAAG CACCATTTTT CTTGGGCAGA CTCAGGGGGA CAAGGCTGGG
21901  GAGGGACAGT CTTGGGGAGA GGGGGAGGAT GCAGGCCCTT CTGATGAGGA ATGGCTACGT CAGCCTGAGG CTCCCTCACC TTCTCCCCTC CCCTCCCAGG
22001  ACCGCGTGCC CTTTGTGGTG GCTGAGCGGG TGCCCTGGGA GAAGATGTGT GAAACTCTGA ACCTCAAGTT CATGGCTGAA GTGGGACCA ACCGGGGTT
                                                              E13
22101  ACTCCCAGAG CACTTCCTCT TCCTGCCCCA GAAGATCTTC AATGACAACA GCCTCAGTAT AGAGGCCTTC CAGCACCGTT CTGTGTCCTG GTCACAGTTC
              E13
22201  AACAAGGTCA TTCCCCTTGC CTTTGGACCT CCCACCCCCA AGCGCTTCAT CCCTGGGGCA CTCAGGGCCT CCCAACCTC TGCCCAGGAA CCAACCACTA
22301  GGATTTTCAC AGTGCCCTGC CATGTTCATC CAGCCCTGGC CTGCCCTGGC AGGAGGGGCT CCAGGCAGGA AAACCCCTTG GCTCCTGGC ATCCCCCTAG TTTTTGTCTG
22401  GGGCCCTCT GTCTTCCCTT TTGCTAGTGA TTGCATGAAC TCACCCAGAC TGTGTGTAAA CACAGCTTTG ATTCAAAATG ACTTTGACCC ATTGGGAAAA
22501  TAGTTCTTAT TGTAAAAACC AGGACAAAAT CCCACAGGGA CAAATGCAAT AACACCAGCA ACCATGCGTT GACAGTTAG GATATGCCAG ATTGTACTTG
22601  AGCACTATAT GTATGCTATC TCACTTAATC CCAGTAAGT CTCTTTAAGG TAGGTACTAT TACACCCATT TTATAGAGGA TGAACCGGCT CAGAGATGTT
22701  AGTAGTTTC TCCAAGGCCT CCCAGTAAGT GAGGCCCATAT GAGGCCCATAT TTCTGACTCT TGATTTTAGC TACGCCCCCC AAAATAAGGT GGCTCAGGAC
```

FIG. 1G

```
22801  TGGATCTCGTT ACAAAAATAG GAAAAAAATGG AGGTCTGAGT GTCTTGGTTG AAGATCAGCT GAATCAATGC TGTCAGTAC  TGATCTCTTT TTTAAAAAAG
22901  GAAGAAAGAA AAGCCCACAC GACCAGAGGA TGTGTTAGCA AAGGAACAG GACACTTACA TCCTGCAAAC TGCCTTCTCT GGACACCACT TCCGCCAGGC
23001  CTCATTCAGG AGGGGGTGGA GCACAGTGGT TATGAGGGGG CCCAGCCCAG ACTTCCTGGA CTAAATCCCA GCTCTGCTTT TCACTGGTTG TGTAAGAAGC
23101  AAGTTATTTG ATCTTTCATT GCTTTCATTT CTTCATCTGT AAGATGGGAT ACTCATGGGA TCTTCATCCA TAGATGTGTA AAGATCGGAT ACAGTAATTT
23201  ATGGCAAGAG CTTGGACTAG TGCCTGACAC ATGGGAAGCT TGAGTGTGGC CATTGTCGTT GATGGGGTCT CAGGTGCAGG GTGGTCCCTC AGTCCTGTGA
                                                                                                              E14
23301  CTCTGTTGTG TCGGTACTCA CAGCCCAGTG GCTGGCCTAG CCAAGGCTCC CC GCTCTGGCCC TCTTGTGCTC ACACCCGGCTC CCCTCTCCCC ACAGGAGATC
                                                              E14
23401  CTGCTGGGTC GTGGCTTCAC CTTTTGGCAG TGGTTTGATG GTGTCCTGGA TCTCACCAAA CGCTGTCTCC GGAGCTACTG GTCAGACCGG TGAGTCCCTG
                                                                                                              E15
23501  CCCCAGGTAA CCTGAGGATC TGGGCCTCCA GATCCTGCTC CACACACTAC GCCCCCACCC ACAACCTCTC CTTCATCCTG GCCAGGTTGA TCATTGGCTT
                                                              E15
23601  CATCAGCAAA CAGTACGTCA CTAGCCTTCT TCTCAACGAG CCTTCCTCCT TCGATTCAGT GACTCAGAGA TTGGGGCAT CACCATTGCC
23701  CACGTCATCC GAGGCCAGGA TGGTGAGGTC ACCCCAGCCA GTCCTCTGCC TCTGTGCCTG TGCCCTCAGG GGTTTCTTCT GAGAAAGGTC CTGGCCTTCT
23801  TTGATGCCAA CCGTGATCTT CAGGAAGTTC TTCCTTAGGT TCAACTTCTC TTCTTCCTTC TGTGGCCTAA ACTTCTACCT TCTCACTTGG AGTTTGGTGG
23901  GAATGGGGAC TGGTGGGACC CTCACACCAG CTCTTCCTCT CCTTACCTTG GTAGATTGAG AATGAGTCCA ACCATCGGGG TAGGTTGGGG AAGGGGAATT
                                                                               E16
24001  AAGTCTGGAC AGAGGGGACT CATGGCCTCA TTCCTTATGT AGGCTCCCCA CAGATAGAGA ATATCCAGCC ATTCTCTGCC AAAGACCTGT CCATTCGCTC
                                                              E16
24101  ACTTGGGGAC CGAATCCCGG ACCTCGCTCA CTCTACCCCA AGAAACCCAA CTCTACCCCA AGAAACCCAA AGAAACCCAA GGATGAGGCT TTCCGAGCC ACTACAAACG TGAGCTGTGA
24201  GCCGGGGCTG GCAGCTCTGA CTCCTTCTGT GGTCCGCCTC CTCCCTGCTC CCACCCACC CTGGTTGCCC CCACCCACC TGCTGTGTGT CATCCCTGAC TTCTTCCTCC
24301  ATTGTCATTT CCCTGCTTCT GGACCCTGCC CATCATCCAT GCTCACCTTT TC AGCTCCCC TTCCTCCCTA ACCCGGAAGC ATTCCATGGC TCTCCTTTCC
                                                              SNP_24000_BT
```

FIG. 1H

```
                    E17
24401   TCCCCACAAT AGCTGAGCAG ATGGGTAAGG ATGGCAGGGG TTATGTCCCA GCTACAATCA AGATGACTGT GGAAAGGTGA GTGTGCTGGT GTGGATGGAG
                                                                                                              E18
24501   GGCAGGCTTG ATACTTATTT GTAAGCAGGA AGTGTGGCAT CAACCCCTGG TCAGTCACAC ATGCCTCCTC CCCTCCTCCA GGGACCAGCC ACTTCCCACC

24601   CCAGAGCCCC AAATGCCTAC CATGGTGCCC TCTTTACGATC TTGGAATGGC CCCTGATTCC TCCATGAACC TGCAGCTCGG CCCAGATATG GTGTAAGAAG
24701   CTTGAGAGAT AGAACTGGGA GTGATCTGTG CCAGCAGGCA TTCAGCATGG AGTTGGCACT GGGGGTTGAA GTAGGGAATT TCCTTTGCTT
24801   GAAAGGGATC CCCCAACTTT CTTTTAAAAA TAGAATTTTA AAAACCTATT TTATTTTTGG CTCTGCTGGG TCTTCCTTGC TGTGCAGGCT TTTTCTCTAG
24901   TTGAGGCGAG TGGGGGCTAC TCTTTAGTTG CGGTGCCGAG GTTTCTCATG GCAGTGACTT TTGTTGTTGC AGAGCGTGGG CTCTAGGGCT AATGGCTTC
25001   AGCAGTTGCA GCTTCTGGGC TCTAGAGCAT AGGCTCAGTA GCTCCTTTAG ACAGGTTTAG TTGTTCCATG TTCTTCTTGA TCTTTCTTGCA ACAGGAATCA
25101   AACCCATGTC TCCTGCATTG GCAGGTGGAT TCTTTACCAT TGAGCCCCCA GGGAAGCCCC AGGATTCCTG TGGGAGTGTC CAGGAGAAGG
                                                                                        E19
25201   GCTGGCCTCA AGAGTCTGCT TTCTTTCCTT AGGCCCCAAG TGTACCCACC ACGCTCTCAC TCCATCCCCT CATATCCAGC CCTCCCCCGG GAAGAATCAG
                   E19
25301   TCAATATGTT GCCAGCCTTC CAGGAGCCTC CAGGAGTAAG TGGGGTCACC TCTGGGGAAT GGGTTGGGTC ACCCCCTGCA GTGGGGATTG GCACTTGTAT TTGTGAAGAG
25401   AGGCTCTTCA ATGAGAAAAG GGTGGCACAA AGCCAATGCC ACTTAACTCT TGTGTCTCTT CTGTCCACTC CATTGAGGTG TTAATAGTTA AGATCCGGGT TCAAATTCCA
25501   GCTCCACCAC TTGCTGACTT TGGGCAAGTT ACTTAACTCT AAAGCTCAAC ATGAACCCCA GCTCCTGGTA AGAGCTATGC CCTGCTTCAC AGGATTATTG
25601   TGAAGGTTAA TTTGAGTTAG TAATATGTAT TTACCTTGAT TTGTATATAT ATAGAACCCA GCTCCTGGTA AGAGCTATGC AAGTATTAGT ATTCTCTCTC CTGCCTCCTA
25701   AACCTACTGT CCTTTTTCTG CAGGACATCT TCCCCCCATA GGAGTTGAGG TGGAGGTGGG TGGAATAGAC AGCCAGAGTT TCCAGGTAGC ACTCAGGTGT
25801   TTACTGACTC TCAGTCAAAG CAGGACATCT TCCCCCCATA GGAGTTGAGG TGGAGGTGGG ATCGTAGAAC CAGGAGAGTT CAGAAATTAG CTAATGTATC
25901   CTTCCTCTGT CCCCGCTTC AGTCCCCAGT GCATATAATA ACATTTATAC AGAGAAGAGG ACCAAATTCA CAGGTAGAAA TGACTTGCCC AAGGTGATAC
26001   CATCAGGATG AGGAACTGGA AATAGTTTCC TTACTCAATG GGCTTGACTT TGCAACAGCT GCCCTGGACC AGCTTTCCTT TAACTGTACC CTCCTCTTCC
                         E20
26101   TGCTTCCAGA CCTCACCTGC CGATGCCTCC CAACCCTGAG CAGATGAGCC TGCCCTTTGA CCAACCTCAC CCGCAGTGAG TGACCACCCC CGCCCCCATC
26201   CTGAGCTCAA GCTCCTCATT CATTCCCAGC CTCAACCCCA CCCTGACCCC TCATTTACTT CTCTGGGGCT CTCTGGGGCT GGCAGGGGCC TGCTGCCGTG
```

FIG. 1l

```
                                                         SNP_25999_BT
                                                              |
26301  CCCACCTCAG GATCATGCTG TGTCCAGCCC TGAGCCCTTG CTCTGCTCAG A[N]GTGACCAT GGCAGAAGAC AGCTGCCTGA ACCAGCCGGT GGGAGGGTTC
26401  CCTCAAGGCA CCTGGTGAGT GTCAGCCTGG GGGTGGGGG TGGGCTGGGG GTTGCGGTGT GGGTACCATG CCTATCCCAC TGCTTCTCCA CTCCTCTCTG
                                                            E21/3'UTR
26501  CAGGGTCCGT GAAGACATGT TCCCGCCCTT GTTGCCTCCC ACTGAACAGA GCTTCTCTTG GAGGGACAAG GGGAGTCAGG GGGAGGGTCC
                                                            E21/3'UTR
26601  TTGGGACCCC AACCCCTCCT GCAGCCCTCC CCCTATGGGC AGTCTGGGAT CTCAATGTCC CACCTGGACC TAAGAGCTAA CCCCAGTTGG TGATCCCAGC
                                                            E21/3'UTR
26701  TGGAGACGGA GCCCAGAGAG ACCGCTCTCC TGCCCCCACG GGCCATCTGC CCCTGCTCCT GCCCAACAGC AGAGAGGGAG GGTGTGTCCT
                                                            E21/3'UTR
26801  CCTCTCCCCA CCCACTCCCT GCTCAGGAGG AAAAGACTGC CAGGAGAAGG TACACTGGGT GGAACATACC TACTCCTTCC CTTCCAACAC ACCCCTGCCC
                                                            E21/3'UTR
26901  TCTCCCTTCC AGATAGTGGA AGGGAAATTC AGGTTCCAAG TGAGACACGC CCCAACATGA CTGCACAGGC AGTGCACACG CATGTGTGTG TGCGTGCACG
                                                            E21/3'UTR
27001  CACATACACA CATACACACA CACATATACCA CACACAGAGC TCTCCTTGGA AGATGGCACT CAGCAGGAAG AGGGCTGGAC AAGAGCACAG GTGCGGGCAA
                                                            E21/3'UTR
27101  GAGGGGGATT TCTCCGCCTG CCCAAGCCA CTCACTGGTG GAAACACGCA CGCACGCACA CATCTGTTCC ACACACTGAG GATGGCGGTA
                                                            E21/3'UTR
27201  TGGGCTTAGG CCCCAGCCCT GGAGAGATGG GAAGCAGTTC AGGAGACCCT GGGAGGAAGG TGGGGTGGGG TCTGTACATT TGGTAACAGA TGTGGCTTTT
                                                            E21/3'UTR
27301  GCCCAGATTA AAAAAAAAGT CCCAACCAGC TCCAGATTCT TGTCAGTCAA CTGGAGACTT CAGGATACGT GTGCAGAAGT TCAAGGCTG
27401  AGTCTGTGTA CAGCCAGGTG AAAGCGCATG CACTTGGGAC ATGTAATATA TGGATGTCAC ACATGTTAGT TGTATGGCTT CATAGAACAT TGATCTCTCT
27501  GACTTTGCCT GTGTGACAAC ACAAGTTAGC AAGTATGAGA TACTGCACAC CAAGTATGCT AAGGCCCCAG CAAGTATGCT GGCCTCTCGG ACATATGCTA ACCCAAATGT
```

FIG. 2A

```
Cow     MSLWGLVSKMPPEKLQRLYVDFPQHLRHLLGDWLENQPWEFLVGSDTFCCNMASALLSAT
Horse   MSVWGLVLKMPPEKLQRLYVDFPQHLRHLLGDWLENQPWEFLVGSDAFCCNMASALLSAT
Dog     MSLWSLVSKMPPEKLQRLYVDFPQHLRHLLSDWLENQPWEFLVGSDTFCCNMASALLSAT
Human   MSLWGLVSKMPPEKVQRLYVDFPQHLRHLLGDWLESQPWEFLVGSDAFCCNLASALLSDT
Mouse   MSLWGLISKMSPEKLQRLYVDFPQRLRHLLADWLESQPWEFLVGSDAFCYNMASALLSAT
        **:*.*: **.***:*********:****.*** ***********:** *:****** *

Cow     VQRLQASAGEQGEGNTILQHISTLETIYQRDPLKLVATCRHILQGEKKAVMEQFHHLPMS
Horse   LQHLQTLAGEQGEGSAILQHISTLESIYQRDPLKLVATFKHILQGERKAVMEQFHHLPMP
Dog     VQRLQASAGKQGEGSTILQHISTLESIYQRDPLKLVATFRQILQGEKKAVMEQFRHLPMP
Human   VQHLQASVGEQGEGSTILQHISTLESIYQRDPLKLVATFRQILQGEKKAVMEQFRHLPMP
Mouse   VQRLQATAGEQGKGNSILPHISTLESIYQRDPLKLVATIRQILQGEKKAVIEEFRHLPGP
        :*:**: .*:**:*.:** ****** *:********** ::****:***:***:*** .

Cow     FHWKQEELKFNTVLRRLQHRAGETRLLREALQPGAEAGQVSLHSLIETPTNGTGPSEALV
Horse   FHRKQEELKFNTVLRRLQHRVGETRLLREALKQGAEAGQVSLHSLIETPANGSGPSEALA
Dog     FHWKQEELKFNTALQRLQHRVGETRLLREALQPGAEAGQVSLRSLIDAPANGTGPREALA
Human   FHWKQEELKFKTGLRRLQHRVGEIHLLREALQKGAEAGQVSLHSLIETPANGTGPSEALA
Mouse   FHRKQEELKFTTALGRLQHRVRETRLLRESLQQGAKTGQVSLQNLIDPPVNGPGPSEDLA
        ** *******.* * *****. * :****:*:  **::*****:.**:.*.**.** * *.

Cow     TLLQETVGELEAAQALVLKRIQIWKRQQQLAGNGAPFEESLAPLQERCESLVDIYSQLQQ
Horse   TLLQEAVAELEAAQALVLKRIQIWKRQQQLAGNGAPFEESLASLQERCESLVDIYSQLQQ
Dog     TLLQETVGELEAAQALVLKRIQIWKRQQQLAGNGAPFEESLAPLQERCESLVDIYSQLQQ
Human   MLLQETTGELEAAKALVLKRIQIWKRQQQLAGNGAPFEESLAPLQERCESLVDIYSQLQQ
Mouse   TMLQGTVGDLEATQALVLKRIQIWKRQQQLAGNGTPFEESLAGLQERCESLVEIYSQLQQ
        :**  :..:***::******************:****** ***********:*******

Cow     EVGAAGGELDPKTRAALISRLDEVLRTLVTSSFLVEKQPPQVLKTQTKFQAGVRFLLGLR
Horse   EVGAAGGELEPKTRAVLISRLEEVLRTLVTSSFLVEKQPPQVLKTQTKFQAGVRFLLGLR
Dog     EVGAAGGELEPKARAVLSSRLDEVLRSLVTSSFLVEKQPPQVLKTQTKFQAGVRFLLGLR
Human   EVGAAGGELEPKTRASLTGRLDEVLRTLVTSCFLVEKQPPQVLKTQTKFQAGVRFLLGLR
Mouse   EIGAASGELEPKTRASLISRLDEVLRTLVTSSFLVEKQPPQVLKTQTKFQAGVRFLLGLQ
        *:***.***:**:** *  .**:****:****.***************************:

Cow     FLGAPAKPPLVRADMVTEKQARELSMPQGPGAGAESTGEIINNTVPLENSIPGNCCSALF
Horse   FLGAPAKPPVVRADMVTEKQARELSMPQGPGAGTESSGEIINNTVPLENSIPGNCCSALF
Dog     FLGAPAKPPLVRADMVTEKQARELSMPQGPGAGAESTGEIINNTVALENSIPGNCCSALF
Human   FLGAPAKPPLVRADMVTEKQARELSVPQGPGAGAESTGEIINNTVPLENSIPGNCCSALF
Mouse   FLGTSAKPPMVRADMVTEKQARELSLAQGPGTGVESTGEIMNNTVPLENSIPSNCCSALF
        ***:.****:*************** .****:*.***:****.******.*******

Cow     KNLLLKKIKRCERKGTESVTEEKCAVLFSTSLTLGPNKLPIQLQALSLPLVVIVHGNQDN
Horse   KNLLLKKIKRCERKGTESVTEEKCAVLFSTSFALGPNKLHIQLQALSLPLVVIVHGNQDN
Dog     KNLLLKKIKRCERKGTESVTEEKCAVLFSTSLALGPNKLPVQLQALSLPLVVIVHGNQDN
Human   KNLLLKKIKRCERKGTESVTEEKCAVLFSASFTLGPGKLPIQLQALSLPLVVIVHGNQDN
Mouse   KNLLLKKIKRCERKGTESVTEEKCAVLFSTSFTLGPNKLLIQLQALSLPLVVIVHGNQDN
        *****************************:*:::***.** :*****************

Cow     NAKATILWDNAFSEMDRVPFVVAERVPWEKMCETLNLKFMAEVGTNRGLLPEHFLFLAQK
Horse   NAKATILWDNAFSEMDRVPFVVAERVPWEKMCETLNLKFMAEVGTNRGLLPEHFLFLAQK
Dog     NAKATILWDNAFSEMDRVPFVVAERVPWEKMCETLNLKFMAEVGTNRGLLPEHFLFLAQK
Human   NAKATILWDNAFSEMDRVPFVVAERVPWEKMCETLNLKFMAEVGTNRGLLPEHFLFLAQK
Mouse   NAKATILWDNAFSEMDRVPFVVAERVPWEKMCETLNLKFMAEVGTSRGLLPEHFLFLAQK
        *********************************************.*************

Cow     IFNDNSLSIEAFQHRSVSWSQFNKEILLGRGFTFWQWFDGVLDLTKRCLRSYWSDRLIIG
Horse   IFNDNSLSTEAFQHRSVSWSQFNKEILLGRGFTFWQWFDGVLDLTKRCLRSYWSDRLIIG
Dog     IFNDNSLSMEAFQHRSVSWSQFNKEILLGRGFTFWQWFDGVLDLTKRCLRSYWSDRLIIG
Human   IFNDNSLSMEAFQHRSVSWSQFNKEILLGRGFTFWQWFDGVLDLTKRCLRSYWSDRLIIG
Mouse   IFNDNSLSVEAFQHRCVSWSQFNKEILLGRGFTFWQWFDGVLDLTKRCLRSYWSDRLIIG
        ******** *****.*********************************************
```

*FIG. 2B*

```
Cow     FISKQYVTSLLLNEPDGTFLLRFSDSEIGGITIAHVIRGQDGSPQIENIQPFSAKDLSIR
Horse   FISKQYVTSLLLNEPDGTFLLRFSDSEIGGITIAHVIRGQDGSSQIENIQPFSAKDLSIR
Dog     FISKQYVTSLLLNEPDGTFLLRFSDSEIGGITIAHVIRGQDGSPQIENIQPFSAKDLSIR
Human   FISKQYVTSLLLNEPDGTFLLRFSDSEIGGITIAHVIRGQDGSPQIENIQPFSAKDLSIR
Mouse   FISKQYVTSLLLNEPDGTFLLRFSDSEIGGITIAHVIRGQDGSSQIENIQPFSAKDLSIR
        ************************************************.***********

Cow     SLGDRIRDLAQLKNLYPKKPKDEAFRSHYKPEQMGKDGRGYVPATIKMTVERDQPLPTPE
Horse   SLGDRIRDLAQLKNLYPKKPKDEAFRSHYKPEQMGKDGRGYVPATIKMTVERDQPLPTPE
Dog     SLGDRIRDLAQLKNLYPKKPKDEAFRSHYKPEQMGKDGRGYVPATIKMTVERDQPLPTLE
Human   SLGDRIRDLAQLKNLYPKKPKDEAFRSHYKPEQMGKDGRGYVPATIKMTVERDQPLPTPE
Mouse   SLGDRIRDLAQLKNLYPKKPKDEAFRSHYKPEQMGKDGRGYVSTTIKMTVERDQPLPTPE
        *********************************************.************ *

Cow     PQMPTMVPSYDLGMAPDSSMNLQLGPDMVPQVYPPRSHSIPSYPALPREESVNMLPAFQE
Horse   PQMPTMMPTYDLGMAPDSSMNMQLGPDMVPQVYPPHSHSMPSYQGLSREESVSVLPAFPE
Dog     PQMPTMVPTYDLGMATESSMNMQLSPDMVSQVYPPHSHSMPSFQALSRED---VLPTFQE
Human   LQMPTMVPSYDLGMAPDSSMSMQLGPDMVPQVYPPHSHSIPPYQGLSPEESVNVLSAFQE
Mouse   PQMPAMVPPYDLGMAPDASMQLSSDMGYPPQSIHS---------FQSLEESMSVLPSFQE
        ***:*:*.******.::**.:. . . .*  .       . *:   :*.:* *

Cow     PHLPMPPNLSQMSLPFDQPHPQGLLPCPPQDHAVSSPEPLLCSDVTMAEDSCLNQPVGGF
Horse   PHLPMPPTLSQMSLPFDQPHPQGLLPCQPQEHAVSSPEPLLCSDVTMAEESCLSQPVGGF
Dog     SHLQMPPNLSQINLPFDQPHPQGLLPCQSQEHAVSTPEPLLCSDVPMTEDSCLSQPVGGF
Human   PHLQMPPSLGQMSLPFDQPHPQGLLPCQPQEHAVSSPDPLLCSDVTMVEDSCLSQPVTAF
Mouse   PHLQMPPNMSQITMPFDQPHPQGLLQCQSQEHAVSSPEPMLCSDVTMVEDSCLTQPVGGF
        .** ***.::*:.:***********  * .*:****:*:*:*****.*.*:***.*** .*

Cow     PQGTWVREDMFPPLLPPTEQDLTKLLLEGQGESGGGSLGPQPLLQPSPYGQSGISMSHLD
Horse   PQGTWVSEDMFPPLLPPTEQDLTKLLLEGQGESGGGSLGAQPLLQPSPYGQSGISMSHLD
Dog     PQGSTWVGEDMFPPLLPPTEQDLTKLLLEGQGESGGGSLGTQPLLQPSHYGQSGISMSHLD
Human   PQGTWIGEDIFPPLLPPTEQDLTKLLLEGQGESGGGSLGAQPLLQPSHYGQSGISMSHMD
Mouse   PQGTWVSEDMYPPLMPPTEQDLTKLLLENQGEAGG-SLGSQPLLQPSPYGQSGISLSHLD
        **.**: **.:***:*************. ***:** ***.******* ******:**:*

Cow     LRANPSW
Horse   LRANPSW
Dog     LRANPSW
Human   LRANPSW
Mouse   LRTNPSW
        **:****
```

STAT6 EFFECTS ON LIVESTOCK ANIMAL GROWTH

FIELD OF THE INVENTION

The present application provides methods and compositions for using polymorphisms in the STAT6 gene that are associated with economically important feedlot and carcass traits in livestock animals.

BACKGROUND OF THE INVENTION

The cost of feeding is the single largest variable cost in beef production systems, accounting for approximately 70% of the total production cost (Perry and Cecava, 1995, *Beef Cattle Feeding and Nutrition*, 2nd Ed., Academic Press, San Diego, Calif.). Generally, about 70-75% of the total dietary energy consumed in a beef production system is used for maintenance (Ferrell and Jenkins 1984, *J. Anim. Sci.* 58:234-243; NRC (National Research Council) 1996, *Nutrient Requirements of Beef Cattle*, Seventh Reviewed Edition, Washington, D.C.: National Academy Press). This means higher beef production costs, especially in large-sized breeding animals due to presumably higher maintenance energy needs, lower overall production system efficiency, and therefore lower profits. Indeed, compared to swine and poultry, which are able to convert about 14 and 22%, respectively, of the total energy intake into protein deposition, only 5% of the total energy intake in beef cattle is converted into deposited protein. Improvements in the efficiency of feed utilization by beef cattle would therefore lead to better economic returns from both beef cattle breeding operations and feedlots (Gibb and McAllister, 1999, "The impact of feed intake and feeding behaviour of cattle on feedlot and feedbunk management," Pages 101-116. D. Korver and J. Morrison (ed). Proc. 20th Western Nutr. Conf. Canada; Liu et al., 2000, *Can. J. Anim. Sci.* 80:435-441; Herd et al., 2003, *J. Anim. Sci.* 81(E. Suppl. 1):E9-E17). According to Johnson et al. (2003) *J. Anim. Sci.* 2003. 81:E27-E38, the reasons for the lack of change in beef cattle energetic efficiency, despite several years of intensive production, include the lack of a consistent selection goal, loose and inconsistent definitions of efficiency, concentration on output traits, and emphasis on population similarities rather than individual variation.

Efficient beef cattle production involves a complex summation of appropriate levels of available feed inputs and product outputs over a range of different production systems involving animals at different developmental stages. Thus, several indices have been proposed for determining the energetic efficiency of beef production, as comprehensively reviewed by Archer, et al. (1999) *Australian Journal of Agricultural Research* 50:147-161. These include feed conversion ratio (FCR), maintenance efficiency, partial efficiency of growth (PEG), cow-calf efficiency, and residual feed intake (RFI). Two other indices are relative growth rate (growth relative to instantaneous body size) and Kleiber ratio (weight gain per unit metabolic body size).

Traditionally, feed efficiency has been expressed in terms of FCR, or its inverse (gross feed efficiency, GFE). This is usually measured as the ratio of feed consumed to gain in weight. It reflects the efficiency of use of the energy consumed for maintenance and growth and captures the relationship between input of feed and output of product (Herd et al., 2003, supra). Though FCR has been in existence for many years, it is difficult to improve through direct selection because it is difficult to measure on the individual and its genetic correlation with growth rate implies that selection for it can lead to an increase in body weight (BW) and feed intake, which is not always desirable (Gunsett, 1984, *J. Anim. Sci.* 59: 1185-1193; Archer et al., 1999, supra; Crews, 2005, *Genet. Mol. Res.* 4 (2): 152-165). On the other hand, several studies in different species have demonstrated considerable phenotypic and genetic variations among individual animals in feed intake above and below the predicted requirements for maintenance and growth (Foster et al., 1983, *Anim. Prod.* 37:387-393; Luiting and Urff, 1991, *Poult. Sci.* 70:1663-1672; Archer et al., 1998, *Anim. Sci.* 67:171-182; Archer et al., 1999, supra). This variation in intake is usually measured as RFI, and was first proposed for use in cattle by Koch et al. (1963) *J. Anim. Sci.* 22:486-494.

Ultimately, the resulting phenotypic information collected using automated feed intake monitoring systems could be employed to dissect the molecular architecture of several economically relevant, but complex traits (ERT) in beef cattle. Molecular techniques can be employed to detect and map the chromosomal locations of genes contributing to variation in growth, feed intake, energetic efficiency, feeding behavior, and carcass merit. Several molecular tools and approaches, as well as statistical and computational techniques, are available that can be employed to quantify the number(s), location(s) and effect(s) of quantitative trait loci (QTL) through the use of genotypic information from genetic markers that are evenly spaced along chromosomes in the genome. A QTL is defined as the chromosomal location of individual or groups of genes, of unknown primary function, that show(s) significant association with a complex trait of interest (Lander and Kruglyuak, 1995, *Natural Genet* 11: 241-247). In beef cattle, QTL have been detected for disease tolerance (Hanotte et al., 2003, *PNAS Agricultural Sciences* 100:7443-7448), fertility and reproductive performance (Kirkpatrick et al., 2000, *Mammalian Genome* 11:136-139), body conformation (Grobet et al., 1998, *Mammalian Genome* 9: 210-213), birth weight and growth performance (Davis et al., 1998, *Proc. 6th World Congr. Genet. Appl. Livest. Prod.* 23: 441-444; Casas et al., 2003, *J. Anim. Sci.* 81, 2976-83; Li et al., 2002, *J. Anim. Sci.* 80:1187-1194; Kim et al., 2003, *J. Anim. Sci* 81, 1933-42), and carcass and meat quality (Keele et al., 1999, *J. Anim. Sci* 77, 1364-1371; Casas et al., 2000, *J. Anim. Sci.* 78:560-569; MacNeil and Grosz, 2002, *J. Anim. Sci.* 80:2316-2324; Casas et al., 2003, supra; Kim et al., 2003, supra; Moore et al., 2003, *J. Anim. Sci.* 81:1919-1925; and Li et al., 2004, *J. Anim Sci.* 2004 82: 967-972).

It is possible to search for and identify associations between polymorphisms in specific candidate genes and measures of variation in feed intake, feed efficiency and feeding behavior. A candidate gene may be selected based on previously known biochemical or physiological information or may be chosen because it maps to or close to the location of a QTL (positional candidate gene). Of interest among these candidates are genes shown to affect feed intake, behavior, energy balance, and body composition, such as the appetite regulating gene leptin. Several polymorphisms in candidate genes have been shown to be associated with economically relevant traits in cattle (Chrenek et al., 1998, *Czech Journal of Animal Science* 43, 541-544; Barendse et al., 2001, "The TG5 DNA marker test for marbling capacity in Australian feedlot cattle," on the worldwide web at beef.crc.org.au/Publications/MarblingSym/Day1/Tg5DNA; Ge et al., 2001, *J. Anim. Sci.* 79:1757-1762; Grisart et al., 2002, *Genome Research* 12:222-231; Buchanan et al., 2002; *Genet. Sel. Evol.* 34:105-116; Moore et al., 2003, *J. Anim. Sci.* 81:1919-1925; Li et al., 2004, supra; and Nkrumah et al., 2005, *J. Anim. Sci.* 83:20-28).

The bovine microsatellite ETH10, located on bovine chromosome 5, has recently been associated with marbling (deposition of intramuscular fat) in Asian breeds of cattle (Smith et al. 2001, *J. Animal Sci* 79:3041-51; and U.S. Pat. No. 6,383, 751 ("the '751 patent")). The '751 patent suggests that differences in marbling score, between related cattle with different ETH10 genotypes, is likely due to a closely linked gene. The '751 patent proposes that retinol dehydrogenase (11-cis and 9-cis) (RDH5), which maps 1.01 centi-rads (cR) from ETH10 on the bovine radiation hybrid map (Womack et al. 1997, *Mamm Genome* 8:854-6), was the responsible gene. The association between ETH10 and marbling was highly significant with a P-value of <0.00015. Even though strong linkage disequilibrium would exist in the population tested, a P-value of this magnitude suggests that the gene responsible might be more closely linked to ETH 10 than RDH5.

Using a bioinformatics-based method to identify sequence homologies between bovine microsatellites and gene sequences from other species, it was demonstrated that ETH10 was putatively located within the 5' UTR of the bovine STAT6 gene (Farber and Medrano, 2003, *Animal Genetics* 34:11-18). To support the location of ETH10, a bovine sequence tagged site (STS) in the 3' UTR of bovine STAT6 was designed from available EST sequences.

STAT6 is the principal transcription factor involved in interlukin-4 (IL-4) and IL-13 signaling (Takeda et al. 1997, *J Mol Med* 75:317-326). In this context, a polymorphic microsatellite (homologous to ETH10) in the first exon of human STAT6 has been associated with predisposition to allergic diseases, due to altered IL-4 and IL-13 signal transduction (Tamura et al. 2001, *Clinical and Experimental Allergy* 31:1509-1514). More importantly, STAT6 has been shown to be activated by the full length form and not the truncated form of the leptin receptor in cell culture, implicating it as a potential mediator of the anti-obesity effects of leptin (Ghilardi et al. 1996, *Proc Natl Acad Sci USA* 93:6231-6235). As a mediator of leptin signaling, different allelic forms of STAT6 could impact the level of circulating leptin, which would have a direct impact on the mass of adipocytes (Maffei et al. 1995, *Nature Med* 1:1155-61).

The present invention provides SNPs within the STAT6 gene that are correlated with economically important feedlot and carcass traits in livestock animals.

BRIEF SUMMARY OF THE INVENTION

A variety of characteristics of livestock animals are considered important in determining the overall value of the finished product. Some factors are involved in the palatability of the meat produced, which is important to consumers, and which is reflected in the grading system used to classify meat. Still other factors affect the cost of producing an animal of given size and therefore affect the cost of meat that the consumer will ultimately pay, and which will result in improved profitability for producers of livestock as well as the operators of feedlots. As a result, methods of production that can improve the quality, or reduce the cost of production are desirable for all concerned in the production and consumption of meat from livestock.

The present invention is based in part on the discovery of SNPs that are associated with a variety of parameters related to carcass and feedlot traits of livestock animals. Knowledge of the STAT6 genotype of livestock animals permits the development of genetic testing methods such that animals with the most desirable characteristics with regard to carcass weight and fat distribution, average daily weight gain and rib eye area can be identified and selected. This in turn leads to the development of methods of livestock management, wherein a higher degree of predictability about the eventual development of livestock animals becomes possible, once the genotype of animals with regard to the STAT6 gene is determined.

Accordingly, the present inventions provides compositions and methods for using SNPs in the STAT6 gene to identify livestock animals (e.g., *Bos*, bovines) with desirable feedlot and carcass traits. In one aspect, the invention provides methods of selecting individual livestock animals, e.g., bovines, with desirable traits based on the knowledge of the animal's STAT6 genotype. In some embodiments, the methods comprise the steps of: determining the STAT6 alleles of the animal, e.g., bovine, at one or more SNP IDs selected from the group consisting of 14636, 16084 and 19597 of a gene encoding STAT6; wherein the traits are selected from the group consisting of back fat, calculated yield grade, cutability, hot carcass weight, dry matter intake, days on feed, back fat rate and average daily gain, wherein:

i) a "CC" genotype at SNP ID 16084 is indicative of decreased back fat, a lower calculated yield grade, and increased cutability in comparison to an "AC" or "AA" genotype;

ii) an "AA" genotype at SNP ID 19597 is indicative of increased hot carcass weight, increased dry matter intake and fewer days on feed in comparison to a "AG" or "GG" genotype;

iii) a "CC" genotype at SNP ID 14636 is indicative of increased back fat rate, fewer days on feed, and increased average daily gain in comparison to a "CG" or "GG" genotype. In some embodiments, the methods further comprise the step of selecting the livestock animal with the desirable trait based on the animal's STAT6 genotype.

In another aspect, the invention provides methods for distinguishing bovines having one or more STAT6 gene polymorphisms. In some embodiments, the methods comprise a) amplifying one or more regions or alleles of the bovine STAT6 gene using an oligonucleotide pair to form nucleic acid amplification products comprising amplified STAT6 gene polymorphism sequences;

b) detecting one or more polymorphisms present in the bovine STAT6 gene at a SNP ID selected from the group consisting of 14636; 16084 and 19597; and c) analyzing the one or more polymorphisms, wherein i) a "CC" genotype at SNP ID 16084 is indicative of decreased back fat, a lower calculated yield grade, and increased cutability in comparison to an "AC" or "AA" genotype;

ii) an "AA" genotype at SNP ID 19597 is indicative of increased hot carcass weight, increased dry matter intake and fewer days on feed in comparison to a "AG" or "GG" genotype; and iii) a "CC" genotype at SNP ID 14636 is indicative of increased back fat rate, fewer days on feed, and increased average daily gain in comparison to a "CG" or "GG" genotype.

With respect to the methods for identifying animals with desirable feedlot or carcass traits based on their STAT6 genotype, in some embodiments, the step of determining or analyzing comprises determining the STAT6 allele of the animal at SNP ID 14636, wherein a "CC" genotype at SNP ID 14636 is indicative of increased back fat rate, fewer days on feed, and increased average daily gain in comparison to a "CG" or "GG" genotype. In some embodiments, the step of determining or analyzing comprises determining the STAT6 allele of the animal at SNP ID 16084, wherein a "CC" genotype at SNP ID 16084 is indicative of decreased back fat, a lower calculated yield grade, and increased cutability in comparison to an "AC" or "AA" genotype. In some embodiments, the step of determining or analyzing comprises determining the STAT6 allele of the animal at SNP ID 19597, wherein an "AA" genotype at SNP ID 19597 is indicative of increased hot carcass weight, increased dry matter intake and fewer days on feed in comparison to a "AG" or "GG" genotype.

In some embodiments, the livestock animal is from the genus *Bos*. In some embodiments, the livestock animal is a bovine. In some embodiments, the livestock animal is a *Bos taurus*. In some embodiments, the livestock animal is a *Bos indicus*.

In some embodiments, two or more polymorphisms are determined, e.g., are amplified. In some embodiments, one, two or three polymorphisms are determined, e.g., are amplified.

In some embodiments, the gene encoding bovine STAT6 shares at least 95% sequence identity to SEQ ID NO:1 or the complement thereof.

In some embodiments, the SNP ID 14636 of the gene encoding STAT6 is within a nucleic acid sequence having at least 95% sequence identity to a nucleic acid sequence of SEQ ID NO:2. In some embodiments, the SNP ID 16084 of the gene encoding STAT6 is within a nucleic acid sequence having at least 95% sequence identity to a nucleic acid sequence of SEQ ID NO:3. In some embodiments, the SNP ID 19597 of the gene encoding STAT6 is within a nucleic acid sequence having at least 95% sequence identity to a nucleic acid sequence of SEQ ID NO:4.

In some embodiments, the STAT6 alleles are independently detected by an amplification reaction using polynucleotides that distinguish between alleles at SNP IDs 14636, 16084 or 19597.

In some embodiments, the amplification reaction is selected from the group consisting of polymerase chain reaction (PCR), strand displacement amplification (SDA), nucleic acid sequence based amplification (NASBA), rolling circle amplification (RCA), T7 polymerase mediated amplification, T3 polymerase mediated amplification and SP6 polymerase mediated amplification.

In some embodiments, the STAT6 alleles are independently detected by hybridization using polynucleotides that distinguish between alleles at SNP IDs 14636, 16084 or 19597.

In some embodiments, the STAT6 alleles are independently detected by sequencing a subsequence of a gene encoding STAT6, the subsequence comprising SNP IDs 14636, 16084 or 19597.

In some embodiments, the polymorphism or allele or position of the bovine STAT6 gene is at SNP ID 14636, and the oligonucleotide pair comprises a forward primer comprising a nucleic acid sequence selected from 5'-GCTGGTCACTCT-TCCTAATC-3' (SEQ ID NO:11) and 5'-TCTGACTTAGG-GATCACCTC-3' (SEQ ID NO:12); and a reverse primer comprising a nucleic acid sequence selected from 5'-GAC-CTCTATCTCTACCCTAC-3' (SEQ ID NO:13); 5'-ACCTC-TATCTCTACCCTACG-3' (SEQ ID NO:14) and 5'-CTC-TACCCTACGGGGAC-3' (SEQ ID NO:15).

In some embodiments, the polymorphism or allele or position of the bovine STAT6 gene is at SNP ID 16084, and the oligonucleotide pair comprises a forward primer comprising a nucleic acid sequence selected from 5'-TTTCCCTACTGC-CCCATTGC-3' (SEQ ID NO:16); 5'-TCAGAGAGCTTTC-CCTACTG-3' (SEQ ID NO:17); and 5'-CCTGTCTCTTAC-CCTCT-3' (SEQ ID NO:18); and a reverse primer comprising the nucleic acid sequence 5'-TAATGGAGTGGGAA-GAGCTG-3' (SEQ ID NO:19).

In some embodiments, the polymorphism or allele or position of the bovine STAT6 gene is at SNP ID 19597, and the oligonucleotide pair comprises a forward primer comprising a nucleic acid sequence selected from 5'-CACACTCGT-CACCAGGTATG-3' (SEQ ID NO:20) and 5'-GAGC-CCCCCTGCCTG-3' (SEQ ID NO:21); and a reverse primer comprising a nucleic acid sequence selected from 5'-AACTCTGACCCTCCTGTTTC-3' (SEQ ID NO:22) and 5'-GGGGTCTGCTCTCCA-3' (SEQ ID NO:23).

In a related aspect, the invention provides methods of distinguishing a *Bos taurus* from a *Bos indicus* based on one or more polymorphisms in a bovine STAT6 gene. In some embodiments, the methods comprise:

determining one or more STAT6 alleles of a bovine at one or more SNP IDs selected from the group consisting of 10922, 14257, 24000 and 25999 of a bovine gene encoding STAT6, wherein:
  i) an "AA" genotype at SNP ID 10922 indicates that the bovine is a *Bos taurus*, and a "GG" genotype at SNP ID 10922 indicates that the bovine is a *Bos indicus*;
  ii) a "CC" genotype at SNP ID 14257 indicates that the bovine is a *Bos taurus*, and a "AA" genotype at SNP ID 14257 indicates that the bovine is a *Bos indicus*;
  iii) a "TT" genotype at SNP ID 24000 indicates that the bovine is a *Bos taurus*, and a "CC" genotype at SNP ID 24000 indicates that the bovine is a *Bos indicus*; and
  iv) a "TT" genotype at SNP ID 25999 indicates that the bovine is a *Bos taurus*, and an "CC" genotype at SNP ID 25999 indicates that the bovine is a *Bos indicus*.

In some embodiments, the methods of distinguishing a *Bos taurus* from a *Bos indicus* based on one or more polymorphisms in a bovine STAT6 gene comprise:
  a) amplifying one or more alleles of the bovine STAT6 gene using an oligonucleotide pair to form nucleic acid amplification products comprising amplified STAT6 gene polymorphism sequences;
  b) detecting one or more polymorphisms present in the bovine STAT6 gene at a SNP ID selected from the group consisting of 10922, 14257, 24000 and 25999; and
  c) analyzing the one or more polymorphisms, wherein
    i) an "AA" genotype at SNP ID 10922 indicates that the bovine is a *Bos taurus*, and a "GG" genotype at SNP ID 10922 indicates that the bovine is a *Bos indicus*;
    ii) a "CC" genotype at SNP ID 14257 indicates that the bovine is a *Bos taurus*, and a "AA" genotype at SNP ID 14257 indicates that the bovine is a *Bos indicus*;
    iii) a "TT" genotype at SNP ID 24000 indicates that the bovine is a *Bos taurus*, and a "CC" genotype at SNP ID 24000 indicates that the bovine is a *Bos indicus*; and
    iv) a "TT" genotype at SNP ID 25999 indicates that the bovine is a *Bos taurus*, and an "CC" genotype at SNP ID 25999 indicates that the bovine is a *Bos indicus*.

With respect to the embodiments of the methods of distinguishing a *Bos taurus* from a *Bos indicus* based on polymorphisms in the STAT6 gene, in some embodiments two or more polymorphisms are determined, e.g., are amplified. In some embodiments, two, three, or four polymorphisms are determined, e.g., are amplified.

In some embodiments, the polymorphism or allele or position of the bovine STAT6 gene is at SNP ID 10922, and the oligonucleotide pair comprises a forward primer comprising a nucleic acid sequence selected from 5'-TGTGATGGGT-TGAACTCTGC-3' (SEQ ID NO:24) and 5'-CTGCCTCT-CAAAAATTTATATATTA-3' (SEQ ID NO:25); and a reverse primer comprising a nucleic acid sequence selected from 5'-GGGTACCTCCTATGAATATG-3' (SEQ ID NO:26) and 5'-GGGATATGTGATTTCAACATA-3' (SEQ ID NO:27).

In some embodiments, the polymorphism or allele or position of the bovine STAT6 gene is at SNP ID 14257, and the oligonucleotide pair comprises a forward primer comprising a nucleic acid sequence selected from 5'-GGGCCTCTGAC-TACCAATGT-3' (SEQ ID NO:9); 5'-TTTTTCCACACAC-CCCATCC-3' (SEQ ID NO:28); and 5'-GGGACGTGT-TAAGGC-3' (SEQ ID NO:29); and a reverse primer comprising a nucleic acid sequence selected from 5'-CCA-CACCCTTGAAGAGGAAC-3' (SEQ ID NO:10); 5'-ACT-TCCCCCCAACCCAGAG-3' (SEQ ID NO:30) and 5'-TTGCCCTCCTTCCCC-3' (SEQ ID NO:31). In some embodiments, the polymorphism or allele or position of the bovine STAT6 gene is at SNP ID 14257, and the oligonucleotide pair comprises forward primer 5'-GGGCCTCTGAC-TACCAATGT-3' (SEQ ID NO:9) and reverse primer 5'-CCA-CACCCTTGAAGAGGAAC-3' (SEQ ID NO:10).

In some embodiments, the polymorphism or allele or position of the bovine STAT6 gene is at SNP ID 24000, and the oligonucleotide pair comprises a forward primer comprising a nucleic acid sequence selected from 5'-TCATTTCCCT-GCTTCTGGAC-3' (SEQ ID NO:32) and 5'-CCATCATC-CATGCTCACCTTTTC-3' (SEQ ID NO:33); and a reverse primer comprising a nucleic acid sequence selected from 5'-ATGGAATGCTTCCGGGTTAG-3' (SEQ ID NO:34) and 5'-AGGGAGGAAGGGAGCT-3' (SEQ ID NO:35).

In some embodiments, the polymorphism or allele or position of the bovine STAT6 gene is at SNP ID 25999, and the oligonucleotide pair comprises a forward primer comprising a nucleic acid sequence selected from 5'-CCTCAGGATCAT-GCTGTGTC-3' (SEQ ID NO:36) and 5'-CCCTTGCTCT-GCTCAGA-3' (SEQ ID NO:37); and a reverse primer comprising a nucleic acid sequence selected from 5'-TGGTTCAGGCAGCTGTCTTC-3' (SEQ ID NO:38) and 5'-TTCTGCCATGGTCAC-3' (SEQ ID NO:39).

In some embodiments, the polymorphism detected is a restriction fragment length polymorphism.

In some embodiments, the amplification reaction is selected from the group consisting of polymerase chain reaction (PCR), strand displacement amplification (SDA), nucleic acid sequence based amplification (NASBA), rolling circle amplification (RCA), T7 polymerase mediated amplification, T3 polymerase mediated amplification and SP6 polymerase mediated amplification.

In some embodiments, the bovine STAT6 gene shares at least 95% sequence identity to SEQ ID NO:1 or the complement thereof.

In some embodiments, the SNP ID 10922 of the gene encoding STAT6 is within a nucleic acid sequence having at least 95% sequence identity to a nucleic acid sequence of SEQ ID NO:5. In some embodiments, the SNP ID 14257 of the gene encoding STAT6 is within a nucleic acid sequence having at least 95% sequence identity to a nucleic acid sequence of SEQ ID NO:6. In some embodiments, the SNP ID 24000 of the gene encoding STAT6 is within a nucleic acid sequence having at least 95% sequence identity to a nucleic acid sequence of SEQ ID NO:7. In some embodiments, SNP ID 25999 of the gene encoding STAT6 is within a nucleic acid sequence having at least 95% sequence identity to a nucleic acid sequence of SEQ ID NO:8.

In a related aspect, the invention provides isolated polynucleotides for distinguishing the STAT6 SNP IDs 10922, 14257, 14636, 16084, 19597, 24000 and 25999.

In some embodiments, the isolated polynucleotides distinguish STAT6 alleles at SNP ID 14257. In some embodiments, the isolated polynucleotide is SEQ ID NO:9. In some embodiments, the isolated polynucleotide is SEQ ID NO:10.

Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization described below are those well known and commonly employed in the art. Standard techniques are used for nucleic acid and peptide synthesis. Generally, enzymatic reactions and purification steps are performed according to the manufacturer's specifications. The techniques and procedures are generally performed according to conventional methods in the art and various general references (see generally, Sambrook et al. MOLECULAR CLONING: A LABORATORY MANUAL, 3rd ed. (2001) Cold Spring Harbor Laboratory Press, Cold Spring Harbor, N.Y. and Ausubel, ed., Current Protocols in Molecular Biology, 1990-2008, John Wiley Interscience), which are provided throughout this document. The nomenclature used herein and the laboratory procedures in analytical chemistry, and organic synthetic described below are those well known and commonly employed in the art. Standard techniques, or modifications thereof, are used for chemical syntheses and chemical analyses.

STAT6 refers to nucleic acids and polypeptide polymorphic variants (including single nucleotide polymorphisms involving displacement, insertion, or deletion of a single nucleotide that may or may not lead to a change in an encoded polypeptide sequence), alleles, mutants, and interspecies homologs that: (1) have an amino acid sequence that has greater than about 90% amino acid sequence identity, for example, 91%, 92%, 93%, 94%, 95%, 96%, 97%, 98% or 99% or greater amino acid sequence identity, preferably over a region of at least about 25, 50, 100, 200, 500, 1000, or more amino acids, or over the full-length, to an amino acid sequence encoded by a STAT6 nucleic acid (see, e.g., SEQ ID NO:1 and GenBank Accession Nos. AB038383 (Bos taurus); NC_009149 (Equus caballus); BV726713 (Sus scrofa); EU439612.1 (Canis lupus); NM_001012930 (Gallus gallus)) or to an amino acid sequence of a STAT6 polypeptide (e.g., GenBank Accession Nos. BAA96475 (Bos taurus); ACA21821 (Canis lupus); and NP_001012948 (Gallus gallus); (2) bind to antibodies, e.g., polyclonal antibodies, raised against an immunogen comprising an amino acid sequence of a STAT6 polypeptide (e.g., encoded by a nucleic acid sequence of SEQ ID NO:1 or a nucleic acid of GenBank Accession Nos. AB038383; NC_009149; BV726713; EU439612.1; and NM_001012930; or an amino acid sequence of GenBank Accession Nos. BAA96475; ACA21821; and NP_001012948), and conservatively modified variants thereof, (3) specifically hybridize under stringent hybridization conditions to an anti-sense strand corresponding to a nucleic acid sequence encoding a STAT6 protein, and conservatively modified variants thereof, (4) have a nucleic acid sequence that has greater than about 95%, preferably greater than about 96%, 97%, 98%, 99%, or higher nucleotide sequence identity, preferably over a region of at least about 25, 50, 100, 200, 500, 1000, or more nucleotides, or over the full-length, to a STAT6 nucleic acid. STAT6 nucleic acids include polynucleotides comprising the SNPs described herein.

Positions within the STAT6 genomic nucleic acid sequence can be counted, for example, from nucleotide 1 of SEQ ID NO:1, from position 10801 of the bovine STAT6 sequence in FIG. 1, in reference to the adenosine nucleotide of the ATG start codon, or alternatively, in reference to the intron or exon in which the SNP resides. A STAT6 polynucleotide or polypeptide sequence is typically from a domesticated livestock animal, for example, a bovine, ovine, equine, porcine or gallus. The nucleic acids and proteins of the invention include both naturally occurring or recombinant molecules. The STAT6 genomic nucleic acid sequence is provided as SEQ ID NO:1, and also published as ENSEMBL accession number ENSBTAG00000006335 (which correlates to positions 17,194-26,693 of the STAT6 gene as defined in FIG. 1). As used herein, a "STAT6 gene" will have a nucleic acid sequence that has greater than about 95%, preferably greater than about 96%, 97%, 98%, 99%, or higher nucleotide sequence identity, preferably over a region of at least about 500, 1000, 2000, 3000, 50000 or more nucleotides, or over the full-length, to a STAT6 genomic nucleic acid, for example, SEQ ID NO:1 or ENSBTAG00000006335.

The term "livestock animal" refers to any breed or population of animal kept by humans for a useful, commercial purpose. As used herein, a livestock animal can be mammal or avian. Generally, the livestock animal is an agricultural mammal, for example, bovine, equine, ovine, porcine. Livestock animals raised for the production of meat find use with the present invention, for example, beef cattle, pigs, goats, sheep, bison, chickens, turkeys, etc. The livestock animals can be in all stages of development, including embryonic, fetal, neonate, yearling, juvenile and adult stages.

The term "bovine" refers to a domesticated (purebred or crossbreeds) or wild mammal that is a Bovinae, for example, of the genera *Bos* (e.g., cattle or oxen) or *Bison* (e.g., American buffalo). Exemplary mammals of the genus *Bos* include without limitation *Bos taurus, Bos bovis, Bos frontalis* (gayal), *Bos gaurus* (gaur), *Bos grunniens* (domestic yak), *Bos grunniens* x *Bos taurus* (dzo), *Bos indicus* (zebu cattle), *Bos indicus gudali* (Gudali zebu), *Bos indicus* x *Bos taurus* (hybrid cattle), *Bos javanicus* (banteng), *Bos primigenius* (aurochs), and *Bos sauveli* (kouprey). *Bos* species for the production of meat products, e.g., beef cattle are of use in the present invention. Exemplary breeds of *Bos* without limitation Black Angus, Red Angus, Horned Hereford, Polled Hereford, Charolais, Simmental, Limousine, Chianina, Brahman, Santa Gertrudis, and Wagyu. Other breeds of beef cattle of use are listed in Tables 1 and 2, infra.

The term "carcass traits" refers to traits of an animal's carcass determined after the animal has been slaughtered.

The term "feedlot traits" refers to traits of a live animal during the time period it is resident in a feedlot.

The terms "nucleic acid" and "polynucleotide" are used interchangeably herein to refer to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

A "single nucleotide polymorphism" or "SNP" refers to polynucleotide that differs from another polynucleotide by a single nucleotide exchange. For example, without limitation, exchanging one A for one C, G or T in the entire sequence of polynucleotide constitutes a SNP. Of course, it is possible to have more than one SNP in a particular polynucleotide. For example, at one locus in a polynucleotide, a C may be exchanged for a T, at another locus a G may be exchanged for an A and so on. When referring to SNPs, the polynucleotide is most often DNA and the SNP is one that usually results in a change in the genotype that is associated with a corresponding change in phenotype of the organism in which the SNP occurs.

A "variant" is a difference in the nucleotide sequence among related polynucleotides. The difference may be the deletion of one or more nucleotides from the sequence of one polynucleotide compared to the sequence of a related polynucleotide, the addition of one or more nucleotides or the substitution of one nucleotide for another. The terms "mutation," "polymorphism" and "variant" are used interchangeably herein to describe such variants. As used herein, the term "variant" in the singular is to be construed to include multiple variances; i.e., two or more nucleotide additions, deletions and/or substitutions in the same polynucleotide. A "point mutation" refers to a single substitution of one nucleotide for another.

A nucleic acid "that distinguishes" as used herein refers to a polynucleotide(s) that (1) specifically hybridizes under stringent hybridization conditions to an anti-sense strand corresponding to a nucleic acid sequence encoding a STAT6 protein, and conservatively modified variants thereof, or (2) has a nucleic acid sequence that has greater than about 80%, 85%, 90%, 95%, preferably greater than about 96%, 97%, 98%, 99%, or higher nucleotide sequence identity, preferably over a region of at least about 25, 50, 100, 200, 500, 1000, or more nucleotides, to a STAT6 nucleic acid (e.g., a sequence as set forth in SEQ ID NO:1, or complements or a subsequences thereof. A nucleic acid that distinguishes a first STAT6 polymorphism from a second STAT6 polymorphism at the same position in the STAT6 sequence will allow for polynucleotide extension and amplification after annealing to a STAT6 polynucleotide comprising the first polymorphism, but will not allow for will not allow for polynucleotide extension or amplification after annealing to a STAT6 polynucleotide comprising the second polymorphism. In other embodiments, a nucleic acid that distinguishes a first STAT6 polymorphism from a second STAT6 polymorphism at the same position in the STAT6 sequence will hybridize to a STAT6 polynucleotide comprising the first polymorphism but will not hybridize to a STAT6 polynucleotide comprising the second polymorphism.

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5-10° C. lower than the thermal melting point I for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, optionally 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In particular, an isolated STAT6 nucleic acid is separated from open reading frames that flank the STAT6 gene and encode proteins other than STAT6. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, α-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine I, Lysine (K);
5) Isoleucine (I), Leucine (L), Methionine (M), Valine (V);

6) Phenylalanine (F), Tyrosine (Y), Tryptophan (W);
7) Serine (S), Threonine (T); and
8) Cysteine (C), Methionine (M)
(see, e.g., Creighton, Proteins (1984)).

The terms "identical" or percent "identity," in the context of two or more nucleic acids or polypeptide sequences, refer to two or more sequences or subsequences that are the same or have a specified percentage of amino acid residues or nucleotides that are the same (i.e., share at least about 80% identity, for example, at least about 85%, 90%, 91%, 92%, 93%, 94%, 95%, 96%, 97%, 98%, 99% identity over a specified region to a reference sequence, e.g., SEQ ID NO:1 or a polypeptide encoded by SEQ ID NO:1), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Preferably, the identity exists over a region that is at least about 25 amino acids or nucleotides in length, for example, over a region that is 50-100 amino acids or nucleotides in length, or over the full-length of a reference sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins to STAT6 nucleic acids and proteins, the BLAST and BLAST 2.0 algorithms and the default parameters discussed below are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

Examples of algorithms that are suitable for determining percent sequence identity and sequence similarity are the BLAST and BLAST 2.0 algorithms, which are described in Altschul et al. (1990) J. Mol. Biol. 215: 403-410 and Altschul et al. (1977) Nucleic Acids Res. 25: 3389-3402, respectively. Software for performing BLAST analyses is publicly available through the National Center for Biotechnology Information (on the worldwide web at ncbi.nlm.nih.gov/). The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff& Henikoff, Proc. Natl. Acad. Sci. USA 89:10915 (1989)).

The BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

BRIEF DESCRIPTION OF THE DRAWINGS

FIGS. 1A to 1I illustrate the annotated sequence of the bovine STAT6 genomic sequence (SEQ ID NO:1). The positions of SNP IDs 10922, 14257, 14636, 16084, 19597, 24000 and 25999 and exons 1-21 are identified. Each exon is labeled with a letter "E" with the number of the exon, and is marked with a line above the corresponding sequence ("~~~~~~").

FIGS. 2A to 2B illustrate a multiple sequence alignment of the STAT6 protein sequence, highlighting the high degree of conservation between bovine (SEQ ID NO:40), equine (SEQ ID NO:41), canine (SEQ ID NO:42), human (SEQ ID NO:43) and murine (SEQ ID NO:44) STAT6 amino acid sequences.

DETAILED DESCRIPTION

1. Introduction

Figure 3:
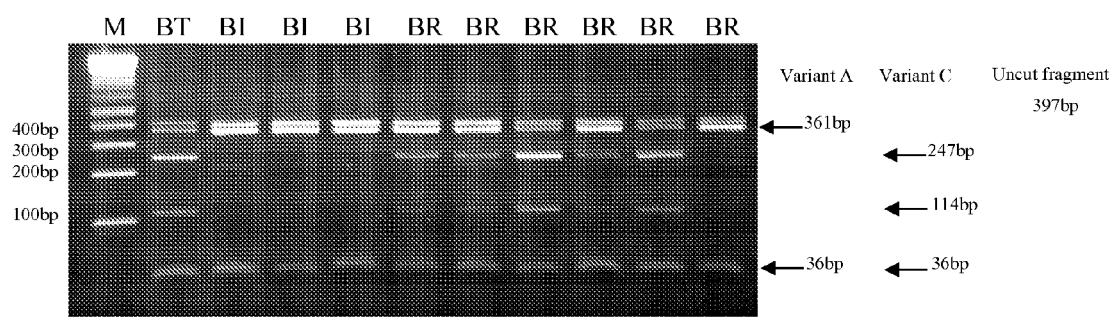
FIG. 3 illustrates a representative result of a PCR/RFLP genotyping assay for STAT6 SNP ID 14257. Detecting polymorphisms at SNP ID 14257 differentiates between *Bos taurus* and *Bos indicus* species.

Single nucleotide polymorphisms (SNPs) can provide a useful way in which to distinguish different alleles of a gene. Furthermore, when the presence of a SNP can be associated with a specific phenotype, the SNP operates as a powerful marker and can be used to predict phenotypic outcomes based on an animal's genotypic makeup. The present invention relates to methods of managing livestock animals, for example, cattle, sheep, goats, horses and pigs, and taking advantage of genetic factors that affect an animal's fat distribution and disposition. By identifying animals with a particular genotype, with respect to herein described SNP alleles, it is possible to identify animals that will display phenotypes associated with carcass traits including back fat, carcass weight, and cutability; and feedlot traits including average daily gain, days on feed and dry matter intake, as compared to animals lacking the desired genotype.

In particular, the present invention relates to methods for establishing the genetically determined predispositions of individual livestock animals, for example, cattle, sheep, goats, horses and pigs, within a group of such animals, to meet particular desired characteristics with respect to carcass and feedlot traits, based on the association of specific STAT6 alleles with statistically correlated carcass and feedlot phenotypes.

The present invention provides methods for analyzing the genotype of animals with respect to the STAT6 gene, and using the genotype information to select animals with desired traits related to carcass and feedlot traits. Such knowledge further permits producers to charge a premium for the more desirable phenotype, and permits breeders to selectively breed animals for genotypes that will result in the most desirable phenotypes.

The present invention is based in part on the unexpected discovery that the location of ETH10 is within the first exon of STAT6 (e.g., positions 13,805-13,844 of the bovine STAT6 genomic nucleic acid sequence in FIG. 1). Using the bovine whole genome radiation hybrid panel, it was demonstrated that STAT6 mapped 0.3 cR from ETH10 with a LOD score of 20.4. Available EST sequences were assembled and part of the bovine STAT6 gene from cDNA was sequenced, confirming that the location of ETH 10 is indeed within the first exon of STAT6. The present invention provides a biological explanation for the association between the amount of marbling (the size and number of adipocytes within muscle tissue) and genotype at ETH10 and/or STAT6 alleles.

In particular, three single nucleotide polymorphisms (SNPs) within the STAT6 gene, i.e., SNP ID 14636, SNP ID 16084 and SNP ID 19597, have been identified that are statistically correlated with economically important feedlot and carcass traits in livestock animals, for example, bovines, for example, *Bos taurus*. In addition, four SNPS within the STAT6 gene, i.e., SNP ID 10922, SNP ID 14257, SNP ID 24000, and SNP ID 25999, have been identified that are fixed in *Bos taurus* and *Bos indicus*, and are useful for genetically distinguishing these two *Bos* species that are oftentimes phenotypically indistinguishable.

2. Methods of Determining Desirable Traits in Livestock Animals by Determining SNPs in the STAT6 Gene a. Livestock Animals

The present invention is useful for identifying desired phenotypes in a livestock animal based on its STAT6 genotype, particularly at SNP IDs 16084, 19597 and 14636. The livestock animal can be any animal that is raised commercially for meat production, for example, beef, pork, mutton, lamb or poultry. Oftentimes the livestock animal is a mammal. In some embodiments, the livestock animal is a bovine, ovine, equine, or porcine. In some embodiments, the livestock animal is a bovine, for example, of the genus *Bos*, for example, beef cattle.

The STAT6 genomic nucleic acid sequence, protein-encoding nucleic acid sequence (i.e., mRNA or cDNA), and amino acid sequence is conserved amongst mammalian species. The amino acid alignment in FIG. 2 shows that the bovine STAT6 protein shares about 93% amino acid sequence identity with the STAT6 protein of horse and dog, and about 92% amino acid sequence identity with the murine STAT6 protein. The bovine STAT6-encoding nucleic acid sequence shares about 95% nucleic acid sequence identity with the STAT6-encoding nucleic acid sequence of horse and about 93% nucleic acid sequence identity with the STAT6-encoding nucleic acid sequence of dog.

b. Biological Samples

The methods of the present invention involve taking a biological sample comprising genomic DNA from the animal to be tested. The biological sample can be from solid tissue or a biological fluid that contains a nucleic acid comprising a single nucleotide polymorphism (SNP) described herein, e.g., a nucleic acid comprising a STAT6 gene. The biological sample can be tested by the methods described herein and include body fluids including whole blood, serum, plasma, cerebrospinal fluid, urine, lymph fluids, semen, and various external secretions of the respiratory, intestinal and genitourinary tracts, tears, saliva, milk, white blood cells, myelomas, and the like; and biological fluids such as cell extracts, cell culture supernatants; fixed tissue specimens; and fixed cell specimens. Biological samples can also be from solid tissue, including hair bulb, skin, biopsy or autopsy samples or frozen sections taken for histologic purposes. These samples are well known in the art. A biological sample is obtained from any livestock animal to be tested for STAT6 SNPs as described herein, including, e.g., a beef cow. A biological sample can be suspended or dissolved in liquid materials such as buffers, extractants, solvents and the like.

c. SNPs in STAT6 Correlated with Desirable Traits

Livestock mammals, including bovines, ovines, equines and porcines, are diploid organisms possessing pairs of homologous chromosomes. Thus, at a typical genetic locus, an animal has three possible genotypes that can result from the combining of two different alleles (e.g. A and B). The animal may be homozygous for one or another allele, or heterozygous, possessing one of each of the two possible alleles (e.g. AA, BB or AB).

The STAT6 SNP IDs statistically correlated with desirable carcass and feedlot phenotypes include SNP ID 14636, SNP ID 16084 and SNP ID 19597.

STAT6 SNP ID 14636 is identified in FIG. 1. As shown in FIG. 1, SNP ID 14636 is positioned at nucleotide 14989 of the sequence depicted in FIG. 1, or at position 4189 of SEQ ID NO:1. SNP ID 14636 is also positioned at nucleotide 656 of intron 1 of the STAT6 sequence depicted in FIG. 1. A homozygous "CC" genotype at STAT6 SNP ID 14636 is statistically correlated with the carcass and feedlot phenotypes of increased back fat rate, fewer days on feed, and increased average daily gain. A homozygous "GG" genotype at STAT6 SNP ID 14636 is statistically correlated with the carcass and feedlot phenotypes of decreased back fat rate, greater number of days on feed, and decreased average daily gain. See, Table 4.

STAT6 SNP ID 16084 is identified in FIG. 1. As shown in FIG. 1, SNP ID 16084 is positioned at nucleotide 16437 of the sequence depicted in FIG. 1, or at position 5637 of SEQ ID NO:1. SNP ID 16084 is also positioned at nucleotide 2104 of intron 1 of the STAT6 sequence depicted in FIG. 1. A homozygous "AA" genotype at STAT6 SNP ID 16084 is statistically correlated with the carcass phenotypes of increased back fat, increased calculated yield grade and decreased cutability. A homozygous "CC" genotype at STAT6 SNP ID 16084 is statistically correlated with the carcass phenotypes of decreased back fat, decreased calculated yield grade and increased cutability. See, Table 4.

STAT6 SNP ID 19597 is identified in FIG. 1. As shown in FIG. 1, SNP ID 19597 is positioned at nucleotide 19950 of the sequence depicted in FIG. 1, or at position 9150 of SEQ ID NO:1. SNP ID 19597 is also positioned at nucleotide 20 of intron 8 of the STAT6 sequence depicted in FIG. 1. A homozygous "AA" genotype at STAT6 SNP ID 19597 is statistically correlated with the carcass and feedlot phenotypes of increased hot carcass weight, increased dry matter intake and fewer days on feed. A homozygous "GG" genotype at STAT6 SNP ID 19597 is statistically correlated with the carcass and feedlot phenotypes of decreased hot carcass weight, decreased dry matter intake and greater number of days on feed. See, Table 4.

d. Carcass Traits

Carcass traits statistically correlated with the STAT6 SNPs identified in the present inventions include back fat thickness (BFAT), calculated yield grade (CALYG), cutability (CUT) and hot carcass weight (HCW).

Back Fat Thickness (BFAT). Back fat thickness is expressed in tenths of an inch of the fat thickness at the 12th rib (as measured between the 12th and 13th ribs) of an animal's carcass. This is the amount of fat covering the ribeye.

Hot Carcass Weight (HCW). Hot carcass weight is the weight expressed in pounds of an animal after slaughter. Hot carcass weight is obtained immediately after dressing (i.e., the viscera and hide are removed) and prior to carcass chilling.

Calculated Yield Grade (CALYG) refers to a calculated value that includes back fat thickness (BFAT), ribeye area (REA), hot carcass weight (HCW), and kidney, pelvic, and heart fat percentage (KPH). This value is calculated using any of several known equations. Below are provided the calculated yield grade equations used by the USDA and by Iowa State University.

$$CalYG=2.46+2.49(BFAT)-0.13(REA)+0.0002(HCW)+0.115(KPH)$$

(Reference: 2000 Beef Research Report—Iowa State University—A. S. Leaflet R1730).

$$CalYG=2.5+2.5(BFAT)-0.32(REA)+0.0038(HCW)+0.2(KPH)$$

(USDA yield equation)

Yield grades are used to identify carcasses that differ in yield of boneless, closely trimmed retail cuts from the round, loin, rib, and chuck. Yield grades range from 1 through 5. A yield grade 5 carcass would have the lowest cutability and would be characterized as light muscled and/or excessively fat. Accordingly, a lower calculated yield grade value is more desirable and a higher yield grade value is less desirable.

Because current yield grades are too broad to clearly define value differences in retail yield, yield grades 2 and 3 have been divided into 2A and 2B and 3A and 3B respectively. Yield grades 2.0 to 2.5 are classified 2A and 2.5 to 3.0 are classified 2B. Similarly, yield grades 3.0 to 3.5 are classified 3A and 3.5 to 4.0 are classified 3B. Combining quality grade with yield grade more clearly defines carcass value than when quality grade alone is used. See, e.g., the worldwide web at caf.wvu.edu/~forage/yieldgrd/yieldgrades.htm.

Carcass traits considered in a calculated yield grade equation, are described, for example, on the worldwide web at ianrpubs.unl.edu/epublic/pages/publicationD.jsp?publicationId=19.

As discussed above, external back fat thickness is measured in tenths of an inch and is the amount of fat covering the ribeye at the point of the 12th and 13th ribs.

Hot carcass weight and REA work together as an indication of overall muscling of the animal. A heavy carcass is expected to have more total muscle than a lighter weight carcass. If a carcass does not have as much muscling as you would expect from an average carcass of that weight, it makes the yield grade less desirable. If a carcass has more muscling than average for that weight, it improves the yield grade.

Percentage of KPH measures the amount of internal fat. All animals have some fat surrounding their internal organs such as the liver or heart. The less of this fat a carcass has, the better for the yield grade. The amount of KPH is expressed as a percentage of carcass weight. For example, an 800 pound carcass with 2.5% KPH has 20 pounds of internal fat.

External adjusted fat thickness (more fat=less desirable yield grade)

Hot carcass weight (heavier weight=less desirable yield grade)

Percentage of kidney, pelvic and heart fat (more fat=less desirable yield grade)

Ribeye area (larger ribeye=more desirable yield grade)

Cutability. The percent yield of the carcass is also called the cutability of the carcass. The cutability of the carcass is calculated from the following formula:

$$\% \text{ retail cuts}=51.34-(5.78\times\text{Adj. Fat thickness})-(0.0088\times\text{hot carcass weight})-(0.462\times KPH)+(0.740\times\text{ribeye area})$$

Beef yield grades provide an estimate of how much lean, edible meat the carcass will produce. Yield grades are 1, 2, 3, 4 and 5, with 1 being a lean, heavy muscled carcass that will yield a high percentage of lean meat, and 5 being an overly fat, light muscled carcass. If all the bones and fat are removed from the major portions of the carcass (the rounds, loins, ribs and chucks), roughly 53-55% of a Yield Grade 1 carcass will become saleable, retail meat. From a Yield Grade 1, 800 pound carcass, you would expect approximately 430 lbs of meat. From an 800 pound, Yield Grade 5 carcass, you could expect a 43-45% yield, or about 350 lbs of meat. See, e.g., the worldwide web at ianrpubs.unl.edu/epublic/pages/publicationD.jsp?publicationId=19.

e. Feedlot Traits

Feedlot traits statistically correlated with the STAT6 SNPs identified in the present inventions include dry matter intake (DMI), days on feed (DOF), average daily gain, and back fat rate (BFAT RATE). These are arbitrary measurements from the time animals arrive in the feedlot until they are slaughtered. The measurements are used to recharge owners that subcontract feeding their animals in the feedlot, and or to calculate the economic efficiency of feeding different lots of animals.

Days on feed (DOF) is measured in days fed in the feedlot from the time the animals enter the feedlot until they are slaughtered approximately when they have 0.4-0.5 in back fat or close to a Choice grade.

Average daily gain (ADG) is the average daily weight gain of the animal in pounds in the feedlot measured from the time of arrival to the feedlot until the animal is slaughtered.

Dry matter intake (DMI) is the amount of feed consumed in dry matter basis (pounds) by an animal in the feedlot measured from the time of arrival to the feedlot until the animal is slaughtered.

Back Fat Rate (BFAT RATE) is the rate of back fat accumulation on an animal measured on a daily basis. Back fat can be measured on the animal using any method known in the art, including for example, ultrasound techniques.

f. Detection of SNPs

The STAT6 SNPs can be detected using any methods known in art, including without limitation amplification, sequencing and hybridization techniques. Detection techniques for evaluating nucleic acids for the presence of a single base change involve procedures well known in the field of molecular genetics. Methods for amplifying nucleic acids find use in carrying out the present methods. Ample guidance for performing the methods is provided in the art. Exemplary references include manuals such as PCR Technology: PRINCIPLES AND APPLICATIONS FOR DNA AMPLIFICATION (ed. H. A. Erlich, Freeman Press, NY, N.Y., 1992); PCR PROTOCOLS: A GUIDE TO METHODS AND APPLICATIONS (eds. Innis, et al., Academic Press, San Diego, Calif., 1990); CURRENT PROTOCOLS IN MOLECULAR BIOLOGY, Ausubel, 1990-2008, including supplemental updates; Sambrook & Russell, Molecular Cloning, A Laboratory Manual (3rd Ed, 2001).

According to one aspect of the present invention, there is provided a method for distinguishing livestock animals e.g., bovines having a STAT6 gene polymorphism. The method comprises the steps of first isolating a genomic DNA sample from a livestock animal, e.g., bovine, and then detecting, e.g., amplifying a region of the STAT6 gene using an oligonucleotide pair to form nucleic acid amplification products of STAT6 gene polymorphism sequences. Amplification can be by any of a number of methods known to those skilled in the art including PCR, and the invention is intended to encompass any suitable methods of DNA amplification. A number of DNA amplification techniques are suitable for use with the present invention. Conveniently such amplification techniques include methods such as polymerase chain reaction (PCR), strand displacement amplification (SDA), nucleic acid sequence based amplification (NASBA), rolling circle amplification, T7 polymerase mediated amplification, T3 polymerase mediated amplification and SP6 polymerase mediated amplification. The precise method of DNA amplification is not intended to be limiting, and other methods not listed here will be apparent to those skilled in the art and their use is within the scope of the invention.

In some embodiments, the polymerase chain reaction (PCR) process is used (see, e.g., U.S. Pat. Nos. 4,683,195 and 4,683,202. PCR involves the use of a thermostable DNA polymerase, known sequences as primers, and heating cycles, which separate the replicating deoxyribonucleic acid (DNA), strands and exponentially amplify a gene of interest. Any type of PCR, including quantitative PCR, RT-PCR, hot start PCR, LA-PCR, multiplex PCR, touchdown PCR, finds use. In some embodiments, real-time PCR is used.

The amplification products are then analyzed in order to detect the presence or absence of at least one polymorphism in the STAT6 gene that is associated with the desired phenotypes, as discussed herein. By practicing the methods of the present invention and analyzing the amplification products it is possible to determine the genotype of individual animals with respect to the polymorphism.

In some embodiments, analysis may be made by restriction fragment length polymorphism (RFLP) analysis of a PCR amplicon produced by amplification of genomic DNA with the oligonucleotide pair. In order to simplify detection of the amplification products and the restriction fragments, those of skill will appreciate that the amplified DNA will further comprise labeled moieties to permit detection of relatively small amounts of product. A variety of moieties are well known to those skilled in the art and include such labeling tags as fluorescent, bioluminescent, chemiluminescent, and radioactive or colorigenic moieties.

A variety of methods of detecting the presence and restriction digestion properties of STAT6 gene amplification products are also suitable for use with the present invention. These can include methods such as gel electrophoresis, mass spectroscopy or the like. The present invention is also adapted to the use of single stranded DNA detection techniques such as fluorescence resonance energy transfer (FRET). For FRET analysis, hybridization anchor and detection probes may be used to hybridize to the amplification products. The probes sequences are selected such that in the presence of the SNP, for example, the resulting hybridization complex is more stable than if there is a G or C residue at a particular nucleotide position. By adjusting the hybridization conditions, it is therefore possible to distinguish between animals with the SNP and those without. A variety of parameters well known to those skilled in the art can be used to affect the ability of a hybridization complex to form. These include changes in temperature, ionic concentration, or the inclusion of chemical constituents like formamide that decrease complex stability. It is further possible to distinguish animals heterozygous for the SNP versus those that are homozygous for the same. The method of FRET analysis is well known to the art, and the conditions under which the presence or absence of the SNP would be detected by FRET are readily determinable.

Suitable sequence methods of detection also include e.g., dideoxy sequencing-based methods and Maxam and Gilbert sequence (see, e.g., Sambrook and Russell, supra). Suitable HPLC-based analyses include, e.g., denaturing HPLC (dHPLC) as described in e.g., Premstaller and Oefner, LC-GC Europe 1-9 (July 2002); Bennet et al., BMC Genetics 2:17 (2001); Schrimi et al., Biotechniques 28(4):740 (2000); and Nairz et al., PNAS USA 99(16):10575-10580 (2002); and ion-pair reversed phase HPLC-electrospray ionization mass spectrometry (ICEMS) as described in e.g., Oberacher et al.; Hum. Mutat. 21(1):86 (2003). Other methods for characterizing single base changes in STAT6 alleles include, e.g., single base extensions (see, e.g., Kobayashi et al, Mol. Cell. Probes, 9:175-182, 1995); single-strand conformation polymorphism analysis, as described, e.g, in Orita et al., Proc. Nat. Acad. Sci. 86, 2766-2770 (1989), allele specific oligonucleotide hybridization (ASO) (e.g., Stoneking et al., Am. J. Hum. Genet. 48:70-382, 1991; Saiki et al., Nature 324, 163-166, 1986; EP 235,726; and WO 89/11548); and sequence-specific amplification or primer extension methods as described in, for example, WO 93/22456; U.S. Pat. Nos. 5,137,806; 5,595, 890; 5,639,611; and U.S. Pat. No. 4,851,331; 5'-nuclease assays, as described in U.S. Pat. Nos. 5,210,015; 5,487,972; and 5,804,375; and Holland et al., 1988, Proc. Natl. Acad. Sci. USA 88:7276-7280.

Methods for detecting single base changes well known in the art often entail one of several general protocols: hybridization using sequence-specific oligonucleotides, primer extension, sequence-specific ligation, sequencing, or electrophoretic separation techniques, e.g., singled-stranded conformational polymorphism (SSCP) and heteroduplex analysis. Exemplary assays include 5' nuclease assays, template-directed dye-terminator incorporation, molecular beacon allele-specific oligonucleotide assays, single-base extension assays, and SNP scoring by real-time pyrophosphate sequences. Analysis of amplified sequences can be performed using various technologies such as microchips, fluorescence polarization assays, and matrix-assisted laser desorption ionization (MALDI) mass spectrometry. In addition to these frequently used methodologies for analysis of nucleic acid samples to detect single base changes, any method known in the art can be used to detect the presence of the STAT6 SNPs described herein.

For example FRET analysis can be used as a method of detection. Conveniently, hybridization probes comprising an anchor and detection probe, the design of which art is well known to those skilled in the art of FRET analysis, are labeled with a detectable moiety, and then under suitable conditions are hybridized a STAT6 amplification product containing the site of interest in order to form a hybridization complex. A variety of parameters well known to those skilled in the art can be used to affect the ability of a hybridization complex to form. These include changes in temperature, ionic concentration, or the inclusion of chemical constituents like formamide that decrease complex stability. The presence or absence of the STAT6 SNP is then determined by the stability of the hybridization complex. The parameters affecting hybridization and FRET analysis are well known to those skilled in the art. The amplification products and hybridization probes described herein are suitable for use with FRET analysis.

In one embodiment, the detected polymorphism or allele or position of the bovine STAT6 gene is at SNP ID 14636, and the oligonucleotide pair comprises a forward primer comprising a nucleic acid sequence selected from 5'-GCTGGT-CACTCTTCCTAATC-3' (SEQ ID NO:11) and 5'-TCT-GACTTAGGGATCACCTC-3' (SEQ ID NO:12); and a reverse primer comprising a nucleic acid sequence selected from 5'-GACCTCTATCTCTACCCTAC-3' (SEQ ID NO:13); 5'-ACCTCTATCTCTACCCTACG-3' (SEQ ID NO:14) and 5'-CTCTACCCTACGGGGAC-3' (SEQ ID NO:15).

In one embodiment, the detected polymorphism or allele or position of the bovine STAT6 gene is at SNP ID 16084, and the oligonucleotide pair comprises a forward primer comprising a nucleic acid sequence selected from 5'-TTTCCCTACT-GCCCCATTGC-3' (SEQ ID NO:16); 5'-TCA-GAGAGCTTTCCCTACTG-3' (SEQ ID NO:17); and 5'-CCTGTCTCTTACCCTCT-3' (SEQ ID NO:18); and a reverse primer comprising the nucleic acid sequence 5'-TAATGGAGTGGGAAGAGCTG-3' (SEQ ID NO:19).

In one embodiment, the detected polymorphism or allele or position of the bovine STAT6 gene is at SNP ID 19597, and the oligonucleotide pair comprises a forward primer comprising a nucleic acid sequence selected from 5'-CACACTCGT-CACCAGGTATG-3' (SEQ ID NO:20) and 5'-GAGC-CCCCCTGCCTG-3' (SEQ ID NO:21); and a reverse primer comprising a nucleic acid sequence selected from 5'-AACTCTGACCCTCCTGTTTC-3' (SEQ ID NO:22) and 5'-GGGGTCTGCTCTCCA-3' (SEQ ID NO:23).

g. Selecting Livestock Animals with Desirable Traits

The present invention provides a method of selecting individual livestock animals based on the knowledge of an animal's STAT6 genotype. With respect to the SNPs described in the present invention, livestock animals with alleles at SNP IDs 14636, 16084, 19597 correlated with desirable carcass and feedlot traits can be selected.

For example, a "CC" homozygous genotype at SNP ID 16084 is correlated with the carcass phenotypes of decreased back fat, increased cutability and decreased calculated yield grade. An "AA" homozygous genotype at SNP ID 16084 is correlated with the carcass phenotypes of increased back fat, decreased cutability and increased calculated yield grade.

Similarly, an "AA" homozygous genotype at SNP ID 19597 is correlated with the carcass and feedlot phenotypes of an increased hot carcass weight, increased dry matter intake and fewer days on feed. A "GG" homozygous genotype at SNP ID 19597 is correlated with the carcass and feedlot phenotypes of a decreased hot carcass weight, decreased dry matter intake and greater number of days on feed.

A "CC" homozygous genotype at SNP ID 14636 is correlated with the carcass and feedlot phenotypes of an increased back fat rate, increased average daily gain and fewer days on feed. A "GG" homozygous genotype at SNP ID 14636 is correlated with the carcass and feedlot phenotypes of a decreased back fat rate, decreased average daily gain and greater number of days on feed. See, Table 4.

According to the methods of the present invention, a livestock animal can be selected based on its STAT6 genotype at SNP IDs 16084, 19597 and 14636. With the knowledge of the animal's STAT6 genotype one can then identify and sort animals into groups of like phenotype(s), or otherwise use the knowledge of the genotype in order to predict which animals will have the desired phenotypes, for example, decreased back fat, increased cutability, decreased calculated yield grade, increased hot carcass weight, increased dry matter intake, fewer days on feed, increased or decreased back fat rate, and increased average daily gain. Knowledge of the animal's STAT6 genotype allows a breeder to encourage breeding between animals with a desired STAT6 genotype, and to discourage breeding between animals with an undesirable STAT6 genotype.

Selecting or sorting can be taken to mean placing animals in physical groupings such as pens, so that animals of like genotype are kept separate from animals of a different genotype. This would be a useful practice in the case of breeding programs where it would be desirable to produce animals of particular genotypes. For example, it may be desirable to establish herds that are homozygous "CC" at SNP ID 16084, homozygous "AA" at SNP ID 19597 and homozygous "CC" at SNP ID 14636 within the STAT6 gene, such that breeding among these animals would only produce animals with a desired STAT6 genotype. On the other hand, it may also be desirable to decrease production of animals with an undesired STAT6 genotype. Separating out animals with the desired STAT6 genotype(s) would prevent animals with an undesired STAT6 genotype from breeding with animals possessing a desired STAT6 genotype, facilitating the reproduction of animals with an increased tendency to display the desired phenotypes associated with the STAT6 alleles. Furthermore, ensuring that at least one animal in a breeding pair possesses desired STAT6 alleles allows for the frequency of the desired STAT6 alleles to be increased in the next, and subsequent generations. For example, a favorable breed of *Bos* may not have a desired STAT6 genotype, but the desired STAT6 genotype could be bred into the genepool of the favorable breed of *Bos*.

Sorting may also be of a "virtual" nature, such that an animal's genotype is recorded either in a notebook or computer database. In this case, animals could then be selected based on their known genotype without the need for physical separation. This would allow one to select for animals of desired phenotype where physical separation is not required.

3. Distinguishing *Bos taurus* from *Bos indicus* by Determining STAT6 SNPs

In a related aspect, the invention provides a method for distinguishing bovines, in particular *Bos taurus* from *Bos indicus*, based on STAT6 gene polymorphisms that are fixed in each species. The method comprises the steps of first isolating a genomic DNA sample from the bovine, and then detecting, e.g., amplifying a region of the STAT6 gene using an oligonucleotide pair to form nucleic acid amplification products of STAT6 gene polymorphism sequences. A biological sample comprising genomic DNA is taken from the bovine to be tested, as described above. The methods used to detect the STAT6 polymorphism can be any means of SNP detection known in the art, as discussed above, including without limitation, amplification, sequencing and hybridization techniques. Amplification can be by any of a number of methods known to those skilled in the art, as discussed above. Upon determining the species of the bovine based on genotypic analysis, the bovine is selected or rejected, either physically or virtually, as described above.

a. STAT6 SNPs Useful to Distinguish *Bos taurus* from *Bos indicus*

STAT6 SNP ID 10922 is identified in FIG. 1. As shown in FIG. 1, SNP ID 10922 is positioned at nucleotide 10922 of the sequence depicted in FIG. 1, or at position 122 of SEQ ID NO:1. SNP ID 10922 is also positioned at nucleotide 122 within the 5'-UTR of the STAT6 sequence depicted in FIG. 1. A homozygous "AA" genotype at STAT6 SNP ID 10922 indicates that the bovine is *Bos taurus*. A homozygous "GG" genotype at STAT6 SNP ID 10922 indicates that the bovine is *Bos indicus*. See, Table 3.

STAT6 SNP ID 14257 is identified in FIG. 1. As shown in FIG. 1, SNP ID 14257 is positioned at nucleotide 14257 of the sequence depicted in FIG. 1, or at position 3457 of SEQ ID NO:1. SNP ID 14257 is also positioned at nucleotide 24 of intron 1 of the STAT6 sequence depicted in FIG. 1. A homozygous "CC" genotype at STAT6 SNP ID 14257 indicates that the bovine is *Bos taurus*. A homozygous "AA" genotype at STAT6 SNP ID 14257 indicates that the bovine is *Bos indicus*. See, Table 3.

STAT6 SNP ID 24000 is identified in FIG. 1. As shown in FIG. 1, SNP ID 24000 is positioned at nucleotide 24353 of the sequence depicted in FIG. 1, or at position 13553 of SEQ ID NO:1. SNP ID 24000 is also positioned at nucleotide 164 of intron 16 of the STAT6 sequence depicted in FIG. 1. A homozygous "TT" genotype at STAT6 SNP ID 24000 indicates that the bovine is *Bos taurus*. A homozygous "CC" genotype at STAT6 SNP ID 24000 indicates that the bovine is *Bos indicus*. See, Table 3.

STAT6 SNP ID 25999 is identified in FIG. 1. As shown in FIG. 1, SNP ID 25999 is positioned at nucleotide 26352 of the sequence depicted in FIG. 1, or at position 15552 of SEQ ID NO:1. SNP ID 25999 is also positioned at nucleotide 176 of intron 20 of the STAT6 sequence depicted in FIG. 1. A homozygous "TT" genotype at STAT6 SNP ID 25999 indicates that the bovine is *Bos taurus*. A homozygous "CC" genotype at STAT6 SNP ID 25999 indicates that the bovine is *Bos indicus*. See, Table 3.

In one embodiment, the detected polymorphism or allele or position of the bovine STAT6 gene is at SNP ID 10922, and the oligonucleotide pair comprises a forward primer comprising a nucleic acid sequence selected from 5'-TGT-GATGGGTTGAACTCTGC-3' (SEQ ID NO:24) and 5'-CT-GCCTCTCAAAAATTTATATATTA-3' (SEQ ID NO:25); and a reverse primer comprising a nucleic acid sequence selected from 5'-GGGTACCTCCTATGAATATG-3' (SEQ ID NO:26) and 5'-GGGATATGTGATTTCAACATA-3' (SEQ ID NO:27).

In one embodiment, the detected polymorphism or allele or position of the bovine STAT6 gene is at SNP ID 14257, and the oligonucleotide pair comprises a forward primer comprising a nucleic acid sequence selected from 5'-GGGCCTCT-GACTACCAATGT-3' (SEQ ID NO:9); 5'-TTTTTCCACA-CACCCCATCC-3' (SEQ ID NO:28); and 5'-GGGACGTGTTAAGGC-3' (SEQ ID NO:29); and a reverse primer comprising a nucleic acid sequence selected from 5'-CCACACCCTTGAAGAGGAAC-3' (SEQ ID NO:10); 5'-ACTTCCCCCCAACCCAGAG-3' (SEQ ID NO:30) and 5'-TTGCCCTCCTTCCCC-3' (SEQ ID NO:31). In some embodiments, the polymorphism or allele or position of the bovine STAT6 gene is at SNP ID 14257, and the oligonucleotide pair comprises forward primer 5'-GGGC-CTCTGACTACCAATGT-3' (SEQ ID NO:9) and reverse primer 5'-CCACACCCTTGAAGAGGAAC-3' (SEQ ID NO:10).

In one embodiment, the detected polymorphism or allele or position of the bovine STAT6 gene is at SNP ID 24000, and the oligonucleotide pair comprises a forward primer comprising a nucleic acid sequence selected from 5'-TCATTTCCCT-GCTTCTGGAC-3' (SEQ ID NO:32) and 5'-CCATCATC-CATGCTCACCTTTTC-3' (SEQ ID NO:33); and a reverse primer comprising a nucleic acid sequence selected from 5'-ATGGAATGCTTCCGGGTTAG-3' (SEQ ID NO:34) and 5'-AGGGAGGAAGGGAGCT-3' (SEQ ID NO:35).

In one embodiment, the detected polymorphism or allele or position of the bovine STAT6 gene is at SNP ID 25999, and the oligonucleotide pair comprises a forward primer comprising a nucleic acid sequence selected from 5'-CCTCAGGAT-CATGCTGTGTC-3' (SEQ ID NO:36) and 5'-CCCT-TGCTCTGCTCAGA-3' (SEQ ID NO:37); and a reverse primer comprising a nucleic acid sequence selected from 5'-TGGTTCAGGCAGCTGTCTTC-3' (SEQ ID NO:38) and 5'-TTCTGCCATGGTCAC-3' (SEQ ID NO:39).

In some embodiments, the amplicon produced can be further subjected to restriction endonuclease digestion.

4. Kits for Genotypic Analysis of STAT6 Polymorphisms

The invention further provides diagnostic kits useful for determining the STAT6 genotypes of livestock animals, e.g., bovines. In general, each of the kits comprises one or more oligonucleotide primer pairs as described herein suitable to amplify the portions of the gene comprising the SNPs of the present invention, i.e., SNP IDs 10922, 14257, 14636, 16084, 19597, 24000 and 25999. The kits comprise forward and reverse primers suitable for amplification of a genomic DNA sample taken from an animal. As described above, the biological sample can be from any tissue or fluid in which genomic DNA is present. Conveniently, the sample may be taken from blood, skin or a hair bulb.

EXAMPLES

The following examples are offered to illustrate, but not to limit the claimed invention.

Example 1

Cattle Breed DNA Resource for SNP Discovery

The cattle breed DNA resource consists of approximately 6 animals of each of 12 cattle breeds (5 Black Angus, 6 Red Angus, 3 Horned Hereford, 3 Polled Hereford, 4 Charolais, 5 Simmental, 4 Limousine, Chianina, 6 Brahman, Santa Gertrudis, 3 Wagyu). The animals of each breed were selected to be unrelated at least 3 generations back. An effort was made to have the presence of diverse lines or types within each breed. At least 5 straws of semen were obtained from each animal. The semen came from 3 sources: purchased by Merial from semen AI companies, from Charles Farber (University of California at Davis) and from Milton Thomas (New Mexico State). Tables 1 and 2 show the details of the individual samples, source and number of semen straws. High quality DNA was extracted from one semen straw from each animal and four straws kept frozen for future use. DNA was extracted using PureGene DNA extraction kit, quantified on a UV spectrophotometer and tested for integrity on an agarose gel. The DNA panel was used as a SNP discovery resource by resequencing of the STAT6 gene as described below.

TABLE 1

DNA resource samples

| No. | Source | Breed | Short Name | Straws |
|---|---|---|---|---|
| 1 | Select Sires | Black Angus | Predestined | 2 |
| 2 | ABS Global | Black Angus | TRIPLE THREAT | 4 |
| 3 | ABS Global | Black Angus | EASY FORTUNE | 3 |
| 4 | ABS Global | Black Angus | CENTER CUT | 4 |
| 5 | Charles Farber | Black Angus | P S Franco 064 157 | 1 |
| 6 | Milton Thomas | Black Angus | NMSU 302 | DNA |
| 7 | Select Sires | Red Angus | Field Day | 2 |
| 8 | Select Sires | Red Angus | Vigor | 2 |
| 9 | Select Sires | Red Angus | Ho Ho | 2 |
| 10 | Select Sires | Red Angus | Heavenly | 2 |
| 11 | Select Sires | Red Angus | Duke | 2 |
| 12 | Select Sires | Red Angus | Rambler | 2 |
| 13 | Select Sires | Hereford Polled | Formula | 2 |
| 14 | ABS Global | Hereford Polled | JEDI | 4 |
| 15 | ABS Global | Hereford Polled | MASTER DUTY | 4 |
| 16 | ABS Global | Horned Hereford | HR ROBIN HOOD | 4 |
| 17 | ABS Global | Horned Hereford | Star Donald | 4 |
| 18 | Charles Farber | Horned Hereford | CL 1 Domino 0144K 1ET | 1 |
| 19 | Charles Farber | Horned Hereford | HH Advance 249B | 2 |
| 20 | Select Sires | Charolais Creme | Choice Plus | 2 |
| 21 | Select Sires | Charolais Creme | Sir Prime Time | 2 |
| 22 | ABS Global | Charolais Polled | SILVER EDGE | 4 |
| 23 | ABS Global | Charolais scurred | SENTINAL RULER | 4 |
| 24 | Select Sires | Simmental Red | Autobahn | 2 |
| 25 | Bovine Elite | Simmental Red | ER Americana 537B | 4 |
| 26 | Bovine Elite | Simmental Red | NLC Good A Nuff 33G | 4 |
| 27 | ABS Global | Simmental Traditional | FUTURE MODERATOR | 4 |
| 28 | Universalsemensales | Simmental Traditional | BEL DUTCH 89X | 4 |
| 29 | Bovine Elite | Simmental Traditional | Bar 5 Bernheim 405H | 4 |
| 30 | ABS Global | Gelbvieh Red | TOP BRASS | 4 |
| 31 | ABS Global | Gelbvieh Red | TABASCO | 4 |
| 32 | ABS Global | Gelbvieh Red | SIR ARNOLD | 4 |
| 33 | ABS Global | Gelbvieh Red | MODERATOR | 4 |
| 34 | Select Sires | Limousin Black | Equity | 2 |
| 35 | ABS Global | Limousin Red | POLLED MANHATTAN | 4 |
| 36 | ABS Global | Limousin Red | JUSTICE | 4 |
| 37 | Bovine Elite | Limousin Red | EXLR Latigo 029M | 4 |
| 38 | Universalsemensales | Wagyu "A" | BR Fukutsuru 0620 | 4 |
| 39 | Universalsemensales | Wagyu "B" | BR Takazakura 0604 | 4 |
| 40 | Universalsemensales | Wagyu "C" | BR Hirashigotayasu 9645 | 4 |
| 41 | Select Sires | Brangus | Carrarra | 2 |
| 42 | Milton Thomas | Brangus | NMSU 830 | DNA |
| 43 | Milton Thomas | Brangus | NMSU 628 | DNA |
| 44 | Milton Thomas | Brangus | CCR INTEGRITY F386F2 | DNA |
| 45 | Milton Thomas | Brangus | John Wayne 44L | DNA |
| 46 | Milton Thomas | Brangus | NIMITZ OF BRINKS 75L12 | DNA |
| 47 | Milton Thomas | Brangus | Mr 304 (Lucky) 118 | DNA |
| 48 | Milton Thomas | Brahman | 6X Sunland 874 | DNA |

TABLE 1-continued

DNA resource samples

| No. | Source | Breed | Short Name | Straws |
|---|---|---|---|---|
| 49 | Milton Thomas | Brahman | SRW MR. FLYING W 831 | DNA |
| 50 | Milton Thomas | Brahman | JDH MR. SALLUTO MANSO 300/2 | DNA |
| 51 | Select Sires | Brahman | 852/5 | 2 |
| 52 | Select Sires | Brahman | Rojo Bueno | 2 |
| 53 | Bovine Elite | Brahman | BB Mr Sting-Ray 10/0 | 4 |
| 54 | Bovine Elite | Shorthorn | ALM Tequila | 2 |
| 55 | Bovine Elite | Shorthorn | SBR Storm Chaser | 4 |
| 56 | Bovine Elite | Shorthorn | BG Spanky TPII | 4 |
| 57 | Bovine Elite | Romagnola | Danure Hublo | 3 |
| 58 | Universalsemensales | Salers | TV Big Red | 4 |
| 59 | Bovine Elite | Santa Gertrudis | Gambler II 817 | 4 |
| 60 | Bovine Elite | Senepol | HBC 7115 48K | 4 |
| 61 | Select Sires | Beefmaster | P.D.Q. | 2 |

TABLE 2

DNA Repository (Samples Sequenced for STAT6)

| ID | Source | Breed | Short Name |
|---|---|---|---|
| BA1 | Select Sires | Black Angus | Predestined |
| BA2 | ABS Global | Black Angus | TRIPLE THREAT |
| BA3 | ABS Global | Black Angus | EASY FORTUNE |
| BA4 | ABS Global | Black Angus | CENTER CUT |
| BA5 | Charles Farber | Black Angus | P S Franco 064 157 |
| RA1 | Select Sires | Red Angus | Field Day |
| RA2 | Select Sires | Red Angus | Vigor |
| RA3 | Select Sires | Red Angus | Ho Ho |
| RA4 | Select Sires | Red Angus | Heavenly |
| RA5 | Select Sires | Red Angus | Duke |
| RA6 | Select Sires | Red Angus | Rambler |
| HP1 | Select Sires | Hereford Polled | Formula |
| HP2 | ABS Global | Hereford Polled | JEDI |
| HP3 | ABS Global | Hereford Polled | MASTER DUTY |
| HH1 | ABS Global | Horned Hereford | HR ROBIN HOOD |
| HH3 | Charles Farber | Horned Hereford | CL 1 Domino 0144K 1ET |
| HH4 | Charles Farber | Horned Hereford | HH Advance 249B |
| SR1 | Select Sires | Simmental Red | Autobahn |
| SR2 | Bovine Elite | Simmental Red | ER Americana 537B |
| SR3 | Bovine Elite | Simmental Red | NLC Good A Nuff 33G |
| ST1 | ABS Global | Simmental Traditional | FUTURE MODERATOR |
| ST2 | Universalsemensales | Simmental Traditional | BEL DUTCH 89X |
| ST3 | Bovine Elite | Simmental Traditional | Bar 5 Bernheim 405H |
| CC1 | Select Sires | Charolais Creme | Choice Plus |
| CC2 | Select Sires | Charolais Creme | Sir Prime Time |
| CP1 | ABS Global | Charolais Polled | SILVER EDGE |
| CS1 | ABS Global | Charolais scurred | SENTINAL RULER |
| GR1 | ABS Global | Gelbvieh Red | TOP BRASS |
| GR2 | ABS Global | Gelbvieh Red | TABASCO |
| GR3 | ABS Global | Gelbvieh Red | SIR ARNOLD |
| GR4 | ABS Global | Gelbvieh Red | MODERATOR |
| LB1 | Select Sires | Limousin Black | Equity |
| LR1 | ABS Global | Limousin Red | POLLED MANHATTAN |
| LR2 | ABS Global | Limousin Red | JUSTICE |
| LR3 | Bovine Elite | Limousin Red | EXLR Latigo 029M |
| WG1 | Universalsemensales | Wagyu "A" | BR Fukutsuru 0620 |
| WG2 | Universalsemensales | Wagyu "B" | BR Takazakura 0604 |
| WG3 | Universalsemensales | Wagyu "C" | BR Hirashigotayasu 9645 |
| BR1 | Select Sires | Brangus | Carrarra |
| BR2 | Milton Thomas | Brangus | NMSU 830 |
| BR3 | Milton Thomas | Brangus | CCR INTEGRITY F386F2 |
| BR4 | Milton Thomas | Brangus | John Wayne 44L |
| BH1 | Select Sires | Brahman | 852/5 |
| BH2 | Select Sires | Brahman | Rojo Bueno |
| BH3 | Bovine Elite | Brahman | BB Mr Sting-Ray 10/0 |
| BH4 | Milton Thomas | Brahman | 6X Sunland 874 |
| BH5 | Milton Thomas | Brahman | SRW MR. FLYING W 831 |
| BH6 | Milton Thomas | Brahman | JDH MR. SALLUTO MANSO 300/2 |

Example 2

SNP Discovery Platform Using Resequencing Strategy

A strategy for SNP discovery was developed for this project. SNPs were identified by resequencing candidate genes in panels of 48 animals (9 breeds) from the discovery panel. See, Table 2. A genomic reference sequence was assembled from GenBank sequences (genomic, mRNA and ESTs) and from Ensembl bovine genome sequences. The sequence was annotated to identify exons, introns, 2000 bp of the promoter and 1000 bp of the 3' untranslated region. Repetitive and low-complexity sequences were masked with RepeatMasker to prevent sequencing repetitive regions of the genes.

The sequencing project was outsourced to SeqWright (Houston, Tex.). SeqWright provided a full service of automated sequencing with a brief annotation and SNP discovery. Sequence traces were downloaded from SeqWright and resembled at UCDavis using software CodonCode Aligner to notate and discover SNPs.

The genotype of the sequenced animals for each gene were analyzed using haploview software (on the worldwide web at broad.mit.edu/mpg/haploview/) to define haplotypes and to choose a minimal information subset of Tag SNPs for genotyping. In addition, computational algorithms were used, for example, SIFT and PolyPhen, to predict the impact of nucleotide or amino-acid substitutions on protein structure and function. These algorithms were useful to flag unique mutations of interest.

Example 3

Identify SNPs in STAT6

Using a bioinformatics-based method to identify sequence homologies between bovine microsatellites (Farber and Medrano 2003, Animal Genetics 34, 11-18), and gene sequencing it was demonstrated that microsatellite ETH10 is located within the first exon of the bovine STAT6 gene. ETH10 has been strongly associated in earlier work with marbling in Wagyu cattle (Barendse, Australia), with a suggestion of RDH5 as being the causative gene.

It was proposed that the association between ETH10 and marbling is either due to the repeat itself or polymorphisms with the STAT6 gene, which alter its function. Earlier, 3 SNPs between different breeds of dairy cattle were identified. 39 SNPs across the complete gene have been identified overall, in the 48 animals breed panel. FIG. 1 shows an annotated sequence of the bovine STAT6 gene and the position of Tag SNPs statistically correlated with economically important traits in beef cattle. Table 3 shows flanking sequences of individual SNPs.

After defining haplotypes and regions of linkage disequilibrium in the STAT6 genes of the selected animals, identified 15 Tag SNPs were identified. Tag SNPs are a minimal information subset of SNPs that capture all the variation of a gene in defined populations. Three of the SNPs, 14636, 16084 and 19597, are statistically correlated with economically important carcass and feedlot traits in beef cattle. See, Table 4. Four of the SNPs, 10922, 14257, 24000 and 25999, are fixed in *Bos taurus* and in *Bos indicus* and therefore find use in genotypically distinguishing these two species.

The association analysis was performed using the Golden Helix Regression Analysis Module from Helixtree software. The Golden Helix Regression Module was used to test allelic associations with phenotypic variables. The Regression Module supports both linear and logistic regression. A stepwise regression was used to find confounding phenotypic variables, regressors were fixed, and then a search for significantly associated SNPs was performed. This regression approach is particularly powerful for overcoming the difficult challenges of population stratification. Permutation testing increased the flexibility of the analysis. Table 4 shows the significant results for the association analysis.

TABLE 3

Sequences Flanking SNPs in STAT6 Gene

| PolyID | Species | Context |
|---|---|---|
| 14636 SEQ ID NO: 2 | *Bos taurus* | GGGTGGGAGTGGGGGAAAGTCTGGCCC CTCGCTGTCGGAGGATGGAGTAGGGGA GATTTGAAGGCAGGGCCATGCCAGGAA GCTGGTCACTCTTCCTAATCTAGGGGA TATGGAGGAAAGGGGAGCTGCCTCTGA CTTAGGGATCACCTC[C/G]GTCCCCG TAGGGTAGAGATAGAGGTCAAAGGTCT GAGCACCCTGAGAAACAGGAGAGAAAG AGGGAAGAGAGGAATGGAGTCCTCCCT TGAGTTTGAAACACAAACCAAAAGGTG CCCCACCCCAAGGTGGGTGTAGAGAAA GGTCTAT |
| 16084 SEQ ID NO: 3 | *Bos taurus* | ATTGGCAGCATGGAGTCTTAGCCACTG GATCACCAGAGAAGTTCCGAGGGGAGG TTTCCTGCCAACAGAATCAGAGCTACA ACCCACATTCTCTGCCTTCTCTCAGAG AGCTTTCCCTACTGCCCCATTGCCCCT GTCTCTTACCCTCT[C/A]CCCTCCCC CAACTGGCTGCAGCTCAGCTCTTCCCA CTCCATTACCCCCATGCCTACTGTTGA AGAAAATACCTTGTTTCAGGCTTTGGC CAAAGAGGTTCCTGGTTTGATATAGTC TGRCTGAGAGTTGTGGTGCTGATGGTC TCTGAAA |
| 19597 SEQ ID NO: 4 | *Bos taurus* | TGTGAGAGCCTGGTGGACATTTATTCC CAGCTGCAGCAGGAGGTGGGGGCAGCT GGTGGGGAGCTTGATCCCAAGACCCGG GCAGCGCTGATTAGCCGACTGGATGAA GTCCTGCGCACACTCGTCACCAGGTAT GAGCCCCCCTGCCTG[G/A]TGGAGAG CAGACCCCAAGGAAACAGGAGGGTCAG AGTTGTGGTGGGGGGAGGGGCAGTGGC GCCCAGAGGGACCCAGCTGTTCACTTC CCTGTGTCTTCCTTACTCCTCCCAGCT CTTTCCTGGTGGAAAAGCAGCCCCCCC AGGTTCTG |
| 10922 SEQ ID NO: 5 | *Bos taurus/ indicus* | AAGTGAAACAAATTTCATTAGACACTA CTTATCCTTACTTTGTGTCATGCATTC TGGTATTTTTTATTGTATTCTACTTTG TTTTTAAATACTGGTGGTCAAGGCTCA CTGTGATGGGTTGAACTCTGCCTCTCA AAAATTTATATATTA[A/G]TATGTTG AAATCACATATCCCTCAAAAATTCATA TTCATAGGAGGTACCCTCAGTCCCTCA GAATGTGACCTTATTCAGATATAGGGT CTTTACAGAGGAAATCTTTAGGGTGGG CCCTAATCCAATATGACTGATGTCTTT AGAAAAAG |
| 14257 SEQ ID NO: 6 | *Bos taurus/ indicus* | GCTGGTGGCTGGTGTTACTGAGTTTCG GCAGTTTCGAAATATCAGAGGAATCTG GAGTGGGTACAGGCCCAGCACTTGCCC CGCTCCTCCCCAACATGGGTCACTTTT TCCACACACCCCATCCCCCGCAATCCA GGGACGTGTTAAGGC[C/A]GGGGAAG GAGGGCAAGGAGGTGCCCCTCTGCCCT CTGGGTTGGGGGGAAGTGGCCGCCCCT CCCTATAGAAAACTGATGGCAGGGGGC AGTGGATCCTCCACAGACCCCTATCCG GGCCCCCCACAAAGGTTCCTCTTCAAG GGTGTGGC |
| 24000 SEQ ID NO: 7 | *Bos taurus/ indicus* | CGGGGCTGGCAGCTCTGACTCCTTCTG TGGTCCGCCTCCTCCCTGCTCCTGGTT GCCCCCACCCCACCTGCTGTGTGTCAT CCCTGACTTCTTCCTCCATTGTCATTT CCCTGCTTCTGGACCCTGCCCATCATC CATGCTCACCTTTTC[T/C]AGCTCCC TTCCTCCCTAACCCGGAAGCATTCCAT GGCTCTCCTTTCCTCCCCACAATAGCT GAGCAGATGGGTAAGGATGGCAGGGGT TATGTCCCAGCTACAATCAAGATGACT GTGGAAAGGTGAGTGTGCTGGTGTGGA TGGAGGGC |
| 25999 SEQ ID NO: 8 | *Bos taurus/ indicus* | TGAGCTCAAGCTCCTCATTCATYCCCR GCCTCAACCCCACCCTGACCCCCCCCA CCACCTCATTTACTTCTCTGGGGCTGG CAGGGGCCTGCTGCCGTGCCCACCTCA GGATCATGCTGTGTCCAGCCCTGAGCC CTTGCTCTGCTCAGA[T/C]GTGACCA TGGCAGAAGACAGCTGCCTGAACCAGC CGGTGGGAGGGTTCCCTCAAGGCACCT GGTGAGTGTCAGCCTGGGGGTGGAGGC TGGGTGGGGGGTTGCGGTGTGGGTACC ATGCCTATCCCACTGCTTCTCCACTCC TCTCTGCA |

TABLE 4

EFFECT OF STAT6 GENOTYPES ON PERFORMANCE AND CARCASS TRAITS IN BEEF CATTLE

| STAT6 SNP 16084 | AA | AC | CC | P-value[b] | Additive Effect | Dominace Effect | Allele Subs. Effect[a] |
|---|---|---|---|---|---|---|---|
| Back Fat | 0.59 ± 0.07 | 0.51 ± 0.01 | 0.47 ± 0.005 | 0.00030 | 0.12 ± 0.06<br>P = 0.0004 | −0.02 ± 0.04<br>P = 0.001 | 0.08<br>P = 0.0002 |
| Calculated yield grade | 3.1 ± 0.2 | 2.82 ± 0.05 | 2.66 ± 0.02 | 0.0031 | 0.44 ± 0.1<br>P = 0.011 | −0.06 ± 0.02<br>P = 0.013 | 0.32<br>P = 0.0009 |
| Cutability | 49.5 ± 0.6 | 50.1 ± 0.1 | 50.46 ± 0.05 | 0.0029 | −0.96 ± 0.3<br>P = 0.011 | 0.12 ± 0.1<br>P = 0.013 | −0.76<br>P = 0.0087 |

| STAT6 SNP 19597 | AA | AG | GG | P-value[b] | Additive Effect | Dominace Effect | Allele Subs. Effect[a] |
|---|---|---|---|---|---|---|---|
| Hot carcass weight | 762 ± 4 | 754 ± 3 | 744 ± 4 | 0.0019 | 18 ± 4<br>P = 0.002 | 1 ± 4<br>P = 0.008 | 18.26<br>P = 0.002 |
| Dry matter intake | 2945 ± 29 | 2909 ± 19 | 2825 ± 23 | 0.0018 | 120 ± 24<br>P = 0.00013 | 24 ± 22<br>P = 0.0016 | 120.45<br>P = 0.001 |
| Days on feed | 138 ± 1 | 141.5 ± 1 | 144 ± 1 | 0.00088 | −6 ± 1<br>P = 0.0007 | 0.5 ± 1<br>P = 0.003 | 6.12<br>P = 0.0007 |

| STAT6 SNP 14636 | CC | CG | GG | P-value[b] | Additive Effect | Dominace Effect | Allele Subs. Effect[a] |
|---|---|---|---|---|---|---|---|
| BFAT RATE | 0.0131 ± 0.0004 | 0.0126 ± 0.0002 | 0.0117 ± 0.0001 | 2.34E−07 | 0.0014 ± 0.0002<br>P = 0.0032 | 0.0002 ± 0.0001<br>P = 0.0076 | 0.0015<br>P = 1.6E−6 |
| Days on feed | 136 ± 1 | 139.8 ± 1 | 144 ± 1 | 1.51E−05 | −8 ± 1<br>P = 2.6E−5 | −0.2 ± 1<br>P = 0.0001 | −8.2<br>P = 2.6E−5 |
| Average daily gain | 3.83 ± 0.02 | 3.70 ± 0.03 | 3.61 ± 0.02 | 4.52E−05 | 0.22 ± 0.02<br>P = 0.002 | −0.02 ± 0.02<br>P = 0.01 | 0.19<br>P = 0.0001 |

[a]Allele substitution effect estimated by regression of phenotype on genotype dummy variables. The effect represents the regression coefficient (equal to the absolute effect) of genotype.
[b]P value from overall F-test.

Example 4

Detection of SNP ID 14257 Using PCR-RFLP Protocol

This example shows a PCR/RFLP genotyping assay for STAT6 SNP ID 14257. Detecting polymorphisms at SNP ID 14257 differentiates between *Bos taurus* and *Bos indicus* species.

The nucleotide at SNP ID 14257 of the bovine STAT6 gene is PCR amplified from bovine genomic DNA template using forward primer 5'-GGGCCTCTGACTACCAATGT-3' (SEQ ID NO:9) and reverse primer 5'-CCACACCCTTGAAGAGGAAC-3' (SEQ ID NO:10).

The PCR amplification conditions are as follows:

| | |
|---|---|
| dH$_2$O | 17.3 μl |
| 10x PCR buffer | 2.5 μl |
| 50 mM MgCl$_2$ | 1.5 μl |
| 10 mM dNTPs | 0.5 μl |
| 10 pmol/μl Primers | 1 μl each |

-continued

| | |
|---|---|
| Taq polymerase 5U | 0.2 μl |
| DNA 50 ng | 1 μl |
| Total Volume | 25 μl |

The PCR reaction is run for 35 cycles: 30 sec. at 94° C.; 30 sec. at 60° C.; and 30 sec. at 72° C. The amplified PCR amplicons (397 bp when uncut) are then subject to restriction endonuclease digestion with MspI. If the bovine is a *Bos taurus*, then the restriction endonuclease digestion produces fragments of 36 bp, 114 bp and 247 bp. If the bovine is a *Bos indicus*, then the restriction endonuclease digestion produces fragments of 361 bp and 36 bp. A representative result is shown in FIG. 3.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for selecting a bovine for decreased back fat thickness, lower calculated yield grade and increased cutability comprising:
   a) obtaining a biological sample from the bovine, determining the genotype of STAT6 at position 150 of SEQ ID NO:3; and
   b) selecting a bovine with a CC genotype at position 150 of SEQ ID NO:3, wherein a CC genotype at position 150 of SEQ ID NO:3 indicates decreased back fat thickness, lower calculated yield grade and increased cutability relative to AC or AA genotypes.

2. The method of claim 1, further comprising determining the genotype of STAT6 at position 151 of SEQ ID NO:4, wherein an AA genotype at position 151 of SEQ ID NO:4 indicates increased hot carcass weight, increased dry matter intake, and fewer days on feed relative to AG or GG genotypes.

3. The method of claim 1, further comprising determining the genotype of STAT6 at position 151 of SEQ ID NO:2, wherein a CC genotype at position 151 of SEQ ID NO:2 indicates increased back fat rate, fewer days on feed, and increased average daily gain relative to CG or GG genotypes.

4. The method of claim 1, wherein the bovine is a *Bos*.

5. The method of claim 4, wherein the bovine is a *Bos taurus*.

6. The method of claim 1, wherein the STAT6 genotype is detected by an amplification reaction using polynucleotides that distinguish between alleles.

7. The method of claim 6, wherein the amplification reaction is selected from the group consisting of polymerase chain reaction (PCR), strand displacement amplification (SDA), nucleic acid sequence based amplification (NASBA), rolling circle amplification (RCA), T7 polymerase mediated amplification, T3 polymerase mediated amplification and SP6 polymerase mediated amplification.

8. The method of claim 1, wherein the STAT6 genotype is detected by hybridization using polynucleotides that distinguish between alleles.

9. The method of claim 1, wherein the STAT6 genotype is detected by sequencing.

10. A method for selecting a bovine for increased hot carcass weight, increased dry matter intake, and fewer days on feed comprising:
    a) obtaining a biological sample from the bovine, determining the genotype of STAT6 at position 151 of SEQ ID NO:4; and
    b) selecting a bovine with an AA genotype at position 151 of SEQ ID NO:4, wherein an AA genotype at position 151 of SEQ ID NO:4 indicates increased hot carcass weight, increased dry matter intake, and fewer days on feed relative to AG or GG genotypes.

11. The method of claim 10, further comprising determining the genotype of STAT6 at position 151 of SEQ ID NO:2, wherein a CC genotype at position 151 of SEQ ID NO:2 indicates increased back fat rate, fewer days on feed, and increased average daily gain relative to CG or GG genotypes.

12. The method of claim 10, further comprising determining the genotype of STAT6 at position 150 of SEQ ID NO:3, wherein a CC genotype at position 150 of SEQ ID NO:3 indicates decreased back fat thickness, lower calculated yield grade and increased cutability relative to AC or AA genotypes.

13. The method of claim 10, wherein the bovine is a *Bos*.

14. The method of claim 13, wherein the bovine is a *Bos taurus*.

15. The method of claim 10, wherein the STAT6 genotype is detected by an amplification reaction using polynucleotides that distinguish between alleles.

16. The method of claim 15, wherein the amplification reaction is selected from the group consisting of polymerase chain reaction (PCR), strand displacement amplification (SDA), nucleic acid sequence based amplification (NASBA), rolling circle amplification (RCA), T7 polymerase mediated amplification, T3 polymerase mediated amplification and SP6 polymerase mediated amplification.

17. The method of claim 10, wherein the STAT6 genotype is detected by hybridization using polynucleotides that distinguish between alleles.

18. The method of claim 10, wherein the STAT6 genotype is detected by sequencing.

19. A method for selecting a bovine for increased back fat rate, fewer days on feed, and increased average daily gain comprising:
    a) obtaining a biological sample from the bovine, determining the genotype of STAT6 at position 151 of SEQ ID NO:2; and
    b) selecting a bovine with a CC genotype at position 151 of SEQ ID NO:2, wherein a CC genotype at position 151 of SEQ ID NO:2 indicates increased back fat rate, fewer days on feed, and increased average daily gain relative to CG or GG genotypes.

20. The method of claim 19, further comprising determining the genotype of STAT6 at position 150 of SEQ ID NO:3, wherein a CC genotype at position 150 of SEQ ID NO:3 indicates decreased back fat thickness, lower calculated yield grade and increase cutability relative to AC or AA genotypes.

21. The method of claim 19, further comprising determining the genotype of STAT6 at position 151 of SEQ ID NO:4, wherein an AA genotype at position 151 of SEQ ID NO:4 indicates increased hot carcass weight, increased dry matter intake, and fewer days on feed relative to AG or GG genotypes.

22. The method of claim 19, wherein the bovine is a *Bos*.

23. The method of claim 22, wherein the bovine is a *Bos taurus*.

24. The method of claim 19, wherein the STAT6 genotype is detected by an amplification reaction using polynucleotides that distinguish between alleles.

25. The method of claim 24, wherein the amplification reaction is selected from the group consisting of polymerase chain reaction (PCR), strand displacement amplification (SDA), nucleic acid sequence based amplification (NASBA), rolling circle amplification (RCA), T7 polymerase mediated amplification, T3 polymerase mediated amplification and SP6 polymerase mediated amplification.

26. The method of claim 19, wherein the STAT6 genotype is detected by hybridization using polynucleotides that distinguish between alleles.

27. The method of claim 19, wherein the STAT6 genotype is detected by sequencing.

* * * * *

SEQUENCE LISTING

<160> NUMBER OF SEQ ID NOS: 44

<210> SEQ ID NO 1
<211> LENGTH: 16800
<212> TYPE: DNA
<213> ORGANISM: Bos taurus
<220> FEATURE:
<223> OTHER INFORMATION: bovine signal transducer and activator of
      transcription 6 (STAT6), interleukin-4-induced

```
         transcription factor (IL-4 Stat) genomic sequence
<221> NAME/KEY: variation
<222> LOCATION: (122)...(122)
<223> OTHER INFORMATION: bovine STAT6 polymorphism allele SNP ID 10922
<221> NAME/KEY: exon
<222> LOCATION: (2778)...(3533)
<223> OTHER INFORMATION: exon E1
<221> NAME/KEY: variation
<222> LOCATION: (3457)...(3457)
<223> OTHER INFORMATION: bovine STAT6 polymorphism allele SNP ID 14257
<221> NAME/KEY: variation
<222> LOCATION: (4189)...(4189)
<223> OTHER INFORMATION: bovine STAT6 polymorphism allele SNP ID 14636
<221> NAME/KEY: variation
<222> LOCATION: (5637)...(5637)
<223> OTHER INFORMATION: bovine STAT6 polymorphism allele SNP ID 16084
<221> NAME/KEY: exon
<222> LOCATION: (6374)...(6511)
<223> OTHER INFORMATION: exon E2
<221> NAME/KEY: exon
<222> LOCATION: (6922)...(7057)
<223> OTHER INFORMATION: exon E3
<221> NAME/KEY: exon
<222> LOCATION: (7322)...(7406)
<223> OTHER INFORMATION: exon E4
<221> NAME/KEY: exon
<222> LOCATION: (7807)...(7946)
<223> OTHER INFORMATION: exon E5
<221> NAME/KEY: exon
<222> LOCATION: (8049)...(8102)
<223> OTHER INFORMATION: exon E6
<221> NAME/KEY: exon
<222> LOCATION: (8274)...(8425)
<223> OTHER INFORMATION: exon E7
<221> NAME/KEY: exon
<222> LOCATION: (9002)...(9130)
<223> OTHER INFORMATION: exon E8
<221> NAME/KEY: variation
<222> LOCATION: (9150)...(9150)
<223> OTHER INFORMATION: bovine STAT6 polymorphism allele SNP ID 19597
<221> NAME/KEY: exon
<222> LOCATION: (9264)...(9452)
<223> OTHER INFORMATION: exon E9
<221> NAME/KEY: exon
<222> LOCATION: (9788)...(9875)
<223> OTHER INFORMATION: exon E10
<221> NAME/KEY: exon
<222> LOCATION: (10002)...(10125)
<223> OTHER INFORMATION: exon E11
<221> NAME/KEY: exon
<222> LOCATION: (10772)...(10864)
<223> OTHER INFORMATION: exon E12
<221> NAME/KEY: exon
<222> LOCATION: (11201)...(11407)
<223> OTHER INFORMATION: exon E13
<221> NAME/KEY: exon
<222> LOCATION: (12596)...(12691)
<223> OTHER INFORMATION: exon E14
<221> NAME/KEY: exon
<222> LOCATION: (12788)...(12923)
<223> OTHER INFORMATION: exon E15
<221> NAME/KEY: exon
<222> LOCATION: (13244)...(13389)
<223> OTHER INFORMATION: exon E16
<221> NAME/KEY: variation
<222> LOCATION: (13553)...(13553)
<223> OTHER INFORMATION: bovine STAT6 polymorphism allele SNP ID 24000
<221> NAME/KEY: exon
<222> LOCATION: (13613)...(13677)
<223> OTHER INFORMATION: exon E17
<221> NAME/KEY: exon
<222> LOCATION: (13783)...(13893)
<223> OTHER INFORMATION: exon E18
<221> NAME/KEY: exon
<222> LOCATION: (14434)...(14525)
<223> OTHER INFORMATION: exon E19
<221> NAME/KEY: exon
<222> LOCATION: (15310)...(15376)
<223> OTHER INFORMATION: exon E20
<221> NAME/KEY: variation
```

<222> LOCATION: (15552)...(15552)
<223> OTHER INFORMATION: bovine STAT6 polymorphism allele SNP ID 25999
<221> NAME/KEY: exon
<222> LOCATION: (15705)...(16584)
<223> OTHER INFORMATION: exon E21/3'UTR

<400> SEQUENCE: 1

```
tatccttact ttgtgtcatg cattctggta ttttttattg tattctactt tgttttttaaa      60
tactggtggt caaggctcac tgtgatgggt tgaactctgc ctctcaaaaa tttatatatt      120
aatatgttga aatcacatat ccctcaaaaa ttcatattca taggaggtac cctcagtccc      180
tcagaatgtg accttattca gatataggt ctttacagag gaaatcttta gggtgggccc       240
taatccaata tgactgatgt ctttagaaaa aggggaaatt tgtgaattcg ctagcagtcc      300
agtagttagg actcagtgct ttcattgccg gggccctggg ttcaacctct ggtcttggaa      360
caggatccta tgtggcttgg caatagaggg gggaaatttg gagacagact tgcatgcagg      420
gagattacca catgaacagg aagatggcta tccacaggcc aaggagagag gcctggaatg      480
agtcctctca gttttcatag ggcaccaacc ctgccaacac actgatcttg ggcttctagc      540
cttcagtagt ctgacagaat gaattccttt ggttggttca aagcaaaaaa atacactcac      600
ctgattgatt tcgtgactca ctgttgggtt gcaacctgca gttcccggac tgcaacattc      660
tttttctct gcttttcctc ctgcattctt cacagccact ggtgggatgg cagggcccgg       720
aggagggtga ggcaagcaag gaaccaactc tcagggtcat gcaagtgggg gtgtcattac      780
cagtagtcta gccaactcca cacttatatg acctgaaggt gagcacctct ccaactcagc      840
atactcagca cctcaccctg acctaggccg tgtcaagtgg gcacaatcct tgtctccgtt      900
tgagaggttg acacacagtc acaaagcttt taagtggagt ttgatccaca tcagatatgc      960
ccataagtcc tctgatgaca tcacagtctc cccgtctgtg caatcagtta gagaagatga     1020
taataaatat tgttttacta cttgtatgtg tttctcacct tcctatcccc caaagcagtc     1080
aaagttaaag actcgagttc atgcctcctc tcctcttgcc aaagttctgg gggacatggc     1140
cctctggaga cccttaggtg gcaaggcctg agtttagtca ctgtctctgg atgtcagcag     1200
gcagagtggg tgccctggag tggacacaga atgcatgtgt tgtgagcacc tttgtgtaca     1260
cattgcgatc gattgtagca ctgccagctg tataaaccca aggacagggt ccccgcctgc     1320
catctccacc ccagctctcc ctcctctcca actggctgcc ttacagacac aataaatata     1380
taagcacaca cctccaacag cctctgcctt tgtggcatta atattactct caaatctggg     1440
gatcctatgt aagatagaga ctcttctgtc tttctcctgc ctggctagtt ctgggacaat     1500
aaaataatgt ctaacgttta ctgtgtacca ggcatcattt gcatgtatta ttgcatttca     1560
ctctcacaac tttgtaagtt aaggctatta tttgctccat tttacagaca acaaaactga     1620
agcacaaata gtaaacagcc cagagttgtg cagctagcac tgttggcagg atctgaaccc     1680
atgcagcctg ctccagggc caagttctta actcctaccc tctgcctggc tgggcactcc     1740
gacctgcacg tacttgccca tccacgtgga tgggagcagg aggagccagg ttctgggaat     1800
cagttgggac accaggggc agcataagcc tggctttggc ccctgagccc agccctgttt      1860
ggggaaagag gagggagta gaaaccgcct cccaccttcc cccagctcct cagagaccat      1920
cctttcccca tactcgtctc tcaggttggg ggcttgaagg tcccttggcc tcctccagct     1980
tttcctccag ccaaagcttc aaaaaccatc cagtagtgac aatgatgact cagaagctga     2040
gcaagctgtg cgtgtgagtg tgtgtccttt tgtgactgca tgtggctctg agtgctgaca     2100
tgtctgtgag cctgcctgtg cgtgtgtgta agcatgtgtg tgtgtgggag ggagtgtcct     2160
```

```
tctggctggg gaagttgtgt acatgcacgt ttatttctgg gtgtgtctct ctgtgtttac    2220
cccagaaaca gataggaact ttgccaaggt tgcacagcag attcatattc aaacttgtcc    2280
cttaggaatc tacaggcagc aactccagct tgccactggc tcctacctgg gtctccggag    2340
tagtacccca tgaggaggtg gcagaaagga ttttcagtcc caggcacccc tggaggccta    2400
caggattgtg agcttcgcgg ccccctcccc cactccctcc catcagtggg tcacgagacc    2460
tctagggcgt tccccaccca gcagggaggg ggaccgagga gtcccagctc cccgccgctt    2520
tcagggtctt ccactggagg gagcgcaggg ccagagggat ttcttttcc agaggcaccc    2580 cccacccggg ggcggggagg ggggagccca gtccctcttg agcccaaacc cccggccctt    2640
gcaagagttt gagtatggga gctgtagttt ggggtggcat gtctctgctt gatattaggt    2700
gactttctgg agaaaagttg attgtttttg aaggggcag agtaagtggg gatcagcctt    2760
tcctccagca tggcgccagg ggccccaag ccccagtcct ggctccccct cccagcccat    2820
gctcccctac tccataccag aggcacacat gctcacccca cttcttcct cttcctcctc    2880 cagcccactt tctcttctct gtgtcgtcag agctccaggg agggacctgg gtagtcggag    2940
aagccggaaa cagagggctg ggcagccac tgcttacact gaagagggag ctgggagag    3000 gattgtgtgt gtgtgtgtgt gtgtgtgtgt gtgtgtgtgt gtgttttatt tttggtggtg    3060
gtggtggagg aggggtgtta gcagggccag tcctgaaccc gctggacaga gctacagacc    3120 catgggcct ggcagagccg gctgagagag ggagacgaca acagaggggt tgccaaggtg    3180
aggggatgcc tccaaggagg gagggtgggg ggcctctgac taccaatgtg ggggggagga    3240
ggggagtgct tttcaggatc ctgcctgggc agaatggatg gtccctaaga aattgtttca    3300 gctgggggctg gtggctggtg ttactgagtt tcggcagttt cgaaatatca gaggaatctg    3360
gagtgggtac aggcccagca cttgccccgc tcctccccaa catgggtcac tttttccaca    3420
caccccatcc cccgcaatcc agggacgtgt taaggccggg gaaggagggc aaggaggtgc    3480
ccctctgccc tctgggttgg ggggaagtgg ccgcccctcc ctatagaaaa ctgatggcag    3540
ggggcagtgg atcctccaca gacccctatc cgggccccc acaaaggttc ctcttcaagg    3600
gtgtggccag ggggtgagcg tgtcccagaa gtagaacctc atggtgcccc agaggagggg    3660
gaatttcccc ctcaaaactg ctccacgctt ggcccggcgg cgtcatggag ttaaccctcc    3720
tggtgcctaa ctggctccgc ctcccgcgc ccctccccgc cccgcccccc gcacacacac    3780
tgggcaactc cgagcagctc ttctgacttc tgatcctgtg gtcccacgat cagaggactc    3840
aggaatctcg ggggttgagg tgaagtttag gccacgaagc ggggctgagg aagatcctgg    3900
acttcccttc cccatgggga agggaacgcg ggccccgccc cccaggcca tggctcctcc    3960 ctccctgtcg gtgttcaagg gggcttacag cagaagatgc ccctggcctg gcaggccgat    4020
tgagccagcc tggttattgg gtgggagtgg gggaaagtct ggcccctcgc tgtcggagga    4080
tggagtaggg gagatttgaa ggcagggcca tgccaggaag ctggtcactc ttcctaatct    4140
aggggatatg gaggaaaggg gagctgcctc tgacttaggg atcacctccg tccccgtagg    4200
gtagagatag aggtcaaagg tctgagcacc ctgagaaaca ggagagaaag agggaagaga    4260
ggaatggagt cctcccttga gtttgaaaca caaaccaaaa ggtgccccac cccaaggtgg    4320
gtgtagagaa aggtctatga gaggaccctg agcaggaggg ggaggattct gcctttggga    4380 gaaagaggt taggggata taggaactgg ggaggagcac ggatctccag aaaaggggcc    4440
tctctgttct ctattccttt gggagtcctg ggagagggga gaagctaacg tgctgcagga    4500
gaacttgggg ctaactgggt tgagggagac ctagggagtt tccaccccca tcctttctgt    4560
```

| | | | | | |
|---|---|---|---|---|---|
| catctctggg | aagagggacg | ttttgagaaa | catgaactga | gagacccctg | gggaaccact | 4620
| ggtttaccca | ctccgccctg | cagtccacct | agatggggag | gcaaccaccc | cctccctatt | 4680
| ctcctacctc | cttgcctctt | gccccctttc | cttctcttcc | ttgtagtcct | ctagcctccc | 4740
| tgcccctctt | ttttgctttt | ctctgaaggc | taattaacct | cacttttttct | ccttcctgag | 4800
| ttctctctac | tcttcctctt | gctccatctc | ctcttcttca | gttctcctcc | catgcccccc | 4860
| tcctcttggg | attatgagat | ctggatccag | aagggatcct | aagggtacag | agtggtggtt | 4920
| tatccccact | tgggttcaga | tcgcttgcag | agtggccttg | gcaagttgga | gaacctcctt | 4980
| gagctcagtt | tctctacctg | taacaggatg | attttatatt | ttaaaaattg | ttgcaagatg | 5040
| ctagtgaggt | aaggcgctca | gtgtaatgcc | ccatacatag | taagtgctta | atgaataata | 5100
| gctattatta | ctctaccatc | ttcttcttcc | tcatctagcc | aggcagtttt | cagattgttt | 5160
| catggaaccc | tggaattttg | agggatttct | ctagggatac | ctttggggtc | cagaggtgga | 5220
| gagagggaag | caagaagtgg | tagaattcca | ggtctaccac | acttgatttc | aacagagaaa | 5280
| ttccaatttt | acataactgg | ctaaaacggt | ctacttcttt | aaaaaatttg | gaaagttcat | 5340
| actttaccca | agcctcatat | tttatagatg | agaagattga | ggtccacgga | ggggaggttt | 5400
| cttttttgttt | atttgttttt | aaaatctttt | gaccatgcca | caggtcatgt | gggatcttag | 5460
| ttccctgatc | agggatttgt | tcccttcatt | ggcagcatgg | agtcttagcc | actggatcac | 5520
| cagagaagtt | ccgaggggag | gttcctgcc | aacagaatca | gagctacaac | ccacattctc | 5580
| tgccttctct | cagagagctt | tccctactgc | cccattgccc | ctgtctctta | ccctctcccc | 5640
| tcccccaact | ggctgcagct | cagctcttcc | cactccatta | cccccatgcc | tactgttgaa | 5700
| gaaaatacct | tgtttcaggc | tttggccaaa | gaggttcctg | gtttgatata | gtctggctga | 5760
| gagttgtggt | gctgatggtc | tctgaaaggg | ctgtctatgg | gaggtccttg | ctgctgttgc | 5820
| tgctgctgct | gcgtcgcttt | agtcgtgtcc | gactctgtgt | gacccatag | gtggcagcca | 5880
| accaggcttc | ccgtccctgg | gattctccag | gaaagaacat | tggagtgggt | tgccatttcc | 5940
| ttctccaatg | catgtaaatg | aaaagtgaaa | gtgaagtcgc | tcagtcgtgt | ccaactctag | 6000
| cgaccccatg | gactgcagcc | taccaggctc | ctccatccat | gggttttct | aggcaaaagt | 6060
| actggagtgg | ggtgccattg | ccttctcctg | ggaggtcctt | ggctgcccga | aaaggtcaac | 6120
| ttccaaataa | ccttgttctt | tttcttcagt | gttaatgtca | gtcgctcagt | catgtccgag | 6180
| tctcacaacc | ccacgcactg | tagtccacca | agctcctctg | tgtgtggaat | tcttcaggca | 6240
| agaatactag | ggtggctttg | ccattccttt | ctctaggaga | tcttcctgac | ccaggaatca | 6300
| aacccaggtc | tcctgcattg | caggcagatt | ctttactttc | tgaactacca | gggaagccct | 6360
| cttttttcttc | aggcaccctc | caaacccag | atcatgtctc | tgtggggtct | ggtctccaaa | 6420
| atgcccccag | aaaaactgca | gcggctctat | gtcgactttc | ctcaacacct | gcggcatctc | 6480
| ctgggtgact | ggctggagaa | ccagccctgg | tgagtcctgg | ctgcccccca | tcagtccccc | 6540
| agggcctccc | ccacctacct | gccttctcat | taggttttat | tcatcccatt | ttgagacttg | 6600
| ggactcatta | ttgtacatgc | agtggtccag | atttagccag | gagtctgtac | cgcatcaacc | 6660
| agactacggc | gtgttgacat | atggagttcc | tcaccccctt | aggaacctga | gccaaagagg | 6720
| agggaggtca | gagctgggcc | aagggcacca | cccacaacag | ctggaaaatt | gggggaacaag | 6780
| gggcacagct | gaggactacg | gagggcctgg | atggaggata | agaggaggaa | ggagctgctg | 6840
| agctgtttgc | tgtggggtga | agggggcagta | gagtcgagga | agccctgacc | tgaggtggcc | 6900
| tcatcctgat | cttcctgcag | ggaattcctt | gtcggctcag | acaccttctg | ctgcaacatg | 6960

```
gccagcgccc tactttctgc cactgtccag cgccttcagg cctcagccgg agagcagggg    7020
gaggggaaca ccatcttgca acacatcagc actctggagg tgggcgcagg agggagggga    7080
cagggccagg gtggggcctg agctggggt gagcattgga tgctggaagg gaattggtat     7140
tcctctggtt agctgttagc tagcaggcaa attagattct aaaagcatgc aaatgcatgc    7200
aaacttctgg agtctatgat tgtgcggcct tttagttcat gtgtgaatgg ggaggggat     7260
tggtgaggga gaatgacatg ggtaagagca aggctaaccc catctaccac tcttcatttc    7320
tagaccattt atcagaggga cccctgaag ctggtggcca cttgcagaca catacttcaa     7380
ggtgaaaaaa aagctgttat ggagcaggta ttgtgatacc ccacctccca ccccaactca    7440
accctgggaa actttagcct gagccattag aaactagaag ggatttgaac ttcaggaaaa    7500
gctcagtgtt ctaggtccaa gatgatcaaa ggaggttcct ggggtcagag tgagccccaa    7560
gttaagctca gagaagcttc caatgaggaa ctgagggtag tgagaggtct ggggcaagtg    7620
atacagagct gttatctcca gaagattcca aaatgtcaag aagaactgtc aaggaagaga    7680
aaggagcgag acaagggaag tggtctatt tctgcagagc atggcagtgg gcaccccttt    7740
agggagtgga ggctgaggga aaagggatgg acagagtgtt tcacctgttg cctgtccttc    7800
cttgcagttc caccacctgc caatgtcctt ccactggaag caggaggaac tcaagtttaa    7860
cacagtccta cggaggctgc agcaccgggc cggggagacc cgccttctcc gggaggccct    7920
gcagcctgga gctgaggctg ccaaggtgg gattctgggg agtgtgtggg agtgaccccc     7980
tcttggatct caaccctgat tgaacctctt aaatatatct gcaccccgat ttttgccct     8040
accctcagtg tctttgcaca gcttgataga aacgcctacc aacgggactg ggccaagtga    8100
ggtgagtaat ggactgagat gtggagactg agctcaaagt gcagacttg agggtctcag    8160
atctgtggag ggatggtgag tagacctctg agaggtgaga aagggaggct taccctccag    8220
agctgggcaa agaggaagcg tgtggctccg gctcaggccc cacctgccca caggccctgg    8280
tcacgctgct gcaggagact gttggtgagc tggaagctgc tcaggctctg gtgctgaaga    8340
ggatccagat atggaagcgg caacagcagc tggcagggaa tggtgcaccc tttgaggaga    8400
gcctggctcc actacaagag aggtggggaa gggctgacag ggaagcggga tgcgctgggg    8460
gtggacatct gctctccctg ctggaggtgt gagagagaga aaccaggcca gagggtctcg    8520
gggtgggcca agacttggag aagccagttc agcagagcc acccatactg ttgttcaggt     8580
catgtcttgc acacacgcac caggctgacc cggcatgagc aggcattcct ccaatctata    8640
cttttctctt cgagctccat gcccagaggg ctggaagtc cttttcgttt attggcaggg     8700
tatctttcaa tatgcgcaaa agcatcgtgc gtgctggcct cagacctggg tatcagaccc    8760
ctggggaaag ggcagctcgt ttcaacagag cttccaggca ctaagcggga accttgcccc    8820
agagccaagg cgcgtcccac caccccttca gccccagtgc cttgctgtca cacccactgc    8880
tcatccctaa ccctccacac acactatcct gctttcttcc tggggttgagg ggtgaggggc    8940
ggtctgggcc gggagcaggc tggaagactg cgcccctga ccacggtcct ggccccaggt     9000
gtgagagcct ggtggacatt tattcccagc tgcagcagga ggtgggggca gctggtgggg    9060
agcttgatcc caagacccgg gcagcgctga ttagccgact ggatgaagtc ctgcgcacac    9120
tcgtcaccag gtatgagccc ccctgcctgg tggagagcag accccaagga aacaggaggg    9180
tcagagttgt ggtgggggga ggggcagtgg cgcccagagg gacccagctg ttcacttccc    9240
tgtgtcttcc ttactcctcc cagctctttc ctggtgaaaa agcagccccc ccaggttctg    9300
aagactcaga ccaagttcca ggccggagtt cgattcctgc tgggcctgag gttcctgggg    9360
```

-continued

| | | | | |
|---|---|---|---|---|
| gccccagcca | agcctccgct | ggtcagggcc | gacatggtca | cggagaagca ggcgagggag | 9420 |
| ctgagcatgc | cccaggggcc | cggagctgga | gcgtaagctg | gggctggaga gggcctgagt | 9480 |
| gggagatgga | ggccagaggg | gcctgggaga | ccggcacagt | gaaggggggct gggtgatgat | 9540 |
| ggggaggcag | ggccatgggg | tatggggggcc | ctgtataaca | gtcaagcgag aggaagggga | 9600 |
| gggacccacc | agtgctggaa | tggggtggaa | gcgtcctgat | ttggctaaga tgggggttc | 9660 |
| tccctcaaga | acccaagtag | ggagatagag | attagggacc | aatagtctag gccattcacc | 9720 |
| tgtgcactca | agctcctgcc | actcctgggc | caatcgggat | gagcccctct ctgacttgcc | 9780 |
| ctggcagaga | aagcaccgga | gaaatcatca | acaacaccgt | gcccctggag aacagcattc | 9840 |
| ctgggaactg | ctgctctgcg | ctgttcaaga | acctggtgag | aggcctttgg ggagcagtgg | 9900 |
| gtgggcgtcc | tcaggccagg | caagtgtcct | cgagagggtg | tggggagccc aggagaagca | 9960 |
| gtttctgcct | tcatcctcct | cgctctcacc | ccttccccca | gcttctgaag aaaatcaagc | 10020 |
| ggtgtgagcg | gaagggcacc | gagtctgtca | ccgaggagaa | gtgcgctgtg ctcttctcca | 10080 |
| ccagcctcac | gcttggccct | aacaaactcc | ccatccagct | ccaggtgagc ttgagtccca | 10140 |
| ggtgccctgg | ccacacacgg | aggcctggat | cctcattcct | catgaatgcc ctgtaccctg | 10200 |
| tgggtctggg | gttcacgcat | gtgggggctc | cagcgggagt | ggggaggacg agaactcaag | 10260 |
| tgcacactcc | agggaatgac | ggtgtgtgtt | attgcatatg | gccctgtggg actgtgtccc | 10320 |
| agttttttgca | ataagaacta | ttttccttag | ccatgccaat | ggctaaggca ttgaagcact | 10380 |
| tttcttagac | cagggcactg | ttttaagtca | tacgcatgca | cacacacaca gggtttgcac | 10440 |
| agttaacatt | atgagggagt | tattcttact | agcctcattt | tacagatgag aacactgaaa | 10500 |
| cacagagatt | gagtacttag | cctgggtcac | acagctcctg | aatgttggag ctggtatttg | 10560 |
| aaacctggag | gtctgactcc | atagcactga | ctcctcacca | catctcagca gggaggccat | 10620 |
| aattcagctt | cagaaagcac | tcgttcacac | accacaaatt | tttaactgtg tggtgggagt | 10680 |
| tcaggagctt | ccgggtatcc | tcagagccag | ccctctgcag | aggccccttg tcccccagta | 10740 |
| ccaagagctc | cctttcctca | cccgcttcag | gccctgtctc | tgcccctggt ggtcatcgtc | 10800 |
| catggcaacc | aagacaataa | tgccaaagcc | accatcctgt | gggacaatgc cttctctgag | 10860 |
| atggtgagac | aagacccgga | gttgggggga | ggaggggcta | taacctggcg ggtgggtgca | 10920 |
| ggctggtggg | gtggctggta | tgtccacatg | agagtgacca | taactccttc tcatggactt | 10980 |
| tgtttctgtc | cttctgacct | cctttcgtgc | taatcttaac | accgattctg tggtagcacc | 11040 |
| ttagactact | gttggaaaag | caccattttt | cttgggcaga | ctcagggggga caaggctggg | 11100 |
| gagggacagt | cttggggaga | ggggaggat | gcaggcccct | ctgatgagga atggctacgt | 11160 |
| cagcctgagc | ctccctcacc | ttctcccctc | cctcccagg | accgcgtgcc ctttgtggtg | 11220 |
| gctgagcggg | tgccctggga | gaagatgtgt | gaaactctga | acctcaagtt catggctgaa | 11280 |
| gtggggacca | accgggggtt | actcccagag | cacttcctct | tcctggccca gaagatcttc | 11340 |
| aatgacaaca | gcctcagtat | agaggccttc | cagcaccgtt | ctgtgtcctg gtcacagttc | 11400 |
| aacaaggtca | ttcccttgcc | ctttggacct | cccaccccca | agcgcttcat ccctgggggca | 11460 |
| ctcagggcct | ccccaaccctc | tgcccaggaa | ccaaccacta | ggattttcac agtgccctgc | 11520 |
| catgttcatc | aggagggcct | ctgccctggc | ccaggcagga | aaacccttg gctctctggc | 11580 |
| atcccccctag | ttttttgtctg | ggggcccctct | gtcttcccctt | ttgctagtga tttgcatgac | 11640 |
| tcacccagac | tgtgtgtaaa | cacagctttg | attcaaaatg | actttgaccc attgggaaaa | 11700 |
| tagttcttat | tgtaaaaacc | aggacaaaat | cccacaggga | caaatgcaat aacaccagca | 11760 |

```
accatgcgtt gacagcttag gatatgccag attgtacttg agcactatat gtatgctatc   11820
tcacttaatc atcacaatag ctctttaagg taggtactat tacacccatt ttatagagga   11880
tgaaccggct cagagatgtt aagtagtttc tccaaggcct cccagtaagt gaggccatat   11940
ttctgactct tgattttagc taccacattt tactgccccc aaaataaggt ggctcaggac   12000
tggatctgtt acaaaaatag gaaaaaatgg aggtctgagt gtcttggttg aagatcagct   12060
gaatcaatgc tgtcatgtac tgatctcttt tttaaaaaag gaagaaagaa aagcccacac   12120
gaccagagga tgtgttagca aagggaacag gacacttaca tcctgcaaac tgccttctct   12180
ggacaccact tccgccaggc ctcattcagg aggggtggga gcacagtggt tatgaggggg   12240
cccagcccag acttcctgga ctaaatccca gctctgcttt tcactggttg tgtaagaagc   12300
aagttatttg atctttctag gctttcattt cttcatctgt aagatgggat actcatggga   12360
tcttcatcca tagatgtgta aagatcggat acagtaattt atggcaagag cttggactag   12420
tgcctgacac atgggaagct tgagtgtggc cattgtcgtt gatggggtct caggtgcagg   12480
gtggtccctc agtcctgtga ctctgttgtg tcggtactca cagcccagtg gctggcctag   12540
ccaggctccc gctctggccc tcttgtgctc acaccggctc ccctctcccc acaggagatc   12600
ctgctgggtc gtggcttcac cttttggcag tggtttgatg gtgtcctgga tctcaccaaa   12660
cgctgtctcc ggagctactg gtcagaccgg tgagtccctg ccccaggtaa cctgaggatc   12720
tgggcctcca gatcctgctc cacacactac gcccccaccc acaacctctc cttcatcctg   12780
gccaggttga tcattggctt catcagcaaa cagtacgtca ctagccttct tctcaacgag   12840
cctgatggaa ccttcctcct tcgattcagt gactcagaga ttgggggcat caccattgcc   12900
cacgtcatcc gaggccagga tggtgaggtc accccagcca gtcctctgcc tctgtgcctg   12960
tgccctcagg ggtttcttct gagaaaggtc ctggccttct ttgatgccaa ccgtgatctt   13020
caggaagttc ttccttaggt tcaacttctc ttcttccttc tgtggcctaa acttctacct   13080
tctcacttgg agtttggtgg gaatggggac tggtgggacc ctcacaccag ctcttcctct   13140
ccttaccttg gtagattgag aatgagtcca accatcgggg taggttgggg aaggggaatt   13200
aagtctggac agaggggact catggcctca ttccttatgt aggctcccca cagatagaga   13260
atatccagcc attctctgcc aaagacctgt ccattcgctc acttggggac cgaatccggg   13320
acctcgctca gctcaaaaac ctctacccca agaaacccaa ggatgaggct ttccggagcc   13380
actacaaacg tgagctgtga gccggggctg gcagctctga ctccttctgt ggtccgcctc   13440
ctccctgctc ctggttgccc ccaccccacc tgctgtgtgt catccctgac ttcttcctcc   13500
attgtcattt ccctgcttct ggaccctgcc catcatccat gctcaccttt tctagctccc   13560
ttcctcccta acccggaagc attccatggc tctcctttcc tccccacaat agctgagcag   13620
atgggtaagg atggcagggg ttatgtccca gctacaatca agatgactgt ggaaaggtga   13680
gtgtgctggt gtggatggag ggcaggcttg atacttattt gtaagcagga agtgtggcat   13740
caaccccctgg tcagtcacac atgcctcctc ccctcctcca gggaccagcc acttcccacc   13800
ccagagcccc aaatgcctac catggtgccc tcttacgatc ttggaatggc ccctgattcc   13860
tccatgaacc tgcagctcgg cccagatatg gtgtaagaag cttgagagat agaactggga   13920
gtgatctgtg ccagcaggca ttcagcatgg gcatggggga agttggcact gggggttgaa   13980
gtagggaatt tcctttgctt gaaagggatc ccccaacttt cttttaaaaa tagaattta   14040
aaaacctatt ttatttttgg ctctgctggg tcttccttgc tgtgcaggct ttttctctag   14100
ttgaggcgag tgggggctac tctttagttg cggtgcgcag gtttctcatg gcagtgactt   14160
```

```
ttcttgttgc agagcgtggg ctctagggct aatgggcttc agcagttgca gcttctgggc    14220
tctagagcat aggctcagta gctgtggtgc acaggtttag ttgttccatg gcacgtggga    14280
tcttcttgca acaggaatca aacccatgtc tcctgcattg gcaggtggat tctttaccat    14340
tgagccccca gggaagcccc aggattcctg ggtaggggat tgggagtgtc caggagaagg    14400
gctggcctca agagtctgct ttctttcctt aggccccaag tgtacccacc acgctctcac    14460
tccatcccct catatccagc cctccccgg gaagaatcag tcaatatgtt gccagccttc     14520
caggagtaag tggggtcacc tctggggaat gggttgggtc acccctgca gtgggattg      14580 gcacttgtat ttgtgaagag aggctcttca atgagaaaag ggtggcacaa agccaatgcc    14640
tgtgtctctt ctgtccactc cattgagtg ttaatagtta agatccgggt tcaaattcca     14700
gctccaccac ttgctgactt tgggcaagtt acttaactct aatgcctcat ctgtaaaatg    14760
gaataatgat gataataata cctgcttcac aggattattg tgaaggttaa tttgagttag    14820
taatatgtat aaagctaaac atagaaccca gctcctggta agagctatgc aagtattagt    14880
attctctctc ctgcctccta aacctactgt ccttttttctg ttaccttgat ttgtatatat   14940
ttatcattct ggcctggaag tggaatagac atttttgttc tccaggtagc actcaggtgt    15000
ttactgactc tcagtcaaag caggacatct tccccccata ggagttgagg tagaggtggg    15060
atcgtagaac cagcagagtt cagaaattag ctaatgtatc cttcctctgt cccccgcttc    15120
agtccccagt gcatataata acatttatac agagaagagg accaaattca caggtagaaa    15180
tgacttgccc aaggtgatac catcaggatg aggaactgga aatagtttcc ttactcaatg    15240
ggcttgactt tgcaacagct gccctggacc agctttcctt taactgtacc ctcctcttcc    15300
tgcttccaga cctcacctgc cgatgcctcc caacctgagc cagatgagcc tgcccttga     15360 ccaacctcac ccgcagtgag tgaccacccc cgcccccatc ctgagctcaa gctcctcatt    15420
cattcccagc ctcaaccca ccctgacccc cccaccacc tcatttactt ctctggggct      15480
ggcaggggcc tgctgccgtg cccacctcag gatcatgctg tgtccagccc tgagcccttg    15540
ctctgctcag atgtgaccat ggcagaagac agctgcctga accagccggt gggagggttc    15600
cctcaaggca cctggtgagt gtcagcctgg gggtggaggc tgggtggggg gttgcggtgt    15660
gggtaccatg cctatcccac tgcttctcca ctcctctctg cagggtccgt gaagacatgt    15720 tcccgcccctt gttgcctccc actgaacagg accttaccaa gcttctcttg gagggacaag    15780
gggagtcagg gggagggtcc ttgggacccc aaccctcct gcagccctcc ccctatgggc     15840
agtctgggat ctcaatgtcc cacctggacc taagagctaa ccccagttgg tgatcccagc    15900
tggagacgga gcccagagag accgctctcc tgccccacg ggcctgctct gggcatctgc     15960
ccctgctcct gcccaacagc agagagggag ggtgtgtcct cctctcccca cccactccct    16020
gctcaggagg aaaagactgc caggagaagg tacactgggt ggaacatacc tactccttcc    16080
cttccaacac acccctgccc tctcccttcc agatagtgga agggaaattc aggttccaag    16140
tgagacacgc cccaacatga ctgcacaggc agtgcacacg catgtgtgtg tgcgtgcacg    16200
cacatacaca catacacaca cacataccca cacacagagc tctccttgga agatggcact    16260
cagcaggaag agggctggac aagagcacag gtgcgggcaa gaggggggatt tctccgcctg    16320 ccccaagcca gggctcacca ctcactggtg gaaacacgca cgcacgcaca catctgttcc    16380
acacactgag gatggcggta tgggcttagg ccccagccct ggagagatgg gaagcagttc    16440
aggagaccct gggaggaagg tggggtgggg tctgtacatt tggtaacaga gtgtggctttt   16500 gcccagatta aaaaaaagt cccaaccagc tccagattct tgtcagtcaa ctggagactt     16560
```

```
caggatacgt gtgtgagatt gtgcagaagt tcaagggctg agtctgtgta cagccaggtg   16620
aaagcgcatg cacttgggac atgtaatata tggatgtcac acatgttagt tgtatggctt   16680
catagaacat tgatctctct gactttgcct gtgtgacaac acaagttagc aagtatgaga   16740
tactgcacac aaggcccag caagtatgct ggcctctcgg acatatgcta acccaaatgt    16800
```

```
<210> SEQ ID NO 2
<211> LENGTH: 300
<212> TYPE: DNA
<213> ORGANISM: Bos taurus
<220> FEATURE:
<223> OTHER INFORMATION: sequence flanking STAT6 SNP ID 14636

<400> SEQUENCE: 2
gggtgggagt gggggaaagt ctggcccctc gctgtcggag gatggagtag gggagatttg     60
aaggcagggc catgccagga agctggtcac tcttcctaat ctaggggata tggaggaaag    120
gggagctgcc tctgacttag ggatcacctc sgtccccgta gggtagagat agaggtcaaa    180
ggtctgagca ccctgagaaa caggagagaa agagggaaga gaggaatgga gtcctccctt    240
gagtttgaaa cacaaaccaa aaggtgcccc accccaaggt gggtgtagag aaaggtctat    300

<210> SEQ ID NO 3
<211> LENGTH: 300
<212> TYPE: DNA
<213> ORGANISM: Bos taurus
<220> FEATURE:
<223> OTHER INFORMATION: sequence flanking STAT6 SNP ID 16084

<400> SEQUENCE: 3
attggcagca tggagtctta gccactggat caccagagaa gttccgaggg gaggtttcct     60
gccaacagaa tcagagctac aacccacatt ctctgccttc tctcagagag ctttccctac    120
tgccccattg ccctgtctc ttaccctctm ccctccccca actggctgca gctcagctct    180
tcccactcca ttaccccat gcctactgtt gaagaaaata ccttgtttca ggctttggcc    240
aaagaggttc ctggtttgat atagtctgrc tgagagttgt ggtgctgatg gtctctgaaa    300

<210> SEQ ID NO 4
<211> LENGTH: 301
<212> TYPE: DNA
<213> ORGANISM: Bos taurus
<220> FEATURE:
<223> OTHER INFORMATION: sequence flanking STAT6 SNP ID 19597

<400> SEQUENCE: 4
tgtgagagcc tggtggacat ttattcccag ctgcagcagg aggtggggc agctggtggg      60 gagcttgatc ccaagacccg ggcagcgctg attagccgac tggatgaagt cctgcgcaca    120
ctcgtcacca ggtatgagcc cccctgcctg rtggagagca daccccaagg aaacaggagg    180
gtcagagttg tggtggggg aggggcagtg gcgcccagag ggacccagct gttcacttcc     240
ctgtgtcttc cttactcctc ccagctcttt cctggtggaa aagcagcccc cccaggttct    300
g                                                                   301

<210> SEQ ID NO 5
<211> LENGTH: 301
<212> TYPE: DNA
<213> ORGANISM: Bos sp.
<220> FEATURE:
<223> OTHER INFORMATION: sequence flanking STAT6 SNP ID 10922
<220> FEATURE:
<221> NAME/KEY: allele
<222> LOCATION: (151)...(151)
```

<223> OTHER INFORMATION: a = Bos taurus; g = Bos indicus

<400> SEQUENCE: 5

```
aagtgaaaca aatttcatta gacactactt atccttactt tgtgtcatgc attctggtat    60
tttttattgt attctacttt gttttaaat actggtggtc aaggctcact gtgatgggtt   120
gaactctgcc tctcaaaaat ttatatatta rtatgttgaa atcacatatc cctcaaaaat   180
tcatattcat aggaggtacc ctcagtccct cagaatgtga ccttattcag atataggtc   240
tttacagagg aaatctttag ggtgggccct aatccaatat gactgatgtc tttagaaaaa   300
g                                                                  301
```

<210> SEQ ID NO 6
<211> LENGTH: 301
<212> TYPE: DNA
<213> ORGANISM: Bos sp.
<220> FEATURE:
<223> OTHER INFORMATION: sequence flanking STAT6 SNP ID 14257
<220> FEATURE:
<221> NAME/KEY: allele
<222> LOCATION: (151)...(151)
<223> OTHER INFORMATION: c = Bos taurus; a = Bos indicus

<400> SEQUENCE: 6

```
gctggtggct ggtgttactg agtttcggca gtttcgaaat atcagaggaa tctggagtgg    60
gtacaggccc agcacttgcc ccgctcctcc ccaacatggg tcacttttc cacacacccc   120
atccccgca atccagggac gtgttaaggc mggggaagga gggcaaggag gtgcccctct   180
gccctctggg ttgggggaa gtggccgccc ctccctatag aaaactgatg gcaggggca   240
gtggatcctc cacagacccc tatccgggcc ccccacaaag gttcctcttc aagggtgtgg   300
c                                                                  301
```

<210> SEQ ID NO 7
<211> LENGTH: 301
<212> TYPE: DNA
<213> ORGANISM: Bos sp.
<220> FEATURE:
<223> OTHER INFORMATION: sequence flanking STAT6 SNP ID 24000
<220> FEATURE:
<221> NAME/KEY: allele
<222> LOCATION: (151)...(151)
<223> OTHER INFORMATION: t = Bos taurus; c = Bos indicus

<400> SEQUENCE: 7

```
cggggctggc agctctgact ccttctgtgg tccgcctcct ccctgctcct ggttgccccc    60
accccacctg ctgtgtgtca tccctgactt cttcctccat tgtcatttcc ctgcttctgg   120
accctgccca tcatccatgc tcaccttttc yagctccctt cctccctaac ccggaagcat   180
tccatggctc tcctttcctc cccacaatag ctgagcagat gggtaaggat ggcaggggtt   240
atgtcccagc tacaatcaag atgactgtgg aaaggtgagt gtgctggtgt ggatggaggg   300
c                                                                  301
```

<210> SEQ ID NO 8
<211> LENGTH: 301
<212> TYPE: DNA
<213> ORGANISM: Bos sp.
<220> FEATURE:
<223> OTHER INFORMATION: sequence flanking STAT6 SNP ID 25999
<220> FEATURE:
<221> NAME/KEY: allele
<222> LOCATION: (151)...(151)
<223> OTHER INFORMATION: t = Bos taurus; c = Bos indicus -continued

```
<400> SEQUENCE: 8
tgagctcaag ctcctcattc atycccrgcc tcaaccccac cctgaccccc cccaccacct      60
catttacttc tctggggctg gcaggggcct gctgccgtgc ccacctcagg atcatgctgt     120
gtccagccct gagcccttgc tctgctcaga ygtgaccatg gcagaagaca gctgcctgaa    180
ccagccggtg ggagggttcc ctcaaggcac ctggtgagtg tcagcctggg ggtggaggct    240 gggtggggggg ttgcggtgtg ggtaccatgc ctatcccact gcttctccac tcctctctgc   300
a                                                                     301

<210> SEQ ID NO 9
<211> LENGTH: 20
<212> TYPE: DNA
<213> ORGANISM: Artificial Sequence
<220> FEATURE:
<223> OTHER INFORMATION: synthetic bovine STAT6 polymorphism SNP ID
      14257 oligonucleotide forward primer

<400> SEQUENCE: 9
gggcctctga ctaccaatgt                                                  20

<210> SEQ ID NO 10
<211> LENGTH: 20
<212> TYPE: DNA
<213> ORGANISM: Artificial Sequence
<220> FEATURE:
<223> OTHER INFORMATION: synthetic bovine STAT6 polymorphism SNP ID
      14257 oligonucleotide reverse primer

<400> SEQUENCE: 10 ccacacccctt gaagaggaac                                                 20

<210> SEQ ID NO 11
<211> LENGTH: 20
<212> TYPE: DNA
<213> ORGANISM: Artificial Sequence
<220> FEATURE:
<223> OTHER INFORMATION: synthetic bovine STAT6 polymorphism SNP ID
      14636 oligonucleotide forward primer

<400> SEQUENCE: 11
gctggtcact cttcctaatc                                                  20

<210> SEQ ID NO 12
<211> LENGTH: 20
<212> TYPE: DNA
<213> ORGANISM: Artificial Sequence
<220> FEATURE:
<223> OTHER INFORMATION: synthetic bovine STAT6 polymorphism SNP ID
      14636 oligonucleotide forward primer

<400> SEQUENCE: 12
tctgacttag ggatcacctc                                                  20

<210> SEQ ID NO 13
<211> LENGTH: 20
<212> TYPE: DNA
<213> ORGANISM: Artificial Sequence
<220> FEATURE:
<223> OTHER INFORMATION: synthetic bovine STAT6 polymorphism SNP ID
      14636 oligonucleotide reverse primer

<400> SEQUENCE: 13
gacctctatc tctaccctac                                                  20
```

-continued

<210> SEQ ID NO 14
<211> LENGTH: 20
<212> TYPE: DNA
<213> ORGANISM: Artificial Sequence
<220> FEATURE:
<223> OTHER INFORMATION: synthetic bovine STAT6 polymorphism SNP ID
      14636 oligonucleotide reverse primer

<400> SEQUENCE: 14
acctctatct ctaccctacg                                               20

<210> SEQ ID NO 15
<211> LENGTH: 17
<212> TYPE: DNA
<213> ORGANISM: Artificial Sequence
<220> FEATURE:
<223> OTHER INFORMATION: synthetic bovine STAT6 polymorphism SNP ID
      14636 oligonucleotide reverse primer

<400> SEQUENCE: 15
ctctacccta cggggac                                                  17

<210> SEQ ID NO 16
<211> LENGTH: 20
<212> TYPE: DNA
<213> ORGANISM: Artificial Sequence
<220> FEATURE:
<223> OTHER INFORMATION: synthetic bovine STAT6 polymorphism SNP ID
      16084 oligonucleotide forward primer

<400> SEQUENCE: 16
tttccctact gccccattgc                                               20

<210> SEQ ID NO 17
<211> LENGTH: 20
<212> TYPE: DNA
<213> ORGANISM: Artificial Sequence
<220> FEATURE:
<223> OTHER INFORMATION: synthetic bovine STAT6 polymorphism SNP ID
      16084 oligonucleotide forward primer

<400> SEQUENCE: 17
tcagagagct ttccctactg                                               20

<210> SEQ ID NO 18
<211> LENGTH: 17
<212> TYPE: DNA
<213> ORGANISM: Artificial Sequence
<220> FEATURE:
<223> OTHER INFORMATION: synthetic bovine STAT6 polymorphism SNP ID
      16084 oligonucleotide forward primer

<400> SEQUENCE: 18
cctgtctctt accctct                                                  17

<210> SEQ ID NO 19
<211> LENGTH: 20
<212> TYPE: DNA
<213> ORGANISM: Artificial Sequence
<220> FEATURE:
<223> OTHER INFORMATION: synthetic bovine STAT6 polymorphism SNP ID
      16084 oligonucleotide reverse primer

<400> SEQUENCE: 19
taatggagtg ggaagagctg                                               20

<210> SEQ ID NO 20
<211> LENGTH: 20

-continued

```
<210> SEQ ID NO 20
<211> LENGTH: 20
<212> TYPE: DNA
<213> ORGANISM: Artificial Sequence
<220> FEATURE:
<223> OTHER INFORMATION: synthetic bovine STAT6 polymorphism SNP ID
      19597 oligonucleotide forward primer

<400> SEQUENCE: 20
cacactcgtc accaggtatg                                              20

<210> SEQ ID NO 21
<211> LENGTH: 15
<212> TYPE: DNA
<213> ORGANISM: Artificial Sequence
<220> FEATURE:
<223> OTHER INFORMATION: synthetic bovine STAT6 polymorphism SNP ID
      19597 oligonucleotide forward primer

<400> SEQUENCE: 21
gagcccccct gcctg                                                   15

<210> SEQ ID NO 22
<211> LENGTH: 20
<212> TYPE: DNA
<213> ORGANISM: Artificial Sequence
<220> FEATURE:
<223> OTHER INFORMATION: synthetic bovine STAT6 polymorphism SNP ID
      19597 oligonucleotide reverse primer

<400> SEQUENCE: 22
aactctgacc ctcctgtttc                                              20

<210> SEQ ID NO 23
<211> LENGTH: 15
<212> TYPE: DNA
<213> ORGANISM: Artificial Sequence
<220> FEATURE:
<223> OTHER INFORMATION: synthetic bovine STAT6 polymorphism SNP ID
      19597 oligonucleotide reverse primer

<400> SEQUENCE: 23
ggggtctgct ctcca                                                   15

<210> SEQ ID NO 24
<211> LENGTH: 20
<212> TYPE: DNA
<213> ORGANISM: Artificial Sequence
<220> FEATURE:
<223> OTHER INFORMATION: synthetic bovine STAT6 polymorphism SNP ID
      10922 oligonucleotide forward primer

<400> SEQUENCE: 24
tgtgatgggt tgaactctgc                                              20

<210> SEQ ID NO 25
<211> LENGTH: 25
<212> TYPE: DNA
<213> ORGANISM: Artificial Sequence
<220> FEATURE:
<223> OTHER INFORMATION: synthetic bovine STAT6 polymorphism SNP ID
      10922 oligonucleotide forward primer

<400> SEQUENCE: 25
ctgcctctca aaatttata tatta                                         25

<210> SEQ ID NO 26
<211> LENGTH: 20
<212> TYPE: DNA
<213> ORGANISM: Artificial Sequence
```

```
<220> FEATURE:
<223> OTHER INFORMATION: synthetic bovine STAT6 polymorphism SNP ID
      10922 oligonucleotide reverse primer

<400> SEQUENCE: 26
gggtacctcc tatgaatatg                                              20

<210> SEQ ID NO 27
<211> LENGTH: 21
<212> TYPE: DNA
<213> ORGANISM: Artificial Sequence
<220> FEATURE:
<223> OTHER INFORMATION: synthetic bovine STAT6 polymorphism SNP ID
      10922 oligonucleotide reverse primer

<400> SEQUENCE: 27
gggatatgtg atttcaacat a                                            21

<210> SEQ ID NO 28
<211> LENGTH: 20
<212> TYPE: DNA
<213> ORGANISM: Artificial Sequence
<220> FEATURE:
<223> OTHER INFORMATION: synthetic bovine STAT6 polymorphism SNP ID
      14257 oligonucleotide forward primer

<400> SEQUENCE: 28
tttttccaca caccccatcc                                              20

<210> SEQ ID NO 29
<211> LENGTH: 15
<212> TYPE: DNA
<213> ORGANISM: Artificial Sequence
<220> FEATURE:
<223> OTHER INFORMATION: synthetic bovine STAT6 polymorphism SNP ID
      14257 oligonucleotide forward primer

<400> SEQUENCE: 29
gggacgtgtt aaggc                                                   15

<210> SEQ ID NO 30
<211> LENGTH: 19
<212> TYPE: DNA
<213> ORGANISM: Artificial Sequence
<220> FEATURE:
<223> OTHER INFORMATION: synthetic bovine STAT6 polymorphism SNP ID
      14257 oligonucleotide reverse primer

<400> SEQUENCE: 30
acttcccccc aacccagag                                               19

<210> SEQ ID NO 31
<211> LENGTH: 15
<212> TYPE: DNA
<213> ORGANISM: Artificial Sequence
<220> FEATURE:
<223> OTHER INFORMATION: synthetic bovine STAT6 polymorphism SNP ID
      14257 oligonucleotide reverse primer

<400> SEQUENCE: 31
ttgccctcct tcccc                                                   15

<210> SEQ ID NO 32
<211> LENGTH: 20
<212> TYPE: DNA
<213> ORGANISM: Artificial Sequence
<220> FEATURE:
<223> OTHER INFORMATION: synthetic bovine STAT6 polymorphism SNP ID
```

24000 oligonucleotide forward primer

<400> SEQUENCE: 32
tcatttccct gcttctggac						20

<210> SEQ ID NO 33
<211> LENGTH: 23
<212> TYPE: DNA
<213> ORGANISM: Artificial Sequence
<220> FEATURE:
<223> OTHER INFORMATION: synthetic bovine STAT6 polymorphism SNP ID
      24000 oligonucleotide forward primer

<400> SEQUENCE: 33
ccatcatcca tgctcacctt ttc					23

<210> SEQ ID NO 34
<211> LENGTH: 20
<212> TYPE: DNA
<213> ORGANISM: Artificial Sequence
<220> FEATURE:
<223> OTHER INFORMATION: synthetic bovine STAT6 polymorphism SNP ID
      24000 oligonucleotide reverse primer

<400> SEQUENCE: 34
atggaatgct tccgggttag						20

<210> SEQ ID NO 35
<211> LENGTH: 16
<212> TYPE: DNA
<213> ORGANISM: Artificial Sequence
<220> FEATURE:
<223> OTHER INFORMATION: synthetic bovine STAT6 polymorphism SNP ID
      24000 oligonucleotide reverse primer

<400> SEQUENCE: 35
agggaggaag ggagct						16

<210> SEQ ID NO 36
<211> LENGTH: 20
<212> TYPE: DNA
<213> ORGANISM: Artificial Sequence
<220> FEATURE:
<223> OTHER INFORMATION: synthetic bovine STAT6 polymorphism SNP ID
      25999 oligonucleotide forward primer

<400> SEQUENCE: 36
cctcaggatc atgctgtgtc						20

<210> SEQ ID NO 37
<211> LENGTH: 17
<212> TYPE: DNA
<213> ORGANISM: Artificial Sequence
<220> FEATURE:
<223> OTHER INFORMATION: synthetic bovine STAT6 polymorphism SNP ID
      25999 oligonucleotide forward primer

<400> SEQUENCE: 37
cccttgctct gctcaga						17

<210> SEQ ID NO 38
<211> LENGTH: 20
<212> TYPE: DNA
<213> ORGANISM: Artificial Sequence
<220> FEATURE:
<223> OTHER INFORMATION: synthetic bovine STAT6 polymorphism SNP ID
      25999 oligonucleotide reverse primer

```
<400> SEQUENCE: 38
tggttcaggc agctgtcttc                                               20

<210> SEQ ID NO 39
<211> LENGTH: 15
<212> TYPE: DNA
<213> ORGANISM: Artificial Sequence
<220> FEATURE:
<223> OTHER INFORMATION: synthetic bovine STAT6 polymorphism SNP ID
      25999 oligonucleotide reverse primer

<400> SEQUENCE: 39
ttctgccatg gtcac                                                    15

<210> SEQ ID NO 40
<211> LENGTH: 847
<212> TYPE: PRT
<213> ORGANISM: Bos taurus
<220> FEATURE:
<223> OTHER INFORMATION: bovine signal transducer and activator of
      transcription 6 (STAT6), interleukin-4-induced
      transcription factor (IL-4 Stat)

<400> SEQUENCE: 40
```

| Met | Ser | Leu | Trp | Gly | Leu | Val | Ser | Lys | Met | Pro | Pro | Glu | Lys | Leu | Gln |
|-----|-----|-----|-----|-----|-----|-----|-----|-----|-----|-----|-----|-----|-----|-----|-----|
| 1 | | | | 5 | | | | | 10 | | | | | 15 | |

| Arg | Leu | Tyr | Val | Asp | Phe | Pro | Gln | His | Leu | Arg | His | Leu | Leu | Gly | Asp |
|---|---|---|---|---|---|---|---|---|---|---|---|---|---|---|---|
| | | | 20 | | | | | 25 | | | | | 30 | | |

| Trp | Leu | Glu | Asn | Gln | Pro | Trp | Glu | Phe | Leu | Val | Gly | Ser | Asp | Thr | Phe |
|---|---|---|---|---|---|---|---|---|---|---|---|---|---|---|---|
| | | | 35 | | | | | 40 | | | | | 45 | | |

| Cys | Cys | Asn | Met | Ala | Ser | Ala | Leu | Leu | Ser | Ala | Thr | Val | Gln | Arg | Leu |
|---|---|---|---|---|---|---|---|---|---|---|---|---|---|---|---|
| 50 | | | | | 55 | | | | | 60 | | | | | |

| Gln | Ala | Ser | Ala | Gly | Glu | Gln | Gly | Glu | Gly | Asn | Thr | Ile | Leu | Gln | His |
|---|---|---|---|---|---|---|---|---|---|---|---|---|---|---|---|
| 65 | | | | | 70 | | | | | 75 | | | | | 80 |

| Ile | Ser | Thr | Leu | Glu | Thr | Ile | Tyr | Gln | Arg | Asp | Pro | Leu | Lys | Leu | Val |
|---|---|---|---|---|---|---|---|---|---|---|---|---|---|---|---|
| | | | | 85 | | | | | 90 | | | | | 95 | |

| Ala | Thr | Cys | Arg | His | Ile | Leu | Gln | Gly | Glu | Lys | Lys | Ala | Val | Met | Glu |
|---|---|---|---|---|---|---|---|---|---|---|---|---|---|---|---|
| | | | 100 | | | | | 105 | | | | | 110 | | |

| Gln | Phe | His | His | Leu | Pro | Met | Ser | Phe | His | Trp | Lys | Gln | Glu | Glu | Leu |
|---|---|---|---|---|---|---|---|---|---|---|---|---|---|---|---|
| | | | 115 | | | | | 120 | | | | | 125 | | |

| Lys | Phe | Asn | Thr | Val | Leu | Arg | Arg | Leu | Gln | His | Arg | Ala | Gly | Glu | Thr |
|---|---|---|---|---|---|---|---|---|---|---|---|---|---|---|---|
| 130 | | | | | 135 | | | | | 140 | | | | | |

| Arg | Leu | Leu | Arg | Glu | Ala | Leu | Gln | Pro | Gly | Ala | Glu | Ala | Gly | Gln | Val |
|---|---|---|---|---|---|---|---|---|---|---|---|---|---|---|---|
| 145 | | | | | 150 | | | | | 155 | | | | | 160 |

| Ser | Leu | His | Ser | Leu | Ile | Glu | Thr | Pro | Thr | Asn | Gly | Thr | Gly | Pro | Ser |
|---|---|---|---|---|---|---|---|---|---|---|---|---|---|---|---|
| | | | | 165 | | | | | 170 | | | | | 175 | |

| Glu | Ala | Leu | Val | Thr | Leu | Leu | Gln | Glu | Thr | Val | Gly | Glu | Leu | Glu | Ala |
|---|---|---|---|---|---|---|---|---|---|---|---|---|---|---|---|
| | | | 180 | | | | | 185 | | | | | 190 | | |

| Ala | Gln | Ala | Leu | Val | Leu | Lys | Arg | Ile | Gln | Ile | Trp | Lys | Arg | Gln | Gln |
|---|---|---|---|---|---|---|---|---|---|---|---|---|---|---|---|
| | | | 195 | | | | | 200 | | | | | 205 | | |

| Gln | Leu | Ala | Gly | Asn | Gly | Ala | Pro | Phe | Glu | Glu | Ser | Leu | Ala | Pro | Leu |
|---|---|---|---|---|---|---|---|---|---|---|---|---|---|---|---|
| 210 | | | | | 215 | | | | | 220 | | | | | |

| Gln | Glu | Arg | Cys | Glu | Ser | Leu | Val | Asp | Ile | Tyr | Ser | Gln | Leu | Gln | Gln |
|---|---|---|---|---|---|---|---|---|---|---|---|---|---|---|---|
| 225 | | | | | 230 | | | | | 235 | | | | | 240 |

| Glu | Val | Gly | Ala | Ala | Gly | Gly | Glu | Leu | Asp | Pro | Lys | Thr | Arg | Ala | Ala |
|---|---|---|---|---|---|---|---|---|---|---|---|---|---|---|---|
| | | | | 245 | | | | | 250 | | | | | 255 | |

| Leu | Ile | Ser | Arg | Leu | Asp | Glu | Val | Leu | Arg | Thr | Leu | Val | Thr | Ser | Ser |
|---|---|---|---|---|---|---|---|---|---|---|---|---|---|---|---|
| | | | 260 | | | | | 265 | | | | | 270 | | |

```
Phe Leu Val Glu Lys Gln Pro Pro Gln Val Leu Lys Thr Gln Thr Lys
        275                 280                 285

Phe Gln Ala Gly Val Arg Phe Leu Gly Leu Arg Phe Leu Gly Ala
290                 295                 300

Pro Ala Lys Pro Pro Leu Val Arg Ala Asp Met Val Thr Glu Lys Gln
305                 310                 315                 320

Ala Arg Glu Leu Ser Met Pro Gln Gly Pro Ala Gly Ala Glu Ser
            325                 330                 335

Thr Gly Glu Ile Ile Asn Asn Thr Val Pro Leu Glu Asn Ser Ile Pro
                340                 345                 350

Gly Asn Cys Cys Ser Ala Leu Phe Lys Asn Leu Leu Lys Lys Ile
            355                 360                 365

Lys Arg Cys Glu Arg Lys Gly Thr Glu Ser Val Thr Glu Lys Cys
370                 375                 380

Ala Val Leu Phe Ser Thr Ser Leu Thr Leu Gly Pro Asn Lys Leu Pro
385                 390                 395                 400

Ile Gln Leu Gln Ala Leu Ser Leu Pro Leu Val Val Ile Val His Gly
                405                 410                 415

Asn Gln Asp Asn Asn Ala Lys Ala Thr Ile Leu Trp Asp Asn Ala Phe
            420                 425                 430

Ser Glu Met Asp Arg Val Pro Phe Val Val Ala Glu Arg Val Pro Trp
        435                 440                 445

Glu Lys Met Cys Glu Thr Leu Asn Leu Lys Phe Met Ala Glu Val Gly
    450                 455                 460

Thr Asn Arg Gly Leu Leu Pro Glu His Phe Leu Phe Leu Ala Gln Lys
465                 470                 475                 480

Ile Phe Asn Asp Asn Ser Leu Ser Ile Glu Ala Phe Gln His Arg Ser
            485                 490                 495

Val Ser Trp Ser Gln Phe Asn Lys Glu Ile Leu Leu Gly Arg Gly Phe
        500                 505                 510

Thr Phe Trp Gln Trp Phe Asp Gly Val Leu Asp Leu Thr Lys Arg Cys
    515                 520                 525

Leu Arg Ser Tyr Trp Ser Asp Arg Leu Ile Ile Gly Phe Ile Ser Lys
530                 535                 540

Gln Tyr Val Thr Ser Leu Leu Asn Glu Pro Asp Gly Thr Phe Leu
545                 550                 555                 560

Leu Arg Phe Ser Asp Ser Glu Ile Gly Gly Ile Thr Ile Ala His Val
            565                 570                 575

Ile Arg Gly Gln Asp Gly Ser Pro Gln Ile Glu Asn Ile Gln Pro Phe
        580                 585                 590

Ser Ala Lys Asp Leu Ser Ile Arg Ser Leu Gly Asp Arg Ile Arg Asp
    595                 600                 605

Leu Ala Gln Leu Lys Asn Leu Tyr Pro Lys Lys Pro Lys Asp Glu Ala
610                 615                 620

Phe Arg Ser His Tyr Lys Pro Glu Gln Met Gly Lys Asp Gly Arg Gly
625                 630                 635                 640

Tyr Val Pro Ala Thr Ile Lys Met Thr Val Glu Arg Asp Gln Pro Leu
            645                 650                 655

Pro Thr Pro Glu Pro Gln Met Pro Thr Met Val Pro Ser Tyr Asp Leu
        660                 665                 670

Gly Met Ala Pro Asp Ser Ser Met Asn Leu Gln Leu Gly Pro Asp Met
    675                 680                 685

Val Pro Gln Val Tyr Pro Pro Arg Ser His Ser Ile Pro Ser Tyr Pro
690                 695                 700
```

```
Ala Leu Pro Arg Glu Glu Ser Val Asn Met Leu Pro Ala Phe Gln Glu
705                 710                 715                 720

Pro His Leu Pro Met Pro Pro Asn Leu Ser Gln Met Ser Leu Pro Phe
            725                 730                 735

Asp Gln Pro His Pro Gln Gly Leu Leu Pro Cys Pro Pro Gln Asp His
        740                 745                 750

Ala Val Ser Ser Pro Glu Pro Leu Leu Cys Ser Asp Val Thr Met Ala
    755                 760                 765

Glu Asp Ser Cys Leu Asn Gln Pro Val Gly Gly Phe Pro Gln Gly Thr
770                 775                 780

Trp Val Arg Glu Asp Met Phe Pro Pro Leu Leu Pro Pro Thr Glu Gln
785                 790                 795                 800

Asp Leu Thr Lys Leu Leu Leu Glu Gly Gln Gly Glu Ser Gly Gly Gly
                805                 810                 815

Ser Leu Gly Pro Gln Pro Leu Leu Gln Pro Ser Pro Tyr Gly Gln Ser
            820                 825                 830

Gly Ile Ser Met Ser His Leu Asp Leu Arg Ala Asn Pro Ser Trp
            835                 840                 845

<210> SEQ ID NO 41
<211> LENGTH: 787
<212> TYPE: PRT
<213> ORGANISM: Equus caballus
<220> FEATURE:
<223> OTHER INFORMATION: horse signal transducer and activator of
      transcription 6 (STAT6), interleukin-4-induced
      transcription factor (IL-4 Stat)

<400> SEQUENCE: 41

Met Ser Val Trp Gly Leu Val Leu Lys Met Pro Pro Glu Lys Leu Gln
1               5                   10                  15

Arg Leu Tyr Val Asp Phe Pro Gln His Leu Arg His Leu Leu Gly Asp
                20                  25                  30

Trp Leu Glu Asn Gln Pro Trp Glu Phe Leu Val Gly Ser Asp Ala Phe
            35                  40                  45

Cys Cys Asn Met Ala Ser Ala Leu Leu Ser Ala Thr Leu Gln His Leu
    50                  55                  60

Gln Thr Leu Ala Gly Glu Gln Gly Glu Gly Ser Ala Ile Leu Gln His
65                  70                  75                  80

Ile Ser Thr Leu Glu Ser Ile Tyr Gln Arg Asp Pro Leu Lys Leu Val
                85                  90                  95

Ala Thr Phe Lys His Ile Leu Gln Gly Glu Arg Lys Ala Val Met Glu
                100                 105                 110

Gln Phe His His Leu Pro Met Pro Phe His Arg Lys Gln Glu Glu Leu
            115                 120                 125

Lys Phe Asn Thr Val Leu Arg Arg Leu Gln His Arg Val Gly Glu Thr
130                 135                 140

Arg Leu Leu Arg Glu Ala Leu Lys Gln Gly Ala Glu Ala Gly Gln Val
145                 150                 155                 160

Ser Leu His Ser Leu Ile Glu Thr Pro Ala Asn Gly Ser Gly Pro Ser
                165                 170                 175

Glu Ala Leu Ala Thr Leu Leu Gln Glu Ala Val Ala Glu Leu Glu Ala
            180                 185                 190

Ala Gln Ala Leu Val Leu Lys Arg Ile Gln Ile Trp Lys Arg Gln Gln
        195                 200                 205

Gln Leu Ala Gly Asn Gly Ala Pro Phe Glu Glu Ser Leu Ala Ser Leu
```

-continued

```
            210                 215                 220
Gln Glu Arg Cys Glu Ser Leu Val Asp Ile Tyr Ser Gln Leu Gln Gln
225                 230                 235                 240

Glu Val Gly Ala Ala Gly Gly Glu Leu Glu Pro Lys Thr Arg Ala Val
                245                 250                 255

Leu Ile Ser Arg Leu Glu Glu Val Leu Arg Thr Leu Val Thr Ser Ser
                260                 265                 270

Phe Leu Val Glu Lys Gln Pro Pro Gln Val Leu Lys Thr Gln Thr Lys
                275                 280                 285

Phe Gln Ala Gly Val Arg Phe Leu Leu Gly Leu Arg Phe Leu Gly Ala
290                 295                 300

Pro Ala Lys Pro Val Val Arg Ala Asp Met Val Thr Glu Lys Gln
305                 310                 315                 320

Ala Arg Glu Leu Ser Met Pro Gln Gly Pro Gly Ala Gly Thr Glu Ser
                325                 330                 335

Ser Gly Glu Ile Ile Asn Asn Thr Val Pro Leu Glu Asn Ser Ile Pro
                340                 345                 350

Gly Asn Cys Cys Ser Ala Leu Phe Lys Asn Leu Leu Leu Lys Lys Ile
                355                 360                 365

Lys Arg Cys Glu Arg Lys Gly Thr Glu Ser Val Thr Glu Glu Lys Cys
                370                 375                 380

Ala Val Leu Phe Ser Thr Ser Phe Ala Leu Gly Pro Asn Lys Leu His
385                 390                 395                 400

Ile Gln Leu Gln Ala Leu Ser Leu Pro Leu Val Val Ile Val His Gly
                405                 410                 415

Asn Gln Asp Asn Asn Ala Lys Ala Thr Ile Leu Trp Asp Asn Ala Phe
                420                 425                 430

Ser Glu Met Asp Arg Val Pro Phe Val Val Ala Glu Arg Val Pro Trp
                435                 440                 445

Glu Lys Met Cys Glu Thr Leu Asn Leu Lys Phe Met Ala Glu Val Gly
                450                 455                 460

Thr Asn Arg Gly Leu Leu Pro Glu His Phe Leu Phe Leu Ala Gln Lys
465                 470                 475                 480

Ile Phe Asn Asp Asn Ser Leu Ser Thr Glu Ala Phe Gln His Arg Ser
                485                 490                 495

Val Ser Trp Ser Gln Phe Asn Lys Glu Ile Leu Leu Gly Arg Gly Phe
                500                 505                 510

Thr Phe Trp Gln Trp Phe Asp Gly Val Leu Asp Leu Thr Lys Arg Cys
                515                 520                 525

Leu Arg Ser Tyr Trp Ser Asp Arg Leu Ile Ile Gly Phe Ile Ser Lys
530                 535                 540

Gln Tyr Val Thr Ser Leu Leu Asn Glu Pro Asp Gly Thr Phe Leu
545                 550                 555                 560

Leu Arg Phe Ser Asp Ser Glu Ile Gly Gly Ile Thr Ile Ala His Val
                565                 570                 575

Ile Arg Gly Gln Asp Gly Ser Ser Gln Ile Glu Asn Ile Gln Pro Phe
                580                 585                 590

Ser Ala Lys Asp Leu Ser Ile Arg Ser Leu Gly Asp Arg Ile Arg Asp
                595                 600                 605

Leu Ala Gln Leu Lys Asn Leu Tyr Pro Lys Lys Pro Lys Asp Glu Ala
                610                 615                 620

Phe Arg Ser His Tyr Lys Pro Glu Gln Met Gly Lys Asp Gly Arg Gly
625                 630                 635                 640
```

```
Tyr Val Pro Ala Thr Ile Lys Met Thr Val Glu Arg Asp Gln Pro Leu
                645                 650                 655

Pro Thr Pro Glu Pro Gln Met Pro Thr Met Met Pro Thr Tyr Asp Leu
            660                 665                 670

Gly Met Ala Pro Asp Ser Ser Met Asn Met Gln Leu Gly Pro Asp Met
        675                 680                 685

Val Pro Gln Val Tyr Pro Pro His Ser His Ser Met Pro Ser Tyr Gln
    690                 695                 700

Gly Leu Ser Arg Glu Glu Ser Val Ser Val Leu Pro Ala Phe Pro Glu
705                 710                 715                 720

Pro His Leu Pro Met Pro Pro Thr Leu Ser Gln Met Ser Leu Pro Phe
                725                 730                 735

Asp Gln Pro His Pro Gln Gly Leu Leu Pro Cys Gln Pro Gln Glu His
            740                 745                 750

Ala Val Ser Ser Pro Glu Pro Leu Leu Cys Ser Asp Val Thr Met Ala
        755                 760                 765

Glu Glu Ser Cys Leu Ser Gln Pro Val Gly Gly Phe Leu Arg Ala Asn
770                 775                 780

Pro Ser Trp
785

<210> SEQ ID NO 42
<211> LENGTH: 844
<212> TYPE: PRT
<213> ORGANISM: Canis lupus familiaris
<220> FEATURE:
<223> OTHER INFORMATION: dog signal transducer and activator of
      transcription 6 (STAT6), interleukin-4-induced
      transcription factor (IL-4 Stat)

<400> SEQUENCE: 42

Met Ser Leu Trp Ser Leu Val Ser Lys Met Pro Pro Glu Lys Leu Gln
1               5                   10                  15

Arg Leu Tyr Val Asp Phe Pro Gln His Leu Arg His Leu Leu Ser Asp
                20                  25                  30

Trp Leu Glu Asn Gln Pro Trp Glu Phe Leu Val Gly Ser Asp Thr Phe
            35                  40                  45

Cys Cys Asn Met Ala Ser Ala Leu Leu Ser Ala Thr Val Gln Arg Leu
    50                  55                  60

Gln Ala Ser Ala Gly Lys Gly Glu Gly Ser Thr Ile Leu Gln His
65                  70                  75                  80

Ile Ser Thr Leu Glu Ser Ile Tyr Gln Arg Asp Pro Leu Lys Leu Val
                85                  90                  95

Ala Thr Phe Arg Gln Ile Leu Gly Glu Lys Lys Ala Val Met Glu
            100                 105                 110

Gln Phe Arg His Leu Pro Met Pro Phe His Trp Lys Gln Glu Glu Leu
        115                 120                 125

Lys Phe Asn Thr Ala Leu Gln Arg Leu Gln His Arg Val Gly Glu Thr
130                 135                 140

Arg Leu Leu Arg Glu Ala Leu Gln Pro Gly Ala Glu Ala Gly Gln Val
145                 150                 155                 160

Ser Leu Arg Ser Leu Ile Asp Ala Pro Ala Asn Gly Thr Gly Pro Arg
                165                 170                 175

Glu Ala Leu Ala Thr Leu Leu Gln Glu Thr Val Gly Glu Leu Glu Ala
            180                 185                 190

Ala Gln Ala Leu Val Leu Lys Arg Ile Gln Ile Trp Lys Arg Gln Gln
        195                 200                 205
```

```
Gln Leu Ala Gly Asn Gly Ala Pro Phe Glu Glu Ser Leu Ala Pro Leu
    210                 215                 220
Gln Glu Arg Cys Glu Ser Leu Val Asp Ile Tyr Ser Gln Leu Gln Gln
225                 230                 235                 240
Glu Val Gly Ala Ala Gly Gly Glu Leu Glu Pro Lys Ala Arg Ala Val
                    245                 250                 255
Leu Ser Ser Arg Leu Asp Glu Val Leu Arg Ser Leu Val Thr Ser Ser
                260                 265                 270
Phe Leu Val Glu Lys Gln Pro Pro Gln Val Leu Lys Thr Gln Thr Lys
            275                 280                 285
Phe Gln Ala Gly Val Arg Phe Leu Leu Gly Leu Arg Phe Leu Gly Ala
        290                 295                 300
Pro Ala Lys Pro Pro Leu Val Arg Ala Asp Met Val Thr Glu Lys Gln
305                 310                 315                 320
Ala Arg Glu Leu Ser Met Pro Gln Gly Pro Gly Ala Gly Ala Glu Ser
                    325                 330                 335
Thr Gly Glu Ile Ile Asn Asn Thr Val Ala Leu Glu Asn Ser Ile Pro
                340                 345                 350
Gly Asn Cys Cys Ser Ala Leu Phe Lys Asn Leu Leu Leu Lys Lys Ile
            355                 360                 365
Lys Arg Cys Glu Arg Lys Gly Thr Glu Ser Val Thr Glu Glu Lys Cys
        370                 375                 380
Ala Val Leu Phe Ser Thr Ser Leu Ala Leu Gly Pro Asn Lys Leu Pro
385                 390                 395                 400
Val Gln Leu Gln Ala Leu Ser Leu Pro Leu Val Val Ile Val His Gly
                    405                 410                 415
Asn Gln Asp Asn Asn Ala Lys Ala Thr Ile Leu Trp Asp Asn Ala Phe
                420                 425                 430
Ser Glu Met Asp Arg Val Pro Phe Val Val Ala Glu Arg Val Pro Trp
            435                 440                 445
Glu Lys Met Cys Glu Thr Leu Asn Leu Lys Phe Met Ala Glu Val Gly
        450                 455                 460
Thr Asn Arg Gly Leu Leu Pro Glu His Phe Leu Phe Leu Ala Gln Lys
465                 470                 475                 480
Ile Phe Asn Asp Asn Ser Leu Ser Met Glu Ala Phe Gln His Arg Ser
                    485                 490                 495
Val Ser Trp Ser Gln Phe Asn Lys Glu Ile Leu Leu Gly Arg Gly Phe
                500                 505                 510
Thr Phe Trp Gln Trp Phe Asp Gly Val Leu Asp Leu Thr Lys Arg Cys
            515                 520                 525
Leu Arg Ser Tyr Trp Ser Asp Arg Leu Ile Ile Gly Phe Ile Ser Lys
        530                 535                 540
Gln Tyr Val Thr Ser Leu Leu Leu Asn Glu Pro Asp Gly Thr Phe Leu
545                 550                 555                 560
Leu Arg Phe Ser Asp Ser Glu Ile Gly Gly Ile Thr Ile Ala His Val
                    565                 570                 575
Ile Arg Gly Gln Asp Gly Ser Pro Gln Ile Glu Asn Ile Gln Pro Phe
                580                 585                 590
Ser Ala Lys Asp Leu Ser Ile Arg Ser Leu Gly Asp Arg Ile Arg Asp
            595                 600                 605
Leu Ala Gln Leu Lys Asn Leu Tyr Pro Lys Lys Pro Lys Asp Glu Ala
        610                 615                 620
Phe Arg Ser His Tyr Lys Pro Glu Gln Met Gly Lys Asp Gly Arg Gly
```

```
                625                 630                 635                 640
Tyr Val Pro Ala Thr Ile Lys Met Thr Val Glu Arg Asp Gln Pro Leu
                    645                 650                 655

Pro Thr Leu Glu Pro Gln Met Pro Thr Met Val Pro Thr Tyr Asp Leu
                    660                 665                 670

Gly Met Ala Thr Glu Ser Ser Met Asn Met Gln Leu Ser Pro Asp Met
                    675                 680                 685

Val Ser Gln Val Tyr Pro Pro His Ser His Ser Met Pro Ser Phe Gln
                    690                 695                 700

Ala Leu Ser Arg Glu Asp Val Leu Pro Thr Phe Gln Glu Ser His Leu
705                 710                 715                 720

Gln Met Pro Pro Asn Leu Ser Gln Ile Asn Leu Pro Phe Asp Gln Pro
                    725                 730                 735

His Pro Gln Gly Leu Leu Pro Cys Gln Ser Gln Glu His Ala Val Ser
                    740                 745                 750

Thr Pro Glu Pro Leu Leu Cys Ser Asp Val Pro Met Thr Glu Asp Ser
                    755                 760                 765

Cys Leu Ser Gln Pro Val Gly Gly Phe Pro Gln Ser Thr Trp Val Gly
770                 775                 780

Glu Asp Met Phe Pro Pro Leu Leu Pro Pro Thr Glu Gln Asp Leu Thr
785                 790                 795                 800

Lys Leu Leu Leu Glu Gly Gln Gly Glu Ser Gly Gly Gly Ser Leu Gly
                    805                 810                 815

Thr Gln Pro Leu Leu Gln Pro Ser His Tyr Gly Gln Ser Gly Ile Ser
                    820                 825                 830

Met Ser His Leu Asp Leu Arg Ala Asn Pro Ser Trp
                835                 840

<210> SEQ ID NO 43
<211> LENGTH: 847
<212> TYPE: PRT
<213> ORGANISM: Homo sapiens
<220> FEATURE:
<223> OTHER INFORMATION: human signal transducer and activator of
      transcription 6 (STAT6), interleukin-4-induced
      transcription factor (IL-4 Stat)

<400> SEQUENCE: 43

Met Ser Leu Trp Gly Leu Val Ser Lys Met Pro Pro Glu Lys Val Gln
1               5                   10                  15

Arg Leu Tyr Val Asp Phe Pro Gln His Leu Arg His Leu Leu Gly Asp
                20                  25                  30

Trp Leu Glu Ser Gln Pro Trp Glu Phe Leu Val Gly Ser Asp Ala Phe
            35                  40                  45

Cys Cys Asn Leu Ala Ser Ala Leu Leu Ser Asp Thr Val Gln His Leu
50                  55                  60

Gln Ala Ser Val Gly Glu Gln Gly Glu Gly Ser Thr Ile Leu Gln His
65                  70                  75                  80

Ile Ser Thr Leu Glu Ser Ile Tyr Gln Arg Asp Pro Leu Lys Leu Val
                85                  90                  95

Ala Thr Phe Arg Gln Ile Leu Gln Gly Glu Lys Lys Ala Val Met Glu
                100                 105                 110

Gln Phe Arg His Leu Pro Met Pro Phe His Trp Lys Gln Glu Glu Leu
            115                 120                 125

Lys Phe Lys Thr Gly Leu Arg Arg Leu Gln His Arg Val Gly Glu Ile
    130                 135                 140
```

```
His Leu Leu Arg Glu Ala Leu Gln Lys Gly Ala Glu Ala Gly Gln Val
145                 150                 155                 160

Ser Leu His Ser Leu Ile Glu Thr Pro Ala Asn Gly Thr Gly Pro Ser
            165                 170                 175

Glu Ala Leu Ala Met Leu Leu Gln Glu Thr Thr Gly Glu Leu Glu Ala
        180                 185                 190

Ala Lys Ala Leu Val Leu Lys Arg Ile Gln Ile Trp Lys Arg Gln Gln
    195                 200                 205

Gln Leu Ala Gly Asn Gly Ala Pro Phe Glu Ser Leu Ala Pro Leu
210                 215                 220

Gln Glu Arg Cys Glu Ser Leu Val Asp Ile Tyr Ser Gln Leu Gln Gln
225                 230                 235                 240

Glu Val Gly Ala Ala Gly Gly Glu Leu Glu Pro Lys Thr Arg Ala Ser
                245                 250                 255

Leu Thr Gly Arg Leu Asp Glu Val Leu Arg Thr Leu Val Thr Ser Cys
            260                 265                 270

Phe Leu Val Glu Lys Gln Pro Pro Gln Val Leu Lys Thr Gln Thr Lys
        275                 280                 285

Phe Gln Ala Gly Val Arg Phe Leu Leu Gly Leu Arg Phe Leu Gly Ala
    290                 295                 300

Pro Ala Lys Pro Pro Leu Val Arg Ala Asp Met Val Thr Glu Lys Gln
305                 310                 315                 320

Ala Arg Glu Leu Ser Val Pro Gln Gly Pro Gly Ala Gly Ala Glu Ser
                325                 330                 335

Thr Gly Glu Ile Ile Asn Asn Thr Val Pro Leu Glu Asn Ser Ile Pro
            340                 345                 350

Gly Asn Cys Cys Ser Ala Leu Phe Lys Asn Leu Leu Leu Lys Lys Ile
        355                 360                 365

Lys Arg Cys Glu Arg Lys Gly Thr Glu Ser Val Thr Glu Glu Lys Cys
    370                 375                 380

Ala Val Leu Phe Ser Ala Ser Phe Thr Leu Gly Pro Gly Lys Leu Pro
385                 390                 395                 400

Ile Gln Leu Gln Ala Leu Ser Leu Pro Leu Val Val Ile Val His Gly
                405                 410                 415

Asn Gln Asp Asn Asn Ala Lys Ala Thr Ile Leu Trp Asp Asn Ala Phe
            420                 425                 430

Ser Glu Met Asp Arg Val Pro Phe Val Val Ala Glu Arg Val Pro Trp
        435                 440                 445

Glu Lys Met Cys Glu Thr Leu Asn Leu Lys Phe Met Ala Glu Val Gly
    450                 455                 460

Thr Asn Arg Gly Leu Leu Pro Glu His Phe Leu Phe Leu Ala Gln Lys
465                 470                 475                 480

Ile Phe Asn Asp Asn Ser Leu Ser Met Glu Ala Phe Gln His Arg Ser
                485                 490                 495

Val Ser Trp Ser Gln Phe Asn Lys Glu Ile Leu Leu Gly Arg Gly Phe
            500                 505                 510

Thr Phe Trp Gln Trp Phe Asp Gly Val Leu Asp Leu Thr Lys Arg Cys
        515                 520                 525

Leu Arg Ser Tyr Trp Ser Asp Arg Leu Ile Ile Gly Phe Ile Ser Lys
    530                 535                 540

Gln Tyr Val Thr Ser Leu Leu Leu Asn Glu Pro Asp Gly Thr Phe Leu
545                 550                 555                 560

Leu Arg Phe Ser Asp Ser Glu Ile Gly Gly Ile Thr Ile Ala His Val
                565                 570                 575
```

Ile Arg Gly Gln Asp Gly Ser Pro Gln Ile Glu Asn Ile Gln Pro Phe
                580                 585                 590

Ser Ala Lys Asp Leu Ser Ile Arg Ser Leu Gly Asp Arg Ile Arg Asp
                595                 600                 605

Leu Ala Gln Leu Lys Asn Leu Tyr Pro Lys Lys Pro Lys Asp Glu Ala
            610                 615                 620

Phe Arg Ser His Tyr Lys Pro Glu Gln Met Gly Lys Asp Gly Arg Gly
625                 630                 635                 640

Tyr Val Pro Ala Thr Ile Lys Met Thr Val Glu Arg Asp Gln Pro Leu
                645                 650                 655

Pro Thr Pro Glu Leu Gln Met Pro Thr Met Val Pro Ser Tyr Asp Leu
                660                 665                 670

Gly Met Ala Pro Asp Ser Ser Met Ser Met Gln Leu Gly Pro Asp Met
                675                 680                 685

Val Pro Gln Val Tyr Pro Pro His Ser His Ser Ile Pro Pro Tyr Gln
                690                 695                 700

Gly Leu Ser Pro Glu Glu Ser Val Asn Val Leu Ser Ala Phe Gln Glu
705                 710                 715                 720

Pro His Leu Gln Met Pro Pro Ser Leu Gly Gln Met Ser Leu Pro Phe
                725                 730                 735

Asp Gln Pro His Pro Gln Gly Leu Leu Pro Cys Gln Pro Gln Glu His
                740                 745                 750

Ala Val Ser Ser Pro Asp Pro Leu Leu Cys Ser Asp Val Thr Met Val
                755                 760                 765

Glu Asp Ser Cys Leu Ser Gln Pro Val Thr Ala Phe Pro Gln Gly Thr
770                 775                 780

Trp Ile Gly Glu Asp Ile Phe Pro Pro Leu Leu Pro Pro Thr Glu Gln
785                 790                 795                 800

Asp Leu Thr Lys Leu Leu Leu Glu Gly Gln Gly Glu Ser Gly Gly Gly
                805                 810                 815

Ser Leu Gly Ala Gln Pro Leu Leu Gln Pro Ser His Tyr Gly Gln Ser
                820                 825                 830

Gly Ile Ser Met Ser His Met Asp Leu Arg Ala Asn Pro Ser Trp
                835                 840                 845

<210> SEQ ID NO 44
<211> LENGTH: 837
<212> TYPE: PRT
<213> ORGANISM: Mus musculus
<220> FEATURE:
<223> OTHER INFORMATION: mouse signal transducer and activator of
    transcription 6 (STAT6), interleukin-4-induced
    transcription factor (IL-4 Stat)

<400> SEQUENCE: 44

Met Ser Leu Trp Gly Leu Ile Ser Lys Met Ser Pro Glu Lys Leu Gln
1               5                   10                  15

Arg Leu Tyr Val Asp Phe Pro Gln Arg Leu Arg His Leu Leu Ala Asp
            20                  25                  30

Trp Leu Glu Ser Gln Pro Trp Glu Phe Leu Val Gly Ser Asp Ala Phe
        35                  40                  45

Cys Tyr Asn Met Ala Ser Ala Leu Leu Ser Ala Thr Val Gln Arg Leu
    50                  55                  60

Gln Ala Thr Ala Gly Glu Gln Gly Lys Gly Asn Ser Ile Leu Pro His
65                  70                  75                  80

Ile Ser Thr Leu Glu Ser Ile Tyr Gln Arg Asp Pro Leu Lys Leu Val

-continued

```
                85                  90                  95
Ala Thr Ile Arg Gln Ile Leu Gln Gly Glu Lys Lys Ala Val Ile Glu
                   100                 105                 110
Glu Phe Arg His Leu Pro Gly Pro Phe His Arg Lys Gln Glu Glu Leu
               115                 120                 125
Lys Phe Thr Thr Ala Leu Gly Arg Leu Gln His Arg Val Arg Glu Thr
           130                 135                 140
Arg Leu Leu Arg Glu Ser Leu Gln Gln Gly Ala Lys Thr Gly Gln Val
145                 150                 155                 160
Ser Leu Gln Asn Leu Ile Asp Pro Pro Val Asn Gly Pro Gly Pro Ser
                   165                 170                 175
Glu Asp Leu Ala Thr Met Leu Gln Gly Thr Val Gly Asp Leu Glu Ala
               180                 185                 190
Thr Gln Ala Leu Val Leu Lys Arg Ile Gln Ile Trp Lys Arg Gln Gln
           195                 200                 205
Gln Leu Ala Gly Asn Gly Thr Pro Phe Glu Glu Ser Leu Ala Gly Leu
               210                 215                 220
Gln Glu Arg Cys Glu Ser Leu Val Glu Ile Tyr Ser Gln Leu Gln Gln
225                 230                 235                 240
Glu Ile Gly Ala Ala Ser Gly Glu Leu Glu Pro Lys Thr Arg Ala Ser
                   245                 250                 255
Leu Ile Ser Arg Leu Asp Glu Val Leu Arg Thr Leu Val Thr Ser Ser
               260                 265                 270
Phe Leu Val Glu Lys Gln Pro Pro Gln Val Leu Lys Thr Gln Thr Lys
           275                 280                 285
Phe Gln Ala Gly Val Arg Phe Leu Leu Gly Leu Gln Phe Leu Gly Thr
       290                 295                 300
Ser Ala Lys Pro Pro Met Val Arg Ala Asp Met Val Thr Glu Lys Gln
305                 310                 315                 320
Ala Arg Glu Leu Ser Leu Ala Gln Gly Pro Gly Thr Gly Val Glu Ser
                   325                 330                 335
Thr Gly Glu Ile Met Asn Asn Thr Val Pro Leu Glu Asn Ser Ile Pro
               340                 345                 350
Ser Asn Cys Cys Ser Ala Leu Phe Lys Asn Leu Leu Leu Lys Lys Ile
           355                 360                 365
Lys Arg Cys Glu Arg Lys Gly Thr Glu Ser Val Thr Glu Glu Lys Cys
       370                 375                 380
Ala Val Leu Phe Ser Thr Ser Phe Thr Leu Gly Pro Asn Lys Leu Leu
385                 390                 395                 400
Ile Gln Leu Gln Ala Leu Ser Leu Pro Leu Val Val Ile Val His Gly
                   405                 410                 415
Asn Gln Asp Asn Asn Ala Lys Ala Thr Ile Leu Trp Asp Asn Ala Phe
               420                 425                 430
Ser Glu Met Asp Arg Val Pro Phe Val Val Ala Glu Arg Val Pro Trp
           435                 440                 445
Glu Lys Met Cys Glu Thr Leu Asn Leu Lys Phe Met Ala Glu Val Gly
       450                 455                 460
Thr Ser Arg Gly Leu Leu Pro Glu His Phe Leu Phe Leu Ala Gln Lys
465                 470                 475                 480
Ile Phe Asn Asp Asn Ser Leu Ser Val Glu Ala Phe Gln His Arg Cys
                   485                 490                 495
Val Ser Trp Ser Gln Phe Asn Lys Glu Ile Leu Leu Gly Arg Gly Phe
               500                 505                 510
```

-continued

```
Thr Phe Trp Gln Trp Phe Asp Gly Val Leu Asp Leu Thr Lys Arg Cys
            515                 520                 525

Leu Arg Ser Tyr Trp Ser Asp Arg Leu Ile Ile Gly Phe Ile Ser Lys
        530                 535                 540

Gln Tyr Val Thr Ser Leu Leu Leu Asn Glu Pro Asp Gly Thr Phe Leu
545                 550                 555                 560

Leu Arg Phe Ser Asp Ser Glu Ile Gly Gly Ile Thr Ile Ala His Val
                565                 570                 575

Ile Arg Gly Gln Asp Gly Ser Ser Gln Ile Glu Asn Ile Gln Pro Phe
                580                 585                 590

Ser Ala Lys Asp Leu Ser Ile Arg Ser Leu Gly Asp Arg Ile Arg Asp
        595                 600                 605

Leu Ala Gln Leu Lys Asn Leu Tyr Pro Lys Lys Pro Lys Asp Glu Ala
610                 615                 620

Phe Arg Ser His Tyr Lys Pro Glu Gln Met Gly Lys Asp Gly Arg Gly
625                 630                 635                 640

Tyr Val Ser Thr Thr Ile Lys Met Thr Val Glu Arg Asp Gln Pro Leu
                645                 650                 655

Pro Thr Pro Glu Pro Gln Met Pro Ala Met Val Pro Pro Tyr Asp Leu
            660                 665                 670

Gly Met Ala Pro Asp Ala Ser Met Gln Leu Ser Ser Asp Met Gly Tyr
            675                 680                 685

Pro Pro Gln Ser Ile His Ser Phe Gln Ser Leu Glu Glu Ser Met Ser
        690                 695                 700

Val Leu Pro Ser Phe Gln Glu Pro His Leu Gln Met Pro Pro Asn Met
705                 710                 715                 720

Ser Gln Ile Thr Met Pro Phe Asp Gln Pro His Pro Gln Gly Leu Leu
                725                 730                 735

Gln Cys Gln Ser Gln Glu His Ala Val Ser Ser Pro Glu Pro Met Leu
                740                 745                 750

Cys Ser Asp Val Thr Met Val Glu Asp Ser Cys Leu Thr Gln Pro Val
            755                 760                 765

Gly Gly Phe Pro Gln Gly Thr Trp Val Ser Glu Asp Met Tyr Pro Pro
770                 775                 780

Leu Met Pro Pro Thr Glu Gln Asp Leu Thr Lys Leu Leu Leu Glu Asn
785                 790                 795                 800

Gln Gly Glu Ala Gly Gly Ser Leu Gly Ser Gln Pro Leu Leu Gln Pro
                805                 810                 815

Ser Pro Tyr Gly Gln Ser Gly Ile Ser Leu Ser His Leu Asp Leu Arg
            820                 825                 830

Thr Asn Pro Ser Trp
            835
```